US010370346B2

(12) United States Patent
McCall et al.

(10) Patent No.: US 10,370,346 B2
(45) Date of Patent: Aug. 6, 2019

(54) KDM1A INHIBITORS FOR THE TREATMENT OF DISEASE

(71) Applicant: Imago Biosciences, Inc., San Carlos, CA (US)

(72) Inventors: John M. McCall, Boca Grande, FL (US); Hugh Y. Rienhoff, Jr., San Carlos, CA (US); Michael Clare, Skokie, IL (US)

(73) Assignee: Imago Biosciences, Inc., San Carlos, CA (US)

( * ) Notice: Subject to any disclaimer, the term of this patent is extended or adjusted under 35 U.S.C. 154(b) by 0 days.

(21) Appl. No.: 15/667,166

(22) Filed: Aug. 2, 2017

(65) Prior Publication Data

US 2017/0334873 A1 Nov. 23, 2017

Related U.S. Application Data

(63) Continuation of application No. 14/910,423, filed as application No. PCT/US2014/049906 on Aug. 6, 2014, now Pat. No. 9,790,195.

(60) Provisional application No. 61/954,276, filed on Mar. 17, 2014, provisional application No. 61/862,759, filed on Aug. 6, 2013.

(51) Int. Cl.
| | | |
|---|---|---|
| *C07D 295/192* | (2006.01) |
| *C07D 237/22* | (2006.01) |
| *C07D 213/81* | (2006.01) |
| *C07D 233/90* | (2006.01) |
| *C07D 295/185* | (2006.01) |
| *C07D 295/26* | (2006.01) |
| *C07D 215/14* | (2006.01) |
| *A61K 31/166* | (2006.01) |
| *A61K 31/40* | (2006.01) |
| *A61K 31/4453* | (2006.01) |
| *A61K 31/454* | (2006.01) |
| *A61K 31/4545* | (2006.01) |
| *A61K 31/47* | (2006.01) |
| *A61K 31/495* | (2006.01) |
| *A61K 31/5375* | (2006.01) |
| *A61K 31/54* | (2006.01) |
| *C07C 237/22* | (2006.01) |

(52) U.S. Cl.
CPC ........ *C07D 295/192* (2013.01); *A61K 31/166* (2013.01); *A61K 31/40* (2013.01); *A61K 31/4453* (2013.01); *A61K 31/454* (2013.01); *A61K 31/4545* (2013.01); *A61K 31/47* (2013.01); *A61K 31/495* (2013.01); *A61K 31/5375* (2013.01); *A61K 31/54* (2013.01); *C07C 237/22* (2013.01); *C07D 213/81* (2013.01); *C07D 215/14* (2013.01); *C07D 233/90* (2013.01); *C07D 295/185* (2013.01); *C07D 295/26* (2013.01); *C07C 2601/02* (2017.05)

(58) Field of Classification Search
CPC .. A61K 31/166; A61K 31/40; A61K 31/4453; A61K 31/454; A61K 31/4545; A61K 31/47; A61K 31/495; A61K 31/5375; A61K 31/54; C07C 237/22; C07C 2601/02; C07D 213/81; C07D 215/14; C07D 233/90; C07D 295/185; C07D 295/192; C07D 295/26
See application file for complete search history.

(56) References Cited

U.S. PATENT DOCUMENTS

| | | | |
|---|---|---|---|
| 9,790,195 | B2 | 10/2017 | McCall |
| 9,981,922 | B2 | 5/2018 | Rienhoff, Jr. |
| 2012/0108500 | A1 | 5/2012 | Sakane |
| 2013/0090386 | A1 | 4/2013 | Ortega |
| 2015/0225401 | A1 | 8/2015 | Wu |
| 2015/0232436 | A1 | 8/2015 | Baker |
| 2016/0130215 | A1 | 5/2016 | Tomita |
| 2016/0237043 | A1 | 8/2016 | Rienhoff |
| 2016/0257662 | A1 | 9/2016 | McCall |
| 2018/0312474 | A1 | 11/2018 | Rienhoff, Jr. |
| 2019/0070172 | A1 | 3/2019 | Rienhoff, Jr. |

FOREIGN PATENT DOCUMENTS

| | | |
|---|---|---|
| CN | 102947265 A | 2/2003 |
| EP | 2177502 A1 | 4/2010 |
| EP | 2927212 | 10/2015 |
| EP | 2927212 A1 | 10/2015 |
| WO | 2010043721 A1 | 4/2010 |
| WO | 2010143582 A1 | 12/2010 |
| WO | 2011035941 A1 | 3/2011 |

(Continued)

OTHER PUBLICATIONS

Ogasawara, et al., Lysine-specific demethylase 1-selective inactivators: Protein-targeted drug delivery mechanism, Angewandte Chemie, International Edition, 52(33), 8620-8624 (2013). (Year: 2013).*
International Search Report and Written Opinion for PCT Application No. PCT/US17/47208, filed on Aug. 16, 2017, 6 pages.
International Search Report and Written Opinion for PCT Application No. PCT/US16/17809, filed on Feb. 12, 2016, 55 pages.
International Preliminary Report on Patentability dated Aug. 24, 2017, for PCT Application No. PCT/US2016/017809, filed on Feb. 12, 2016, 7 pages.
International Search Report and Written Opinion for PCT Application No. PCT/US16/60847, dated Jan. 24, 2017, filed on Nov. 7, 2016, 14 pages.

(Continued)

*Primary Examiner* — Erich A Leeser
(74) *Attorney, Agent, or Firm* — Dennis A. Bennett; Cynthia Hathaway; John Desper

(57) ABSTRACT

Disclosed herein are new compounds and compositions and their application as pharmaceuticals for the treatment of diseases. Methods of inhibition of KDM1A, methods of increasing gamma globin gene expression, and methods to induce differentiation of cancer cells in a human or animal subject are also provided for the treatment of diseases such as acute myelogenous leukemia.

48 Claims, No Drawings

(56) References Cited

FOREIGN PATENT DOCUMENTS

| WO | 2011042217 | A1 | 4/2011 |
|---|---|---|---|
| WO | 2011131576 | A1 | 10/2011 |
| WO | 2011131697 | A1 | 10/2011 |
| WO | 2012013727 | A1 | 2/2012 |
| WO | 2012013728 | A1 | 2/2012 |
| WO | 2012034116 | A2 | 3/2012 |
| WO | 2012045883 | A1 | 4/2012 |
| WO | 2012047852 | | 4/2012 |
| WO | 2012071469 | A2 | 5/2012 |
| WO | 2012107498 | | 8/2012 |
| WO | 2012107498 | A1 | 8/2012 |
| WO | 2012107499 | A1 | 8/2012 |
| WO | 2012135113 | A2 | 10/2012 |
| WO | 2013057320 | A1 | 4/2013 |
| WO | 2013057322 | A1 | 4/2013 |
| WO | 2014084298 | | 6/2014 |
| WO | 2014084298 | A1 | 6/2014 |
| WO | 2014164867 | | 10/2014 |
| WO | 2014164867 | A1 | 10/2014 |
| WO | 2014164867 | A3 | 10/2014 |
| WO | 2015021128 | A1 | 2/2015 |
| WO | 2015021128 | A3 | 2/2015 |
| WO | 2016130952 | | 8/2016 |
| WO | 2016130952 | A1 | 8/2016 |
| WO | 2016130952 | A3 | 8/2016 |
| WO | 2017079753 | A1 | 5/2017 |
| WO | 2018035249 | | 2/2018 |
| WO | 2018035259 | | 2/2018 |

OTHER PUBLICATIONS

International Application No. PCT/US2014/023659; International Search Report and Written Opinion of the International Search Authority, dated Jul. 29, 2014; 9 pages.
International Application No. PCT/US2014/023659; International Search Report and Written Opinion of the International Search Authority, dated Jul. 29, 2014; 09 pages.
International Application No. PCT/US2014/049906; International Search Report and Written Opinion of the International Search Authority, dated Oct. 27, 2016; 08 pages.
International Application No. PCT/US2016/060847; International Preliminary Report on Patentability, dated May 17, 2018; 10 pages.
U.S. Appl. No. 14/910,423; Applicant Intiated Interview Summary dated Jun. 12, 2017; 02 pages.
U.S. Appl. No. 14/910,423; Final Office Action dated Apr. 18, 2017; 07 pages.
U.S. Appl. No. 14/910,423; Notice of Allowance dated Jun. 12, 2017; 04 pages.
U.S. Appl. No. 14/910,423; Notice of Allowance dated May 2, 2017; 07 pages.
U.S. Appl. No. 15/043,121; Examiner Intiated Interview Summary dated Jan. 12, 2018; 01 page.
U.S. Appl. No. 15/043,121; Examiner Intiated Interview Summary dated Sep. 18, 2017; 01 page.
U.S. Appl. No. 15/043,121; Non-Final Office Action dated May 19, 2017; 12 pages.
U.S. Appl. No. 15/043,121; Notice of Allowance dated Jan. 12, 2018; 07 pages.
U.S. Appl. No. 15/043,121; Notice of Allowance dated Sep. 18, 2017; 09 pages.
U.S. Appl. No. 15/773,911; U.S. Patent Application as filed dated May 4, 2018; 125 pages.
U.S. Appl. No. 15/952,073; U.S. Patent Application as filed dated Apr. 12, 2018; 296 pages.
U.S. Appl. No. 62/251,674, filed Nov. 5, 2015, Rienhoff.
U.S. Appl. No. 62/375,728, filed Jun. 16, 2016, Tapper.
Lizcano F et al, Epigenetic control and cancer: the potential of histone demethylases as therapeutic targets, Pharmaceuticals (Basel). Sep. 12, 2012; 5(9):963-90.
Sareddy GR et al., KDM1 is a novel therapeutic target for the treatment of gliomas, Oncotarget. Jan. 2013; 4(1):18-28.
Lerchner A et al., Macrocyclic BACE-1 inhibitors acutely reduce Abeta in brain after po application, Bioorg Med Chem Lett. Jan. 15, 2010; 20(2):603-607.
Benelkebir H et al., Enantioselective synthesis of tranylcypromine analogues as lysine-specific demethylase (LSD1) inhibitors, Bioorganic & Medicinal Chemistry 19 (Feb. 13, 2011) 3709-3716.
Binda C et al., Biochemical, Structural, and Biological Evaluation of Tranylcypromine Derivatives as Inhibitors of Histone Demethylases LSD1 and LSD2, J. Am. Chem. Soc. (Apr. 23, 2010) 132:19, 6827-6833.
Gooden, DM et al., Facile synthesis of substituted trans-2-arylcyclopropylamine inhibitors of the human histone demethylase LSD1 and monoamine oxidases A and B, Bioorg Med Chem Lett, (epub Jan. 8, 2008); 18(10):3047-51.
McCall John M., et al., KDM1A Inhibitors for the Treatment of Disease, IMAGO Biosciences Inc., US 20160257662 A1 Non-Final Rejection, dated Sep. 16, 2016.
Mccall, JM et al., KDM1A Inhibitors for the Treatment of Disease, IMAGO Biosciences Inc., WO 2014164867 A1—International Preliminary Report on Patentability Chapter 1, dated Sep. 15, 2015.
Mccall, JM et al., KDM1A Inhibitors for the Treatment of Disease, IMAGO Biosciences Inc., WO 2015021128 A1—International Preliminary Report on Patentability Chapter 1, dated Feb. 2, 2016.
Ogasawara, D et al., Synthesis and biological activity of optically active NCL-1, a lysine-specific demethylase 1 selective inhibitor, Bioorg Med Chem. Jun. 15, 2011; 19(12):3702-8. EpubDec. 22, 2010.
Ogasawara, et al., Lysine-specific demethylase 1-selective inactivators: Protein-targeted drug delivery mechanism, Angewandte Chemie, International Edition, 52(33), 8620-8624 (2013).
Wang J et al., Novel Histone Demethylase LSD1 Inhibitors Selectively Target Cancer Cells with Pluripotent Stem Cell Properties, (Epub Oct. 5, 2011), 71 (23):7238-49.
WO 2010143582 A1, Dec. 16, 2016 (Machine English translation).
Cardama, et al., "Therapy with the histone deacetylase inhibitor pracinostat for patients with myelofibrosis," Leuk Res. 2012, vol. 36(9), pp. 1124-1127. Title; abstract; p. 2, para 1; p. 3, para 1; p. 5, para 4 to p. 6, para 1.
Leoni F. et al., "The histone deacetylase inhibitor ITF2357 reduces production of pro-inflammatory cytokines in vitro and systemic inflammation in vivo", Mol Med. Jan.-Dec. 2005;11(1-12):1-15.
Alvarez-Larrán A et al. "Red cell mass measurement in patients with clinically suspected diagnosis of polycythemia vera or essential thrombocythemia", Haematologica. Nov. 2012;97(11):1704-7.
Kreipe H et al., "Clonal granulocytes and bone marrow cells in the cellular phase of agnogenic myeloid metaplasia", Blood. Oct. 1, 1991;78(7):1814-1847.
Zeppa P et al., "Fine-needle aspiration biopsy and flow cytometry immunophenotyping of lymphoid and myeloproliferative disorders of the spleen", Cancer, Apr. 25, 2003; 99(2): pp. 118-127.
Schnittger S et al., "FLT3 length mutations as marker for follow-up studies in acute myeloid leukaemia", Acta Haematol., 2004; 112(1-2): pp. 68-78.
Tefferi A et al., "Splenectomy in myelofibrosis with myeloid metaplasia: a single-institution experience with 223 patients", Blood. Apr. 1, 2000;95(7): pp. 2226-2233.
Mesa RA et al., "The Myelofibrosis Symptom Assessment Form (MFSAF): an evidence-based brief inventory to measure quality of life and symptomatic response to treatment in myelofibrosis", Leuk Res. Sep. 2009; 33(9): pp. 1199-1203.
Wolff, Manfred E., Burger's Medicinal Chemistry and Drug Discovery, Fifth Ed. vol. 1: Principles and Practice, John Wiley & Sons, 1995, 975-977.
Banker, Gilbert S. et al., Modem Pharmaceutics, Marcel Dekker, New York, 1996.
Morissette, S. et al., High-Throughput Crystallization: Polymorphs, Salts, Co-Crystals and Solvates of Pharmaceutical Solids, Adv Drug Delivery Rev, 56, 2004, 275-300.
Byrn, S. et al., Solid-State Chemistry of Drugs, 2nd Ed., Ch. 11 Hydrates and Solvates, 1999, 233-247.

(56) References Cited

OTHER PUBLICATIONS

Rouhi, Chem & Eng News, Science and Technology—The Right Stuff, 81(8), 2003, 32-35.
International Application No. PCT/US17/47192; International Search Report and Written Opinion of the International Search Authority, dated Jan. 9, 2018; 9 pages.
Kleepe M et al., Lysine-Specific Histone Demethylase, LSD1, (KDMIA) as a novel therapeutic target in myeloproliferative neoplasms, Blood 2015, 126:601, 7 pages.
The Cleveland Clinic, Myelofibrosis: Prevention. Web://my.clevelandclinic.org/health/diseases/15672-myelofibrosisprevention. (20015), 4 pages.
U.S. Appl. No. 15/952,073; Non-Final Office Action dated Sep. 6, 2018; 31 pages.
U.S. Appl. No. 16/326,495; Application as filed dated Feb. 19, 2019; 116 pages.
U.S. Appl. No. 16/326,498; Application as filed dated Feb. 19, 2019; 61 pages.

\* cited by examiner

KDM1A INHIBITORS FOR THE TREATMENT OF DISEASE

CROSS-REFERENCE TO RELATED APPLICATIONS

This application is a continuation of U.S. patent application Ser. No. 14/910,423, filed Feb. 5, 2016, which is a U.S. national stage filing under 35 U.S.C. § 371 of PCT International Application No. PCT/US2014/049906, filed Aug. 6, 2014, which claims the benefit of priority of U.S. Provisional Application Nos. 61/954,276, filed Mar. 17, 2014, and 61/862,759, filed Aug. 6, 2013, the disclosures of which are hereby incorporated by reference as if written herein in their entireties.

FIELD OF THE DISCLOSURE

The present disclosure relates to new compounds and compositions and their application as pharmaceuticals for the treatment of diseases.

DETAILED DESCRIPTION

Inhibiting the enzyme KDM1A (also known as lysine-specific demethylase 1, LSD1, Flavin-containing Amine Oxidase Domain-Containing Protein, AOF2, BRAF35-HDAC Complex Protein BHC110, FAD-Binding Protein BRAF35-HDAC Complex), may alter gene expression in cells sufficient to restore their proper physiologic function or that of the tissue, organ or the patient as a whole. This may be achieved either by enhancing transcription of a gene or genes that are pathologically silenced, e.g., as is the case in some cancer cells and heritable diseases, or decreasing transcription of a gene or genes participating in the pathological state. As such, inhibiting KDM1A would be useful for the treatment of diseases such as cancer and heritable diseases such as Wilson disease, cardiomyopathies, and hemoglobinopathies.

Gene expression is regulated through the recruitment of the RNA polymerase II transcription apparatus to the DNA template. The probability of this large multi-protein complex arriving near or at the start of DNA transcription and progressing through the entire coding region of a gene is determined in part by specific DNA sequences called promoters and enhancers, modifications of DNA sequence in the vicinity of the start of transcription, proteins bound to DNA and the topology of the DNA template itself. Factors enhancing the probability of RNA synthesis of protein-coding genes are known as transcription factors some of which participate in the transcription of all protein-coding genes and some of which are specific for the transcription of individual genes.

One major mechanism of transcription control consists of limiting the physical accessibility of the transcriptional regulatory regions to proteins that can activate or complete transcription; proteins bound to promoter or enhancer DNA sequences can occlude activating factors from binding to these DNA sequences resulting in fewer transcription initiations or extension of the activated progressing RNA polymerase complex. Likewise, topological constraints that do not allow the template DNA to unwind sufficiently to permit the steady progression of RNA polymerase on the template also serve to limit transcription rates.

The most important general factors influencing RNA synthesis using a DNA template in vivo are modifications of histones proteins that control among other factors the topology of the DNA template for transcription and its accessibility by the RNA polymerase complex. A small family of histone proteins—H2A, H2B, H3 and H4—combines to create a scaffold called the histone octamer upon which DNA is spatially and topologically organized into a regular repetitive structure called the nucleosome along the length of DNA. The conglomerate of histones, other proteins, various RNAs and DNA is called chromatin. Both DNA and histones are chemically modified in such a way as to attract and bind or repel other proteins with the effect of enhancing or repressing transcription.

The modification of DNA and associated RNAs and proteins that influence the regulation of transcription and replication that does not involve substitution of the canonical DNA bases is termed epigenetic. These epigenetic influences involve reversible chemical modifications of the four DNA bases themselves or post-translational chemical changes to the chromatin proteins and RNDs that associate with DNA. These epigenetic processes can play a pivotal role in activating or silencing the expression of a gene; in addition, the epigenetic modifications can be maintained for the life of an organism or can be dynamically modified in response to specific biochemical signals that originate either internally within the cell or extracellularly. These chromatin alterations can happen quickly or be very stable, e.g., during the hormonal induction of gene expression, chromatin structure at a specific locus can change radically within seconds to permit maximal transcription or chromatin structure can be modified to fully suppress gene expression, a state of chromatin which can be stably maintained over multiple cell divisions and even transgenerationally.

The methylation of cytosine at the 5' position is a common DNA base modification that is in turn recognized by a class of proteins most often associated with transcriptional repression. Similarly, histone proteins are chemically modified but with a wider variety of chemical adducts each of which either alone or in combination enhances or represses transcription of nearby genes. These histone modifications include, among others methylation, acetylation, sumoylation, phosphorylation, ubiquitylation, and myristoylation are recognized by other chromatin-associated proteins that in turn influence transcription rates and DNA replication. The dynamic state of gene expression and the associated chromatin states imply that histone modifications are not permanent but instead are added and removed according to the needs of the cell for specific gene products at specific times during ontogeny, adult life and the changing influences of the environment. Indeed, the specific chemical modifications of histones are each made by classes of enzymes acting at specific sites. These histone-modifying enzymes are in turn subject to tight regulation. These enzymes can potentially be targeted by compounds that inhibit their activity with the consequence of altering gene expression in a therapeutic manner.

Changes in the state of histone methylation are now known to play critical roles in normal regulation of the cell cycle and growth, the response to DNA damage and stress, and pre-natal development including differentiation. Pathological states such as cancer are associated with altered patterns of histone modifications and dysregulated histone-modifying proteins including chromatin-modifying enzymes. The need to closely regulate histone modifications is evidenced by the association of histone methylation status with human morbidity including ageing.

Histone methylation can occur on any of the three basic amino acid residues—lysine (K), arginine (R), and histidine (H). Methylation of histone H3 on lysines at positions 4

(H3K4), 9 (H3K9), 27 (H3K27), 36 (H3K36) and 79 (H3K79) are among the best studied of histone modifications that influence gene expression. Lysine tri-methylation (Kme3) on histone 3 (H3) at position 4 (H3K4me3) is a histone mark generally associated with activation of gene expression while H3K9me1 or H3K27me3 are associated with the repression of gene transcription. H3K4me1 is associated with DNA enhancers of gene transcription while H3K4me3 is associated with gene promoter activity. Likewise, loss of the methyl group at H3K4 is associated with repression of gene expression. Thus, the addition and removal of methyl groups at H3K4 constitutes a gene transcription switch. It is also evident that lysine can be modified with a mono-, di- or tri-methyl groups, each modification having a different biological effect through the attraction of different proteins recognizing those specific methylation modifications at that site.

A critical aspect of the regulation of the state of histone methylation is the recruitment of methyltransferases and demethylases to specific genetic loci. DNA sequence-specific binding proteins including transcription factors are one class of proteins responsible for this recruitment through the assemblage of protein complexes that bind these methyl-transferring enzymes. A well-studied example is the *Drosophila melanogaster* trithrorax group (TrxG) response elements (TREs) which recruit the H3K4 methyltransferase, TRX, to specific genes via transcription factors that recognize the TRE DNA sequence.

The histone methylation marks are recognized by methyl-binding domains in a diverse group of proteins; these domains include PHD fingers, WD40 and ankyrin repeats, CW and PWWP domains, and the Royal superfamily of proteins. These proteins, in turn, determine which additional activities are recruited into chromatin sites and ultimately the state of transcription at a given locus. Indeed, depending on which methyl-recognition protein binds the marked histone, the same methyl-lysine modification can have opposing effects on transcription. H3K4me2 and H3K4me3 are associated with transcriptional activation, but when bound by the PHD-domain-containing co-repressor protein Inhibitor of Growth family member 2 (ING2), an associated histone deacetylase complex is stabilized repressing gene expression. Thus, these effector proteins recognizing the methyl-lysine histone modifications significantly influence the level of transcriptional activity.

The ability to alter gene expression selectively by modifying the state of chromatin allows a novel therapeutic strategy to induce or de-repress the expression of genes that can provide a benefit, especially for genes whose expression has been suppressed by pathological mechanism as in the case of some cancers or suppressed by physiologic mechanism but who de-repression can phenotypically suppress mutations in paraologous genes with complementary function.

Many genes within a genome are members of gene families as a consequence of gene duplication. These genes are termed paralogs of one another. Following gene duplication, patterns of expression of two genes will evolve in a distinct manner in part to control the effects of gene dosage. Following gene duplication, random genetic drift arising from naturally occurring mutations and the subsequent selection of nucleotide sequence is commonly observed first in non-coding regions of duplicated genes, often in transcriptional regulatory regions. DNA changes in regulatory sequences can influence any or all aspects of gene expression: the magnitude of expression, its developmental timing, induction by stimuli outside the cell including hormonal or metabolic signals, and the cell type in which expression is restricted. In instances in which the duplication is recent in evolutionary time or where natural selection has maintained a high degree of protein-coding sequence similarity, the gene product of one paralog, gene A, can complement the pathological loss or silencing of the other paralog, gene B, if expression of gene A is not limiting in the same cell.

Altering patterns of gene expression may offer profound therapeutic benefits for genetic conditions in which enhanced expression of a paralogous gene "rescues" a phenotype caused by a mutation in a paralog. This might be called autologous gene complementation. In the case of Wilson disease caused by mutations in ATP7B, enhanced expression by pharmacologic induction of ATP7A, a closely related copper transporter protein, might rescue mutations in ATP7B, another copper transporter. The basic function of each copper transporter protein has been preserved but following the duplication of the common ancestral gene, the expression of these two genes has been separated spatially, one confined to intestinal enterocytes, the other to hepatocytes. This is one of many examples of paralogous gene in which one gene can complement the loss of the second if appropriately expressed in the same cell or tissue.

A notable example of a paralogous gene family is the well-studied alpha and beta family of globin genes coding for the alpha and beta subunits of hemoglobin. Five beta-like genes each arising by gene duplication are arrayed next to each other on chromosome 16 with each gene being transcribed in a temporally-specific manner throughout the 9 months of human embryonic and fetal development. The five beta-like globin proteins share a high degree of protein sequence similarity, so much so that genetic mutations inactivating the adult beta globin gene can be clinically silent if expression of any one of the other 4 subunit members of the beta-like globin family is adequate. Activation of expression and subsequent transcriptional silencing of each specific embryonic and fetal beta-like globin gene is regulated in part by epigenetic mechanisms. The rescue of mutations in the beta globin gene, mutations which are responsible for diseases such as thalassemia major or sickle cell anemia, by transcriptional induction of one or more of the other beta-like genes through the pharmacologic manipulation of epigenetic silencing would be clinically beneficial. Autologous activation with a pharmacologic agent of a functionally complementary paralog of a mutated or pathologically silenced gene may be a more successful therapeutic strategy than replacing or repairing the mutated gene with a wild-type (normal) copy.

Interest in influencing the activity of histone modifications for therapeutic effect derive from observations that the expression of specific genes under epigenetic control could be altered by altering epigenetic marks such as methylation. In the case of cancer, loss of specific histone methylation marks concomitant with overexpression of histone demethylases is associated with the recurrence of those cancers with attendant poorer outcomes. These studies suggest that specific tumor suppressor genes are silenced by loss of methylation modifications that in turn enhance the survival and growth potential of neoplastic cells. This had led to the proposition that inhibition of histone demethylase activity might have therapeutic value.

KDM1A (also known as Lysine-Specific Demethylase 1 (LSD1) or AOF2 or BHC110) was the first enzyme with specific lysine demethylase activity to be described demonstrating unequivocally that histone modifications are reversible rather than permanent. Among its demethylase substrates, KDM1A is a histone H3 lysine demethylase that catalyzes the oxidative demethylation of H3K4me1 or me2 and H3K9me1 or me2 but not the substrate H3K4me3. The enzyme also demethylates non-histone proteins such as p53 and Gfi1. KDM1A contains an amine oxidase domain that demethylates H3Kme substrate in a flavin adenine dinucleotide (FAD)-dependent manner similar to other monoamine (MAO) and polyamine oxidase inhibitors. Indeed, non-specific inhibitors of MAO enzymes can inhibit the demethylase activity of KDM1A KDM1A is over-expressed in many human cancers including Wilms tumor, small-cell lung, bladder, prostate, breast, head & neck, colon, and ovarian cancer and associated with more frequent relapses. KDM1A is required for transcriptional regulation mediated by the androgen receptor in prostate cancer, the estrogen receptor in breast carcinomas, and the TLX receptor in neuroblastoma. Knockdown of KDM1A expression decreases proliferation of cancer cells. KDM1A is also overexpressed in cancer cells that are nuclear hormone receptor-independent including ER-negative breast. Potent, selective small molecule inhibitors of KDM1A should be useful for treatment of these and other cancers in which KDM1A activity is overabundant.

The structure and state of chromatin can also influence the ability of a pathogenic virus to insert into host DNA, undergo transcription and replicate. Infection by the alpha herpes viruses herpes simplex virus (HSV) and varicella-zoster virus (VSV) effect the remodeling of chromatin after infection of host cells to counter the rapid deposition of nucleosomes containing histones with transcriptional repressive marks by employing virus-encoded transcription factors to recruit the host HCF-1 co-activator complex that contains KDM1A and the histone H3K4 methyltransferases Set1 or MLL family members. It has been demonstrated that inhibition of KDM1A in cells infected with HSV1 inhibits HSV IE gene expression, suppresses lytic infection and reduces viral loads. Similarly, inhibiting KDM1A causes a decrease in the expression of the immediate early genes in cells infected with human cytomegalovirus and adenovirus suggesting a broader role for KDM1A in viral pathogenesis.

The influence KDM1A activity has on the transcription of specific genes is dependent on recruitment of KDM1A to a specific gene promoter region via DNA binding proteins. In the case of androgen-dependent gene expression, KDM1A associates with the androgen steroid receptor which specifically targets DNA binding sites in the promoters of androgen-responsive genes. Thus, proteins that bind KDM1A determine where along the chromosome the demethylase activity is targeted. Many proteins have been reported to interact with KDM1A including the CoREST, CtBP, NuRD, BRAF35 complexes, DNMT1, MTA1/2, Mi2beta, RbAp46/48, HDAC1, 2, and 3, TIF1beta, Blimp-1, ZNF217 and ZNF198, a subset of which form larger and in some cases complexes that mutually exclude one another. The KDM1A/CoREST complex which may also include DNMT1 and NuRD among other factors is particularly important for the repression of expression of specific genes.

KDM1A is recruited to the promoter region of genes through site-specific transcription factors. Such factors include among others the androgen receptor, the estrogen receptor alpha, Snail1, Slug, HIV Tat, ZEB1, RBP-J, PIT1, REST, NR2C1, NR2C2 and isoforms of Gfi1b. These transcription factors can recruit KDM1A to participate in activation of gene expression or silencing of gene expression depending on the cell type and the specific transcription factors.

Many of the enzyme activities that regulate the state of chromatin are influenced allosterically or require as co-factors metabolic intermediates, mediators or end-products of cell metabolism. These intermolecular relationships between gene expression and metabolism provide cells with signaling pathways connecting the external and internal cellular environment including nutrients with mechanisms modulating gene expression. This cellular sensing can alter both short and long term adjustments to gene expression patterns constituting an epigenetic memory of historical metabolic states and environmental conditions. For example, beta-hydroxybutyrate, a product of long chain fatty acid metabolism and a major source of energy for mammals during starvation or prolonged exertion, inhibits class I histone deacetylases (HDAC) but not class 2b HDAC. Thus the effects of starvation and nutrient loss can be epigenetically coded and preserved. Acetyl-coenzyme A, nicotinamide adenine dinucleotide (NAD) and alpha-ketoglutarate also influence histone methylation and acetylation states.

Flavin adenine dinucleotide (FAD) is a required co-factor for KDM1A. FAD, in conjunction with NAD and NADP act as cellular redox sensors. KDM1A temporarily converts FAD to FADH after which an electron acceptor, likely $O_2$ and others, completes the catalytic cycle by regenerating FAD and $H_2O_2$. Thus, the cellular redox state influences KDM1A activity both by its ability to oxidize FADH and other electron acceptors. In a general sense, chromatin states, hence gene expression, can be altered by the variable concentrations of metabolic intermediates and in the specific case of KDM1A that activity is entirely dependent on FAD whose concentration fluctuates as a function of the energetic economy of the cell. In addition, it has been shown that inhibition of KDM1A can lower serum glucose, reduced hepatic glycogen, and is a powerful insulin secretogogue. Pharmaceutical manipulation of KDM1A activity may thus prove useful for the treatment of diseases that represent pathological aberrations of the energy status of the cell including metabolic syndrome, dyslipidemias, diabetes, obesity, anorexia, failure to thrive, cachexia, lipodystrophies, and steatohepatitis.

The steroid hormones estradiol and testosterone and related compound play a key role in both normal development and in pathological states such as breast and prostate cancer in which tumor cell growth is dependent on hormonal signaling. The biological effects of steroid hormones are mediated by structurally and functionally distinct ligand-binding receptors that function as a transcription factor recruited to a specific DNA binding site. The ligand-bound steroid receptors act as the principal transcriptional regulator of hormone effects. Transcriptional activation of gene expression for all steroid-dependent hormones is dependent on chromatin structure and the presence of co-factors. The estrogen receptor employs, for example, the co-factors SRC1, SRC2, AIB1, PELP1, CBP, p300, PCAF, CARM1, PRMT1 and co-repressors such as NCoR, SMRT and MTA1. The transcriptional response to hormone stimulation is dependent on the interaction of these co-factors and repressors as well as the state of chromatin, especially modification of histones by histone-modifying enzymes associated with the co-regulators. Both estrogenic and androgenic hormone stimulation induces several histone modifications at the promoters of target genes that alter the acetylation, phosphorylation and methylation state of local histones. To affect the maximal rate of transcription for a hormone-responsive gene, KDM1A activity is required. Thus, KDMA1 should prove useful as a therapeutic target of pharmaceuticals in blunting or ablating the hormone-dependence of tumor cells. This same therapeutic logic applies to other ligand-dependent transcription factors whose transcriptional activation is partly or wholly dependent on KDM1A activity to alter chromatin states sufficiently to facilitate transcription—examples of these would include the vitamin D, retinoid and lipid-activated receptors.

Numerous therapeutic agents have been identified that have the effect of altering gene expression acting either directly on proteins, generally enzymes, that alter chromatin states or indirectly. Though the precise mechanisms of their action have not all been fully elucidated, those mechanism can be inferred from our understanding of the protein complexes that participate in the activation of specific gene expression. These agents include 5'-azacytadine and 5'-aza-2' deoxycytidine (decitabine) which inhibit DNMT1 or other DNA methyltransferases known to be present and active at promoter sites of silenced genes such as gamma globin promoter; vorinostat and panobinostat or other inhibitors of histone deacetylase (HDAC) enzymes; hydroxyurea (HU), valproate and sodium butyrate and its analogues each of which may interfere with the activity of orphan nuclear receptors. All of these agents enjoy some clinical use principally in the management of neoplastic disease. Though some clinical utility of these agents for other disease states has been demonstrated, these agents have not been widely adopted because of their modest therapeutic effects and their toxicity.

The use of agents that inhibit any enzymatic activity resident in the protein complex bound to gene promoter has the potential to disrupt the repression of gamma globin gene expression and result in increased levels of fetal hemoglobin also known as hemoglobin F (HbF). Such targets include any of the interfaces of the specific protein-protein contacts, for example, the NuRD complex and KDM1A; the DNA binding recognition domains of, for example, NR2C1 and NR2C2; the ligand binding domains of, for example, NR2C1 and NR2C2; the enzyme activities such as lysine demethylase, for example, KDM1A; histone deacetylases (HDAC), for example HDAC1, 2, or 3; DNA methyltransferases, for example, DNMT1.

There remains a need for compositions and methods for altering gene expression in cells and tissues sufficient to restore the cell or tissue to normal physiologic function including, e.g., appropriate apoptosis in the case of cancer, or to alter the pathological phenotype of the cell, tissue, organ or organism by inducing the expression of one or more genes sufficiently to suppress the pathological state.

Accordingly, the inventors herein disclose new compounds, compositions and methods for treating diseases associated with KDM1A activity.

Certain embodiments of the invention provide compounds of the formula (I):

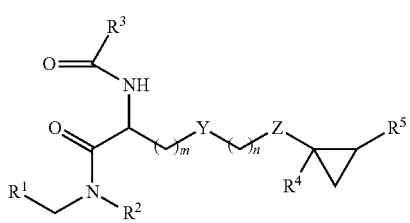

(I)

or a salt thereof, wherein:
Y is chosen from a bond, $NR^{4a}$, O, C(O)NH, NHC(O), S, $SO_2$, and $CH_2$;
Z is chosen from a bond, $NR^{4b}$, O, C(O)NH, NHC(O), S, $SO_2$, and $CH_2$;
m is an integer from 0 to 5;
n is an integer from 0 to 3;
$R^1$ and $R^2$ are each independently chosen from, alkyl, aminoalkyl, alkylsulfonylalkyl, alkoxyalkyl, aryl, arylalkyl, cycloalkyl, cycloalkylalkyl, phenyl, biphenyl, heteroaryl, heteroarylalkyl, heterocycloalkyl, and heterocycloalkylalkyl and $R^1$ and $R^2$, together with the nitrogen to which they attach, form a nitrogen-containing heterocycloalkyl or heteroaryl ring, which may be optionally substituted with between 0 and 3 $R^6$ groups;
$R^3$ is chosen from alkylamino, cycloalkylamino, arylamino, heteroarylamino, heterocycloalkylamino, cycloalkyl, cycloalkylalkyl, aryl, arylalkyl, heteroaryl, heteroarylalkyl, heterocycloalkyl, and heterocycloalkylalkyl any of which may be optionally substituted with between 0 and 3 $R^6$ groups;
$R^4$, $R^{4a}$, and $R^{4b}$ are independently chosen from hydrogen, alkyl, alkenyl, alkynyl, and cycloalkyl;
$R^5$ is chosen from aryl and heteroaryl, any of which may be optionally substituted with between 0 and 3 $R^6$ groups;
each $R^6$ is independently chosen from hydrogen, halogen, alkyl, alkenyl, alkynyl, cycloalkyl, haloalkyl, haloalkoxy, aryl, aralkyl, heterocycloalkyl, heteroaryl, heteroarylalkyl, cyano, alkoxy, amino, alkylamino, dialkylamino, $COR^7$, $SO_2R^7$, $NHSO_2R^7$, $NHSO_2NHR^7$, $NHCOR^7$, $NHCONHR^7$, $CONHR^7$, and $CONR^7R^8$; and
$R^7$ and $R^8$ are independently chosen from hydrogen, and lower alkyl; or $R^7$ and $R^8$ may be taken together to form a nitrogen-containing heterocycloalkyl or heteroaryl ring, which may be optionally substituted with lower alkyl.

In some embodiments, the compound has Formula IIa or IIb:

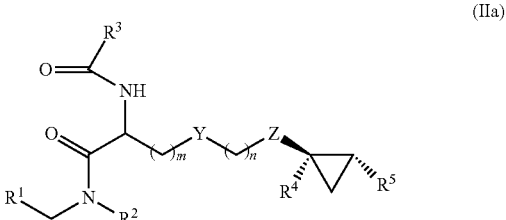

(IIa)

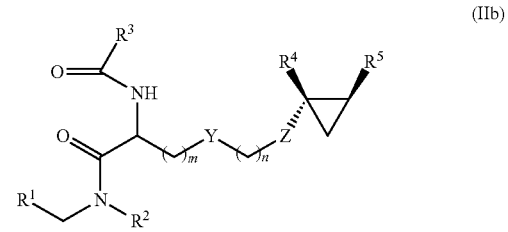

(IIb)

or a salt thereof, wherein:
Y is chosen from a bond, $NR^{4a}$, O, C(O)NH, NHC(O), S, $SO_2$, and $CH_2$;
Z is chosen from a bond, $NR^{4b}$, O, C(O)NH, NHC(O), S, $SO_2$, and $CH_2$;
m is an integer from 0 to 5;
n is an integer from 0 to 3;
$R^1$ and $R^2$ are each independently chosen from, alkyl, aminoalkyl, alkylsulfonylalkyl, alkoxyalkyl, aryl, arylalkyl, cycloalkyl, cycloalkylalkyl, phenyl, biphenyl, heteroaryl, heteroarylalkyl, heterocycloalkyl, and heterocycloalkylalkyl and $R^1$ and $R^2$, together with the nitrogen to which they attach, form a nitrogen-containing heterocycloalkyl or heteroaryl ring, which may be optionally substituted with between 0 and 3 $R^6$ groups;

$R^3$ is chosen from alkylamino, cycloalkylamino, arylamino, heteroarylamino, heterocycloalkylamino, cycloalkyl, cycloalkylalkyl, aryl, arylalkyl, heteroaryl, heteroarylalkyl, heterocycloalkyl, and heterocycloalkylalkyl any of which may be optionally substituted with between 0 and 3 $R^6$ groups;

$R^4$, $R^{4a}$, and $R^{4b}$ are independently chosen from hydrogen, alkyl, alkenyl, alkynyl, and cycloalkyl;

$R^5$ is chosen from aryl and heteroaryl, any of which may be optionally substituted with between 0 and 3 $R^6$ groups;

each $R^6$ is independently chosen from hydrogen, halogen, alkyl, alkenyl, alkynyl, cycloalkyl, haloalkyl, haloalkoxy, aryl, aralkyl, heterocycloalkyl, heteroaryl, heteroarylalkyl, cyano, alkoxy, amino, alkylamino, dialkylamino, $COR^7$, $SO_2R^7$, $NHSO_2R^7$, $NHSO_2NHR^7$, $NHCOR^7$, $NHCONHR^7$, $CONHR^7$, and $CONR^7R^8$; and $R^7$ and $R^8$ are independently chosen from hydrogen, and lower alkyl; or $R^7$ and $R^8$ may be taken together to form a nitrogen-containing heterocycloalkyl or heteroaryl ring, which may be optionally substituted with lower alkyl.

In some embodiments, the compound has Formula IIa or IIIb:

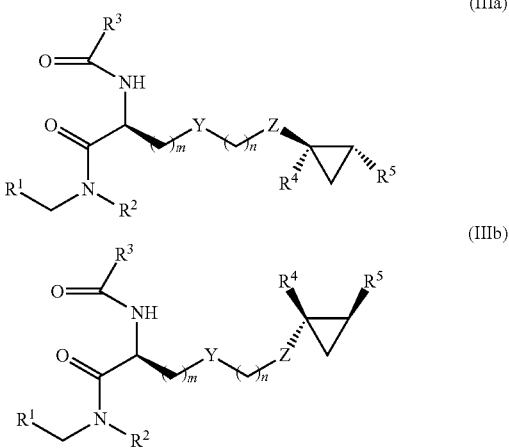

(IIIa)

(IIIb)

or a salt thereof, wherein:

Y is chosen from a bond, $NR^{4a}$, O, C(O)NH, NHC(O), S, $SO_2$, and $CH_2$;

Z is chosen from a bond, $NR^{4b}$, O, C(O)NH, NHC(O), S, $SO_2$, and $CH_2$;

m is an integer from 0 to 5;

n is an integer from 0 to 3;

$R^1$ and $R^2$ are each independently chosen from, alkyl, aminoalkyl, alkylsulfonylalkyl, alkoxyalkyl, aryl, arylalkyl, cycloalkyl, cycloalkylalkyl, phenyl, biphenyl, heteroaryl, heteroarylalkyl, heterocycloalkyl, and heterocycloalkylalkyl and $R^1$ and $R^2$, together with the nitrogen to which they attach, form a nitrogen-containing heterocycloalkyl or heteroaryl ring, which may be optionally substituted with between 0 and 3 $R^6$ groups;

$R^3$ is chosen from alkylamino, cycloalkylamino, arylamino, heteroarylamino, heterocycloalkylamino, cycloalkyl, cycloalkylalkyl, aryl, arylalkyl, heteroaryl, heteroarylalkyl, heterocycloalkyl, and heterocycloalkylalkyl any of which may be optionally substituted with between 0 and 3 $R^6$ groups;

$R^4$, $R^{4a}$, and $R^{4b}$ are independently chosen from hydrogen, alkyl, alkenyl, alkynyl, and cycloalkyl;

$R^5$ is chosen from aryl and heteroaryl, any of which may be optionally substituted with between 0 and 3 $R^6$ groups;

each $R^6$ is independently chosen from hydrogen, halogen, alkyl, alkenyl, alkynyl, cycloalkyl, haloalkyl, haloalkoxy, aryl, aralkyl, heterocycloalkyl, heteroaryl, heteroarylalkyl, cyano, alkoxy, amino, alkylamino, dialkylamino, $COR^7$, $SO_2R^7$, $NHSO_2R^7$, $NHSO_2NHR^7$, $NHCOR^7$, $NHCONHR^7$, $CONHR^7$, and $CONR^7R^8$; and $R^7$ and $R^8$ are independently chosen from hydrogen, and lower alkyl; or $R^7$ and $R^8$ may be taken together to form a nitrogen-containing heterocycloalkyl or heteroaryl ring, which may be optionally substituted with lower alkyl.

In certain embodiments, Z is $NR^{4b}$.

In certain embodiments, $R^{4b}$ is chosen from methyl and hydrogen.

In certain embodiments, the alkyl, whether by itself or as a named part of another non-cyclic substituent, is $C_1$-$C_8$ alkyl.

In certain embodiments, $R^3$ is chosen from aryl, arylalkyl, heteroaryl, and heteroarylalkyl, any of which may be optionally substituted with between 0 and 3 $R^6$ groups.

In certain embodiments, $R^3$ is chosen from aryl and heteroaryl, any of which may be optionally substituted with between 0 and 3 $R^6$ groups.

In certain embodiments, m is an integer from 0 to 1; Y is chosen from $NR^{4a}$, O, S, $SO_2$, and $CH_2$; n is an integer from 1 to 3; and $R^{4a}$ is chosen from hydrogen and alkyl.

In certain embodiments, m is 0; Y is $CH_2$; and n is an integer from 1 to 3.

In certain embodiments, n is 1. In certain embodiments, n is 2. In certain embodiments, n is 3.

In certain embodiments, $R^3$ is 5-6 membered monocyclic or 8-12 membered bicyclic heteroaryl, in which between one and five ring members may be heteroatoms chosen from N, O, and S, and which may be optionally substituted with between 0 and 3 $R^6$ groups.

In certain embodiments, $R^3$ is 5-6 membered monocyclic heteroaryl, in which between one and four ring members may be heteroatoms chosen from N, O, and S, and which may be optionally substituted with between 0 and 3 $R^6$ groups.

In certain embodiments, each $R^6$ is chosen from lower alkyl, halogen, lower alkoxy, $OCF_3$ and $CF_3$.

In certain embodiments, $R^3$ is chosen from

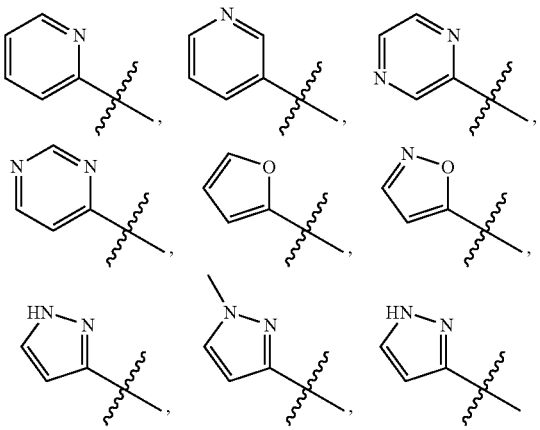

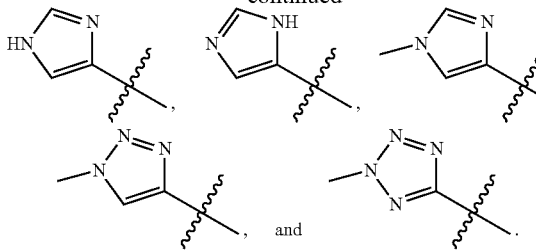

, and

In certain embodiments, $R^4$ is hydrogen.

In certain embodiments, $R^4$ is methyl.

In certain embodiments, the nitrogen-containing heterocycloalkyl or heteroaryl ring formed by $R^1$ and $R^2$ together with the nitrogen to which they are attached contains 3 to eight atoms.

In certain embodiments, $R^1$ and $R^2$ are taken together to form a nitrogen-containing heterocycloalkyl, which may be optionally substituted with between 0 and 3 $R^6$ groups.

In certain embodiments, the nitrogen-containing heterocycloalkyl formed by $R^1$ and $R^2$ together with the nitrogen to which they are attached is chosen from:

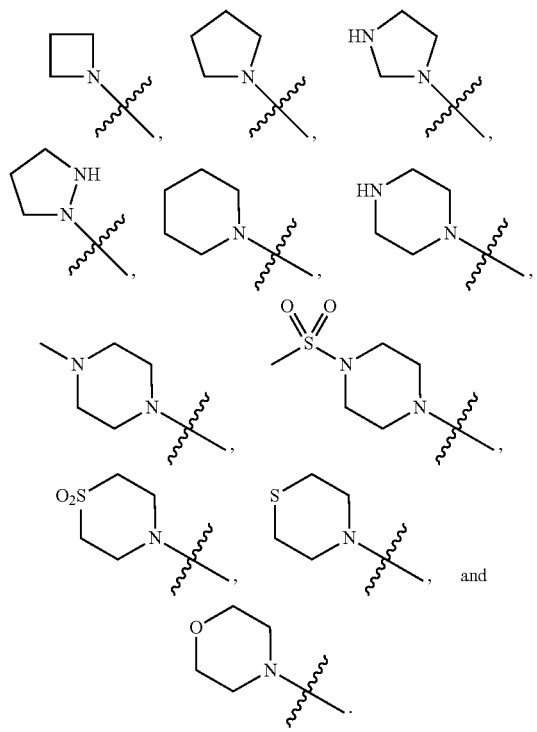

In certain embodiments, the nitrogen-containing heterocycloalkyl formed by $R^1$ and $R^2$ together with the nitrogen to which they are attached is chosen from:

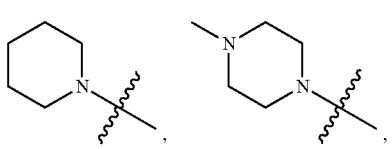

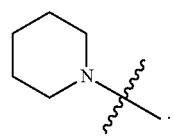 [SMILES: *N1CCCCC1]

, and

In certain embodiments, the nitrogen-containing heterocycloalkyl formed by $R^1$ and $R^2$ together with the nitrogen to which they are attached is

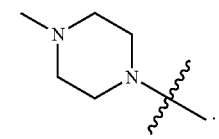 [SMILES: *N1CCN(C)CC1]

In certain embodiments, the nitrogen-containing heterocycloalkyl formed by $R^1$ and $R^2$ together with the nitrogen to which they are attached is

.

In certain embodiments, the nitrogen-containing heterocycloalkyl formed by $R^1$ and $R^2$ together with the nitrogen to which they are attached is

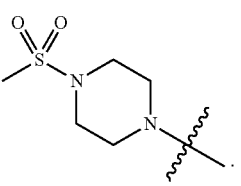 [SMILES: *N1CCN(S(C)(=O)=O)CC1]

In certain embodiments, the nitrogen-containing heterocycloalkyl formed by $R^1$ and $R^2$ together with the nitrogen to which they are attached is

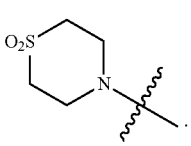

In certain embodiments, the nitrogen-containing heterocycloalkyl formed by $R^1$ and $R^2$ together with the nitrogen to which they are attached is

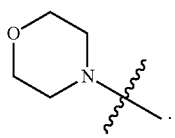 [SMILES: *N1CCOCC1]

In certain embodiments, n is 2 or 3.

In certain embodiments, $R^1$ and $R^2$ are taken together with the nitrogen to which they are attached form a nitrogen-containing heteroaryl, which may be optionally substituted with between 0 and 3 $R^6$ groups.

In certain embodiments, the nitrogen-containing heteroaryl is chosen from pyrrole, imidazole, and pyrazole.

In certain embodiments, $R^5$ is aryl, which may be optionally substituted with between 0 and 3 $R^6$ groups.

In certain embodiments, $R^5$ is phenyl, which may be optionally substituted with between 0 and 3 $R^6$ groups.

In certain embodiments, n is 2 or 3.

In certain embodiments, $R^5$ is heteroaryl, which may be optionally substituted with between 0 and 3 $R^6$ groups.

In certain embodiments, $R^5$ is a 5-6 membered monocyclic or 8-12 membered bicyclic heteroaryl, in which between one and five ring members may be heteroatoms chosen from N, O, and S, and which may be optionally substituted with between 0 and 3 $R^6$ groups.

In certain embodiments, $R^5$ is a 5-6 membered monocyclic heteroaryl, in which between one and five ring members may be heteroatoms chosen from N, O, and S, and which may be optionally substituted with 1 or 2 $R^6$ groups.

In certain embodiments, $R^5$ is chosen from:

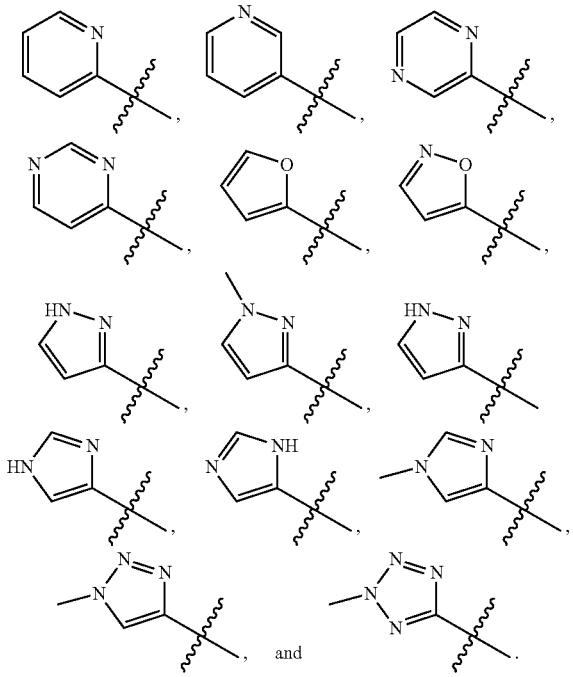

and

In certain embodiments, n is 2 or 3.

In certain embodiments, $R^3$ is aryl, optionally substituted with between 0 and 3 $R^6$ groups.

In certain embodiments, $R^3$ is chosen from phenyl and biphenyl, either of which may be optionally substituted with between 0 and 3 $R^6$ groups.

In certain embodiments,
m is an integer from 0 to 1;
Y is chosen from $NR^{4a}$, O, S, $SO_2$, and $CH_2$;
n is an integer from 1 to 3; and
$R^{4a}$ is chosen from hydrogen and alkyl.

In certain embodiments,
m is 0;
Y is $CH_2$; and
n is an integer from 1 to 3.

In certain embodiments, n is 1. In certain embodiments, n is 2. In certain embodiments, n is 3.

In certain embodiments, $R^6$ is chosen from lower alkyl, halogen, lower alkoxy, $OCF_3$ and $CF_3$.

In certain embodiments, $R^4$ is hydrogen.

In certain embodiments, $R^4$ is methyl.

In certain embodiments, n is 2 or 3.

In certain embodiments, the nitrogen-containing heterocycloalkyl or heteroaryl ring formed by $R^1$ and $R^2$ together with the nitrogen to which they are attached contains 3 to eight atoms.

In certain embodiments, $R^1$ and $R^2$ are taken together to form a nitrogen-containing heterocycloalkyl, which may be optionally substituted with between 0 and 3 $R^6$ groups.

In certain embodiments, the nitrogen-containing heterocycloalkyl formed by $R^1$ and $R^2$ together with the nitrogen to which they are attached is chosen from:

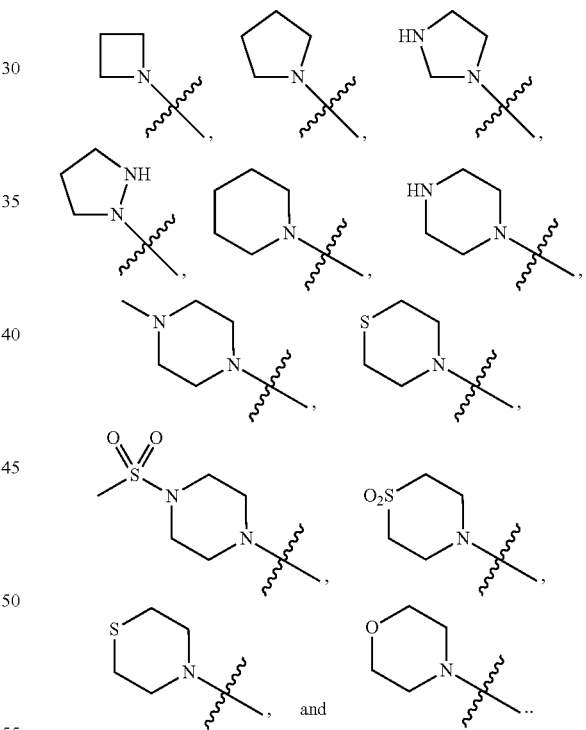

, and

In certain embodiments, the nitrogen-containing heterocycloalkyl formed by $R^1$ and $R^2$ together with the nitrogen to which they are attached is chosen from:

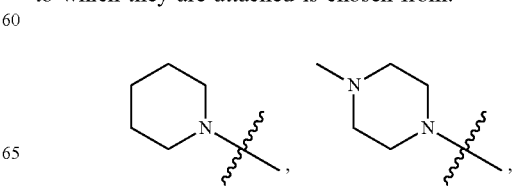

-continued

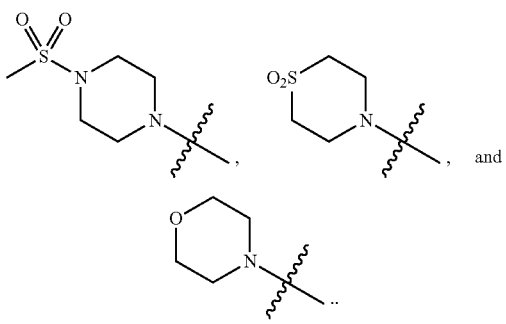

In certain embodiments, the nitrogen-containing heterocycloalkyl formed by $R^1$ and $R^2$ together with the nitrogen to which they are attached is

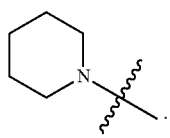 [SMILES: *N1CCCCC1]

In certain embodiments, the nitrogen-containing heterocycloalkyl formed by $R^1$ and $R^2$ together with the nitrogen to which they are attached is

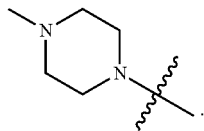 [SMILES: *N1CCN(C)CC1]

In certain embodiments, the nitrogen-containing heterocycloalkyl formed by $R^1$ and $R^2$ together with the nitrogen to which they are attached is

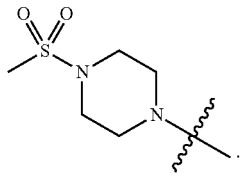 [SMILES: *N1CCN(S(C)(=O)=O)CC1]

In certain embodiments, the nitrogen-containing heterocycloalkyl formed by $R^1$ and $R^2$ together with the nitrogen to which they are attached is

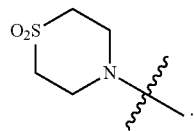

In certain embodiments, the nitrogen-containing heterocycloalkyl formed by $R^1$ and $R^2$ together with the nitrogen to which they are attached is

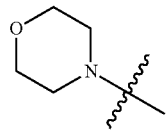

In certain embodiments, n is 2 or 3.

In certain embodiments, $R^1$ and $R^2$ taken together form a nitrogen-containing heteroaryl, which may be optionally substituted with between 0 and 3 $R^6$ groups.

In certain embodiments, the nitrogen-containing heteroaryl is chosen from pyrrole, imidazole, and pyrazole.

In certain embodiments, $R^5$ is aryl, which may be optionally substituted with between 0 and 3 $R^6$ groups, each of which is independently chosen from lower alkyl, halogen, lower alkoxy, $OCF_3$ and $CF_3$.

In certain embodiments, $R^5$ is phenyl, which may be optionally substituted with between 0 and 3 $R^6$ groups, each of which is independently chosen from lower alkyl, halogen, lower alkoxy, $OCF_3$ and $CF_3$.

In certain embodiments, n is 2 or 3.

In certain embodiments, $R^5$ is heteroaryl, which may be optionally substituted with between 0 and 3 $R^6$ groups.

In certain embodiments, $R^5$ is a 5-6 membered monocyclic or 8-12 membered bicyclic heteroaryl, in which between one and five ring members may be heteroatoms chosen from N, O, and S, and which may be optionally substituted with between 0 and 3 $R^6$ groups, each of which is independently chosen from lower alkyl, halogen, lower alkoxy, $OCF_3$ and $CF_3$.

In certain embodiments, $R^5$ is a 5-6 membered monocyclic heteroaryl, in which between one and five ring members may be heteroatoms chosen from N, O, and S, and which may be optionally substituted with 1 or 2 $R^6$ groups, each of which is independently, if present, a lower alkyl groups.

In certain embodiments, $R^5$ is chosen from:

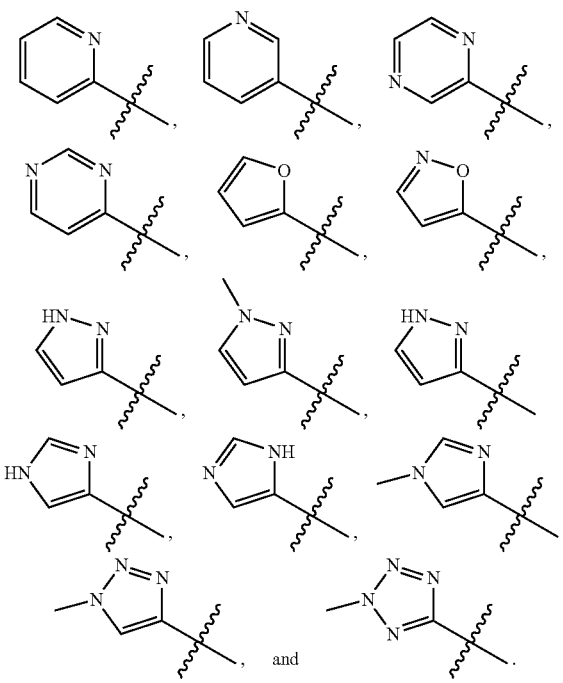

In certain embodiments, wherein n is 2 or 3.

Also provided are embodiments wherein any embodiment above may be combined with any one or more of these embodiments, provided the combination is not mutually exclusive. As used herein, two embodiments are "mutually exclusive" when one is defined to be something which cannot overlap with the other. For example, an embodiment wherein Y is $CH_2$ is mutually exclusive with an embodiment wherein Y is $NW^{4b}$. However, an embodiment wherein $R^1$ and $R^2$ are taken together to form a nitrogen-containing heterocycloalkyl is not mutually exclusive with an embodiment wherein $R^5$ is phenyl optionally substituted with fluorine.

In accordance with another aspect of the invention, a compound as disclosed herein is provided for use as a medicament.

In accordance with another aspect of the invention, a compound as disclosed herein is provided for use in the manufacture of a medicament for the prevention or treatment of a disease or condition chosen from sickle cell disease, thalassemia major, and other beta-hemoglobinopathies.

In accordance with another aspect of the invention, a pharmaceutical composition is provided which comprises a compound as disclosed herein, together with a pharmaceutically acceptable carrier.

In some embodiments, the pharmaceutical composition is formulated for oral administration.

In some embodiments, the pharmaceutical composition additionally comprises another therapeutic agent.

In accordance with another aspect of the invention, a method of inhibiting KDM1A is provided, comprising contacting KDM1A with a compound as disclosed herein.

In accordance with another aspect of the invention, a method of treating a globin-mediated disease is provided; comprising the administration of a therapeutically effective amount of a compound as disclosed herein.

In some embodiments, the disease is chosen from Myelodysplastic Syndrome (MDS), Acute Myelogenous Leukemia (AML), and Chronic Myelogenous Leukemia (CML).

In accordance with another aspect of the invention, a method for achieving an effect in a patient is provided; comprising the administration of a therapeutically effective amount of a compound as disclosed herein; wherein the effect is chosen from an elevation of red blood cell count, an elevation of the red blood cell count of red cells containing fetal hemoglobin, an elevation in the total concentration of fetal hemoglobin in red cells, an elevation in the total concentration of fetal hemoglobin in reticulocytes, an increase in the transcription of the gamma globin gene in bone marrow-derived red cell precursors, e.g., pro-erythroblasts, a reduction in the number of sickle cell crises a patient experiences over a unit period of time, a halt to or prevention of tissue damage e.g. in the heart, spleen, brain or kidney caused by sickling cells, a reduction in the proportion of red cells that undergo sickling under physiological conditions of relative hypoxia as measured using patient blood in an in vitro assay, an increase in the amount of histone 3 lysine methylation at lysine position 4 (H3K4me1 and H3K4me2), and/or a decrease in the amount of histone 3 methylation at lysine position 9 (H3K9me1 or H3K4me2) near or at the gamma globin promoter as assayed by ChIP using cells derived from a treated patient.

In accordance with another aspect of the invention, a method of inhibiting at least one KDM1A function is provided; comprising the step of contacting KDM1A with a compound as disclosed herein; wherein the inhibition is measured by phenotype of red cells or their precursors either cultured or in vivo in humans or mouse or transgenic mice containing the human beta globin locus or portions thereof, the ability of cancer cells to proliferate, the expression of specific genes known to be regulated by KDM1A activity such as gamma globin, a change in the histone methylation states, a change in the methylation state of proteins known to be demethylated by KDM1A such as G9a or SUV39H1, expression of KDM1A-regulated genes, or binding of KDM1A with a natural binding partner such as CoREST, DNMT1 or HDACs.

Inhibition of LSD1 activity alone may be sufficient therapy for the treatment of some diseases; for other such as cancer, combination therapies are often additive or synergistic in their therapeutic effects and may even be necessary to achieve the full clinical benefit desired. There is specific scientific evidence to rationalize the combination of an inhibitor of LSD1 with all-trans retinoic acid (ATRA), arsenic trioxide, inhibitors of DNA methytransferases such as 5'-azacytidine or 5'-aza 2'-deoxycytidine, inhibitors of NFκB signaling such as sulindac or conventional antineoplastic agents such as anthracyclines or nucleoside analogues such as cytosine arabinoside. Likewise, agents that induce leukemia stem cells into the cell cycle (G-CSF, GM-CSF, stem cell factor, thrombopoietin (TPO)) or agents that negate the contributory role cytokines (TPO, CCL3 (MIP-1)) play in remodeling the niche of cancer stem cells may be useful as part of a combination including an LSD1 inhibitor.

Abbreviations and Definitions

To facilitate understanding of the disclosure, a number of terms and abbreviations as used herein are defined below as follows:

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

The term "about," as used herein when referring to a measurable value such as an amount of a compound, dose, time, temperature, and the like, is meant to encompass variations of 20%, 10%, 5%, 1%, 0.5%, or even 0.1% from the specified amount.

A "therapeutically effective amount" of a drug is an amount of drug or its pharmaceutically acceptable salt that eliminates, alleviates, or provides relief of the symptoms of the disease for which it is administered.

A "subject in need thereof" is a human or non-human animal that exhibits one or more symptoms or indicia of a disease.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.). When n is set at 0 in the context of "0 carbon atoms", it is intended to indicate a bond or null.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl" as used herein, means an alkylsulfonyl group, as defined herein, appended to the parent molecular moiety through an alkyl group, as defined herein. Representative examples of alkylsulfonylalkyl include, but are not limited to, methylsulfonylmethyl and ethylsulfonylmethyl.

The term "acyl," as used herein, alone or in combination, refers to a carbonyl attached to an alkenyl, alkyl, aryl, cycloalkyl, heteroaryl, heterocycle, or any other moiety where the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon group having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl groups include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether group, wherein the term alkyl is as defined below. Examples of suitable alkyl ether groups include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl group containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) group wherein the term alkyl is as defined above and wherein the sulfur may be singly or doubly oxidized. Examples of suitable alkyl thioether groups include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched-chain hydrocarbon group having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C≡C—). Examples of alkynyl groups include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—NR2 group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, hydroxyalkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "amino acid", as used herein, alone or in combination, refers to a —NHCHRC(O)O— group, which may be attached to the parent molecular moiety to give either an N-terminus or C-terminus amino acid, wherein R is independently chosen from hydrogen, alkyl, aryl, heteroaryl, heterocycloalkyl, aminoalkyl, amido, amidoalkyl, carboxyl, carboxylalkyl, guanidinealkyl, hydroxyl, thiol, and thioalkyl, any of which themselves may be optionally substituted. The term C-terminus, as used herein, alone or in combination, refers to the parent molecular moiety being bound to the amino acid at the amino group, to give an amide as described herein, with the carboxyl group unbound, resulting in a terminal carboxyl group, or the corresponding carboxylate anion. The term N-terminus, as used herein, alone or in combination, refers to the parent molecular moiety being bound to the amino acid at the carboxyl group, to give an ester as described herein, with the amino group unbound resulting in a terminal secondary amine, or the corresponding ammonium cation. In other words, C-terminus refers to —NHCHRC(O)OH or to —NHCHRC(O)O⁻ and N-terminus refers to H₂NCHRC(O)O— or to H₃N⁺ECHRC(O)O—.

The term "aryl", as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl group derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The term azetidine, as used herein, alone or in combination, refers to an

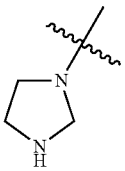

group.

The term pyrrolidine, as used herein, alone or in combination, refers to a

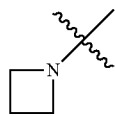 [SMILES: *N1CCC1]

group.

The term imidazolidine, as used herein, alone or in combination, refers to a

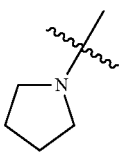 [SMILES: *N1CCCC1]

group.

The term pyrazolidine, as used herein, alone or in combination, refers to a

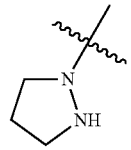 [SMILES: *N1CCCN1]

group.

The term thiomorpholine, as used herein, alone or in combination, refers to a

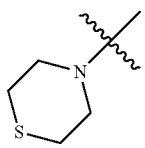 [SMILES: *N1CCSCC1]

group.

The term pyrrole, as used herein, alone or in combination, refers to a

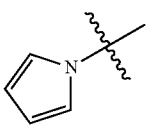 [SMILES: *n1cccc1]

group.

The term pyrazole, as used herein, alone or in combination, refers to a

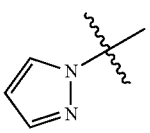

group.

The terms "benzo" and "benz," as used herein, alone or in combination, refer to the divalent group $C_6H_4=$ derived from benzene. Examples include benzothiophene and benzimidazole.

The term "biphenyl" as used herein refers to two phenyl groups connected at one carbon site on each ring.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR' group, with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "guanidine", as used herein, alone or in combination, refers to —NHC(=NH)NH$_2$, or the corresponding guanidinium cation.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl group having the meaning as defined above wherein one or more hydrogen atoms are replaced with a halogen. Specifically embraced are monohaloalkyl, dihaloalkyl and polyhaloalkyl groups. A monohaloalkyl group, for one example, may have an iodo, bromo, chloro or fluoro atom within the group. Dihalo and polyhaloalkyl groups may have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon group, or combinations thereof, fully saturated or containing from 1 to 3 degrees of unsaturation, consisting of the stated number of carbon atoms and from one to three heteroatoms chosen from O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom chosen from O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furanyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuranyl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl, azepinyl, diazepinyl, benzazepinyl, and the like. Exemplary tricyclic heterocyclic groups include carbazolyl, benzidolyl, phenanthrolinyl, dibenzofuranyl, acridinyl, phenanthridinyl, xanthenyl and the like.

The term "heteroarylalkyl" as used herein alone or as part of another group refers to alkyl groups as defined above having a heteroaryl substituent.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, imidazolidinyl, isoindolinyl, morpholinyl, oxazolidinyl, isoxazolidinyl, piperidinyl, piperazinyl, methylpiperazinyl, N-methylpiperazinyl, pyrrolidinyl, pyrazolidinyl, tetrahydrofuranyl, tetrahydropyridinyl, thiomorpholinyl, thiazolidinyl, diazepanyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "hydroxamic acid", as used herein, alone or in combination, refers to —C(=O)NHOH, wherein the parent molecular moiety is attached to the hydroxamic acid group by means of the carbon atom.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, which may be optionally substituted as provided.

The term "lower heteroaryl," as used herein, alone or in combination, means either 1) monocyclic heteroaryl comprising five or six ring members, of which between one and four said members may be heteroatoms chosen from O, S, and N, or 2) bicyclic heteroaryl, wherein each of the fused rings comprises five or six ring members, comprising between them one to four heteroatoms chosen from O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "phosphonate," as used herein, alone or in combination, refers to a —P(=O)(OR)$_2$ group, wherein R is chosen from alkyl and aryl. The term "phosphonic acid", as used herein, alone or in combination, refers to a —P(=O)(OH)$_2$ group.

The term "phosphoramide", as used herein, alone or in combination, refers to a —P(=O)(NR)$_3$ group, with R as defined herein.

The terms "sulfonate," "sulfonic acid," and "sulfonic," as used herein, alone or in combination, refer to the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "0-thiocarbamyl" refers to a —OC(S)NRR', group with R and R' as defined herein.

The term "thiocyanato" refers to a —CNS group.

The term "trihalomethoxy" refers to a X$_3$CO— group where X is a halogen.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent. Similarly, when a designation such as "n" which may be chosen from a group or range of integers is designated to be 0, then the group which it designates is either absent, if in a terminal position, or condenses to form a bond, if it falls between two other groups.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH₃, C(O)CH₃, CO₂CH₃, CO₂H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH₂CH₃), fully substituted (e.g., —CF₂CF₃), monosubstituted (e.g., —CH₂CH₂F) or substituted at a level anywhere in-between fully substituted and monosubstituted (e.g., —CH₂CF₃). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reaction of a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

A salt of a compound can be made by reaction of the appropriate compound, in the form of the free base, with the appropriate acid.

The compounds disclosed herein can exist as polymorphs and other distinct solid forms such as solvates, hydrates, and the like. A compound may be a polymorph, solvate, or hydrate of a salt or of the free base or acid.

While it may be possible for the compounds disclosed herein to be administered as the raw chemical, it is also possible to present them as pharmaceutical formulations (equivalently, "pharmaceutical compositions"). Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, intraadiposal, intraarterial, intracranial, intralesional, intranasal, intraocular, intrapericardial, intraperitoneal, intrapleural, intraprostatical, intrarectal, intrathecal, intratracheal, intratumoral, intraumbilical, intravaginal, intravesicular, intravitreal, and intramedullary), intraperitoneal, rectal, topical (including, without limitation, dermal, buccal, sublingual, vaginal, rectal, nasal, otic, and ocular), local, mucosal, sublingual, subcutaneous, transmucosal, transdermal, transbuccal, transdermal, and vaginal; liposomal, in cremes, in lipid compositions, via a catheter, via a lavage, via continuous infusion, via infusion, via inhalation, via injection, via local delivery, via localized perfusion, bathing target cells directly, or any combination thereof. Administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound disclosed herein or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as hard or soft capsules, wafers, cachets or tablets each containing a predetermined amount of the active ingredient; as a powder or granules; as a syrup, elixir, solution, or a suspension in an aqueous liquid or a non-aqueous liquid; or as an oil-in-water liquid emulsion, a water-in-oil liquid emulsion, or a compound dispersed in a liposome. The active ingredient may also be presented as a bolus, electuary or paste.

Pharmaceutical preparations that can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated to provide delayed, slowed, or controlled release or absorption of the active ingredient therein. Compositions may further comprise an agent that enhances solubility or dispersability. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Depending on the route of administration, the compounds, or granules or particles thereof, may be coated in a material to protect the compounds from the action of acids and other natural conditions that may inactivate the compounds.

The compounds may be formulated for parenteral administration by injection, e.g., by bolus injection or continuous infusion, either to the body or to the site of a disease or wound. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. To administer the therapeutic compound by other than parenteral administration, it may be necessary to coat the compound with, or co-administer the compound with a material to prevent its inactivation (for example, via liposomal formulation).

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Topical ophthalmic, otic, and nasal formulations disclosed herein may comprise excipients in addition to the active ingredient. Excipients commonly used in such formulations include, but are not limited to, tonicity agents, preservatives, chelating agents, buffering agents, and surfactants. Other excipients comprise solubilizing agents, stabilizing agents, comfort-enhancing agents, polymers, emollients, pH-adjusting agents and/or lubricants. Any of a variety of excipients may be used in formulations disclosed herein including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, guar gum, xanthan gum, carrageenan, agar and acacia, starch derivatives, such as starch acetate and hydroxypropyl starch, and also other synthetic products such as polyvinyl alcohol, polyvinylpyrrolidone, polyvinyl methyl ether, polyethylene oxide, preferably cross-linked polyacrylic acid and mixtures of those products. The concentration of the excipient is, typically, from 1 to 100,000 times the concentration of the active ingredient. In preferred embodiments, the excipients to be included in the formulations are typically selected because of their inertness towards the active ingredient component of the formulations.

Relative to ophthalmic, otic, and nasal formulations, suitable tonicity-adjusting agents include, but are not limited to, mannitol, sodium chloride, glycerin, sorbitol and the like. Suitable buffering agents include, but are not limited to, phosphates, borates, acetates and the like. Suitable surfactants include, but are not limited to, ionic and nonionic surfactants (though nonionic surfactants are preferred), RLM 100, POE 20 cetylstearyl ethers such as Procol® CS20 and poloxamers such as Pluronic® F68.

The formulations set forth herein may comprise one or more preservatives. Examples of such preservatives include p-hydroxybenzoic acid ester, sodium perborate, sodium chlorite, alcohols such as chlorobutanol, benzyl alcohol or phenyl ethanol, guanidine derivatives such as polyhexamethylene biguanide, sodium perborate, polyquaternium-1, amino alcohols such as AMP-95, or sorbic acid. In certain embodiments, the formulation may be self-preserved so that no preservation agent is required.

In certain topical embodiments, formulations are prepared using a buffering system that maintains the formulation at a pH of about 4.5 to a pH of about 8. In further embodiments, the pH is from 7 to 8.

Gels for topical or transdermal administration may comprise, generally, a mixture of volatile solvents, nonvolatile solvents, and water. In certain embodiments, the volatile solvent component of the buffered solvent system may include lower (C1-C6) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. Several optional ingredients can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, galactomannan polymers (such as guar and derivatives thereof), and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as stearic or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example, a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

The therapeutic compound may also be administered intraspinally or intracerebrally. Dispersions for these types of administrations can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier that contains a basic dispersion medium and required other ingredients to be pharmacologically sound. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

It should be understood that in addition to the ingredients particularly mentioned above, the formulations described above may include other agents conventional in the art having regard to the type of formulation in question, for example, those suitable for oral administration may include flavoring agents.

Compounds may be administered at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

Preferred unit dosage formulations are those containing an effective dose, as herein below recited, or an appropriate fraction thereof, of the active ingredient. In certain embodiments, a formulation disclosed herein is administered once a day. However, the formulations may also be formulated for administration at any frequency of administration, including once a week, once every 5 days, once every 3 days, once every 2 days, twice a day, three times a day, four times a day, five times a day, six times a day, eight times a day, every hour, or any greater frequency. Such dosing frequency is also maintained for a varying duration of time depending on the therapeutic regimen. The duration of a particular therapeutic regimen may vary from one-time dosing to a regimen that extends for months or years. The formulations are administered at varying dosages, but typical dosages are one to two drops at each administration, or a comparable amount of a gel or other formulation. One of ordinary skill in the art would be familiar with determining a therapeutic regimen for a specific indication.

The amount of active ingredient that may be combined with the carrier materials to produce a single dosage form will vary depending upon the host treated and the particular mode of administration. Similarly, the precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is inflammation, then it may be appropriate to administer an anti-inflammatory agent in combination with the initial therapeutic agent. Alternatively, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). There is even the possibility that two compounds, one of the compounds described herein and a second compound may together achieve the desired therapeutic effect that neither alone could achieve. Alternatively, by way of example only, the benefit experienced by a patient may be increased by administering one of the compounds described herein with another therapeutic agent (which also includes a therapeutic regimen) that also has therapeutic benefit. By way of example only, in a treatment for acute myelogenous leukemia or sickle cell anemia involving administration of one of the compounds described herein, increased therapeutic benefit may result by also providing the patient with another therapeutic agent for sickle cell anemia or for acute myelogenous leukemia. In any case, regardless of the disease, disorder or condition being treated, the overall benefit experienced by the patient may simply be additive of the two therapeutic agents or the two agents may have synergistic therapeutic effects in a patient.

Effective combination therapy may be achieved with a single composition or pharmacological formulation that includes both agents, or with two distinct compositions or formulations, at the same time, wherein one composition includes a compound of the present disclosure, and the other includes the second agent(s). Alternatively, the therapy may precede or follow the other agent treatment by intervals ranging from minutes to months. Administration of the compounds of the present disclosure to a patient will follow general protocols for the administration of pharmaceuticals, taking into account the toxicity, if any, of the drug. It is expected that the treatment cycles would be repeated as necessary.

Specific, non-limiting examples of possible combination therapies include use of certain compounds of the invention with the following agents and classes of agents: agents that inhibit DNA methyltransferases such as decitabine or 5'-azacytadine; agents that inhibit the activity of histone deacetylases, histone de-sumoylases, histone de-ubiquitinases, or histone phosphatases such as hydroxyurea; antisense RNAs that might inhibit the expression of other components of the protein complex bound at the DR site in the gamma globin promoter; agents that inhibit the action of Klfl or the expression of KLF1; agents that inhibit the action of Bcl11a or the expression of BCL11A; and agents that inhibit cell cycle progression such as hydroxyurea, ara-C or daunorubicin; agents that induce differentiation in leukemic cells such as all-trans retinoic acid (ATRA).

Thus, in another aspect, the present invention provides methods for treating diseases or disorders in a human or animal subject in need of such treatment comprising administering to said subject an amount of a compound disclosed herein effective to reduce or prevent said disorder in the subject in combination with at least one additional agent for the treatment of said disorder that is known in the art.

Used either as a monotherapy or in combination with other agents, the compounds disclosed herein are useful in the prevention and/or treatment of beta-hemoglobinopathies such as thalassemia major, sickle cell disease, hemoglobin E/thalassemia, and thalassemia intermedia.

The compounds disclosed herein can be used in the treatment of diseases in which an increase in transcription through the manipulation of epigenetic regulatory factors such as inhibition of KDM1A would be beneficial to the patient. This applies to diseases in which but not limited to loss of function mutations, mutations resulting in haploinsufficiency, deletions and duplications of genetic material or epigenetic regulatory mechanisms have altered the normal expression pattern of a gene or genes that has the effect of altering the dose of a gene product(s). Such diseases may include diseases both acquired and hereditary in which the expression of, for example, cytokines affecting immune function, are altered, X-linked mental retardation and other forms of compromised cognitive or motor function such as Alzheimer and Parkinson disease whether they are the acquired or hereditary forms, lipid disorders such as elevated cholesterol, low density lipoprotein, very low density lipoprotein or triglycerides, both type one and type two diabetes, and Mendelian genetic diseases.

Other disorders or conditions that can be advantageously treated by the compounds disclosed herein include inflammation and inflammatory conditions. Inflammatory conditions include, without limitation: arthritis, including subtypes and related conditions such as rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis; osteoporosis, tendonitis, bursitis, and other related bone and joint disorders; gastrointestinal conditions such as reflux esophagitis, diarrhea, inflammatory bowel disease, Crohn's disease, gastritis, irritable bowel syndrome, ulcerative colitis, acute and chronic inflammation of the pancreas; pulmonary inflammation, such as that associated with viral infections and cystic fibrosis; skin-related conditions such as psoriasis, eczema, burns, sunburn, dermatitis (such as contact dermatitis, atopic dermatitis, and allergic dermatitis), and hives; pancreatitis, hepatitis, pruritus and vitiligo. In addition, compounds of invention are also useful in organ transplant patients either alone or in combination with conventional immunomodulators.

Autoimmune disorders may be ameliorated by the treatment with compounds disclosed herein. Autoimmune disorders include Crohn's disease, ulcerative colitis, dermatitis, dermatomyositis, diabetes mellitus type 1, Goodpasture's syndrome, Graves' disease, Guillain-Barré syndrome (GBS), autoimmune encephalomyelitis, Hashimoto's disease, idiopathic thrombocytopenic purpura, lupus erythematosus, mixed connective tissue disease, multiple sclerosis (MS), myasthenia gravis, narcolepsy, pemphigus vulgaris, pernicious anemia, psoriasis, psoriatic arthritis, polymyositis, primary biliary cirrhosis, rheumatoid arthritis, Sjögren's syndrome, scleroderma, temporal arteritis (also known as "giant cell arteritis"), vasculitis, and Wegener's granulomatosis.

The compounds disclosed herein are also useful for the treatment of organ and tissue injury associated with severe burns, sepsis, trauma, wounds, and hemorrhage- or resuscitation-induced hypotension, and also in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephritis, nephrotic syndrome, Behcet's syndrome, polymyositis, gingivitis, periodontis, swelling occurring after injury, ischemias including myocardial ischemia, cardiovascular ischemia, and ischemia secondary to cardiac arrest, and the like.

The compounds disclosed herein are also useful for the treatment of certain diseases and disorders of the nervous system. Central nervous system disorders in KDM1A inhibition is useful include cortical dementias including Alzheimer's disease, central nervous system damage resulting from stroke, ischemias including cerebral ischemia (both focal ischemia, thrombotic stroke and global ischemia (for example, secondary to cardiac arrest), and trauma. Neurodegenerative disorders in which KDM1A inhibition is useful include nerve degeneration or nerve necrosis in disorders such as hypoxia, hypoglycemia, epilepsy, and in cases of central nervous system (CNS) trauma (such as spinal cord and head injury), hyperbaric oxygen-induced convulsions and toxicity, dementia e.g., pre-senile dementia, and AIDS-related dementia, cachexia, Sydenham's chorea, Huntington's disease, Parkinson's Disease, amyotrophic lateral sclerosis (ALS), Korsakoffs disease, cognitive disorders relating to a cerebral vessel disorder, hypersensitivity, sleeping disorders, schizophrenia, depression, depression or other symptoms associated with Premenstrual Syndrome (PMS), and anxiety.

Still other disorders or conditions advantageously treated by the compounds disclosed herein include the prevention or treatment of hyperproliferative diseases, especially cancers, either alone or in combination with standards of care especially those agents that target tumor growth by re-instating tumor suppressor genes in the malignant cells. Hematological and non-hematological malignancies which may be treated or prevented include but are not limited to multiple myeloma, acute and chronic leukemias and hematopoietic proliferative and neoplastic disorders including Myelodysplastic Syndrome (MDS), Acute Myelogenous Leukemia (AML), Acute Lymphocytic Leukemia (ALL), Chronic Lymphocytic Leukemia (CLL), and Chronic Myelogenous Leukemia (CML), lymphomas, including Hodgkin's lymphoma and non-Hodgkin's lymphoma (low, intermediate, and high grade), as well as solid tumors and malignancies of the brain, head and neck, breast, lung (including non-small-cell lung cancer), reproductive tract, upper digestive tract, pancreas, liver, renal system, bladder, prostate and colorectal. The present compounds and methods can also be used to treat fibrosis, such as that which occurs with radiation therapy. The present compounds and methods can be used to treat subjects having or prevent the progression of adenomatous polyps, including those with familial adenomatous polyposis (FAP) or sarcoidosis. Non-cancerous proliferative disorders additionally include psoriasis, eczema, and dermatitis.

The present compounds may also be used in co-therapies, partially or completely, in place of other conventional anti-inflammatory therapies, such as together with steroids, NSAIDs, COX-2 selective inhibitors, 5-lipoxygenase inhibitors, $LTB_4$ antagonists and $LTA_4$ hydrolase inhibitors. The compounds disclosed herein may also be used to prevent tissue damage when therapeutically combined with antibacterial or antiviral agents.

The compounds disclosed herein are also useful for the treatment of treat metabolic disorders. KDM1A, using flavin adenosine dinucleotide (FAD) as a cofactor, epigenetically regulates energy-expenditure genes in adipocytes depending on the cellular FAD availability. Additionally, loss of KDM1A function induces a number of regulators of energy expenditure and mitochondrial metabolism resulting in the activation of mitochondrial respiration. Furthermore, in the adipose tissues from mice fed a high-fat diet, expression of KDM1A-target genes is reduced.

Metabolic syndrome (also known as metabolic syndrome X) is characterized by having at least three of the following symptoms: insulin resistance; abdominal fat—in men this is defined as a 40 inch waist or larger, in women 35 inches or larger; high blood sugar levels—at least 110 milligrams per deciliter (mg/dL) after fasting; high triglycerides—at least 150 mg/dL in the blood stream; low HDL-less than 40 mg/dL; pro-thrombotic state (e.g., high fibrinogen or plasminogen activator inhibitor in the blood); or blood pressure of 130/85 mmHg or higher. A connection has been found between metabolic syndrome and other conditions such as obesity, high blood pressure and high levels of LDL cholesterol, all of which are risk factors for cardiovascular diseases. For example, an increased link between metabolic syndrome and atherosclerosis has been shown. People with metabolic syndrome are also more prone to developing type 2 diabetes, as well as PCOS (polycystic ovarian syndrome) in women and prostate cancer in men.

As described above, insulin resistance can be manifested in several ways, including type 2 diabetes. Type 2 diabetes is the condition most obviously linked to insulin resistance. Compensatory hyperinsulinemia helps maintain normal glucose levels often for decades before overt diabetes develops. Eventually the beta cells of the pancreas are unable to overcome insulin resistance through hypersecretion. Glucose levels rise and a diagnosis of diabetes can be made. Patients with type 2 diabetes remain hyperinsulinemic until they are in an advanced stage of disease. As described above, insulin resistance can also correlate with hypertension. One half of patients with essential hypertension are insulin resistant and hyperinsulinemic, and there is evidence that blood pressure is linked to the degree of insulin resistance. Hyperlipidemia, too, is associated with insulin resistance. The lipid profile of patients with type 2 diabetes includes increased serum very-low-density lipoprotein (VLDL) cholesterol and triglyceride levels and, sometimes, a decreased low-density lipoprotein (LDL) cholesterol level. Insulin resistance has been found in persons with low levels of high-density lipoprotein HDL). Insulin levels have also been linked to VLDL synthesis and plasma triglyceride levels.

Specific metabolic diseases and symptoms to be treated by the compounds, compositions, and methods disclosed herein are those mediated at least in part by KDM1A. Accordingly, disclosed herein are methods: for treating insulin resistance in a subject; for reducing glycogen accumulation in a subject; for raising HDL or HDLc, lowering LDL or LDLc, shifting LDL particle size from small dense to normal LDL, lowering VLDL, lowering triglycerides, or inhibiting cholesterol absorption in a subject; for reducing insulin resistance, enhancing glucose utilization or lowering blood pressure in a subject; for reducing visceral fat in a subject; for reducing serum transaminases in a subject; for inducing mitochondrial respiration in a subject; or for treating disease; all comprising the administration of a therapeutic amount of a compound as described herein, to a patient in need thereof. In further embodiments, the disease to be treated may be a metabolic disease. In further embodiment, the metabolic disease may be selected from the group consisting of: obesity, diabetes mellitus, especially Type 2 diabetes, hyperinsulinemia, glucose intolerance, metabolic syndrome X, dyslipidemia, hypertriglyceridemia, hypercholesterolemia, and hepatic steatosis. In other embodiments, the disease to be treated may be selected from the group consisting of: cardiovascular diseases including vascular disease, atherosclerosis, coronary heart disease, cerebrovascular disease, heart failure and peripheral vessel disease. In preferred embodiments, the methods above do not result in the induction or maintenance of a hypoglycemic state.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Methods

General Synthetic Methods for Preparing Compounds

The following schemes can be used to practice the present invention.

Scheme 1

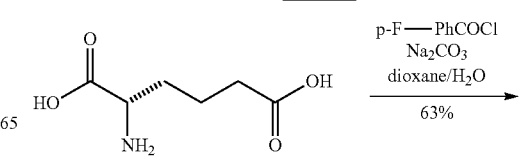

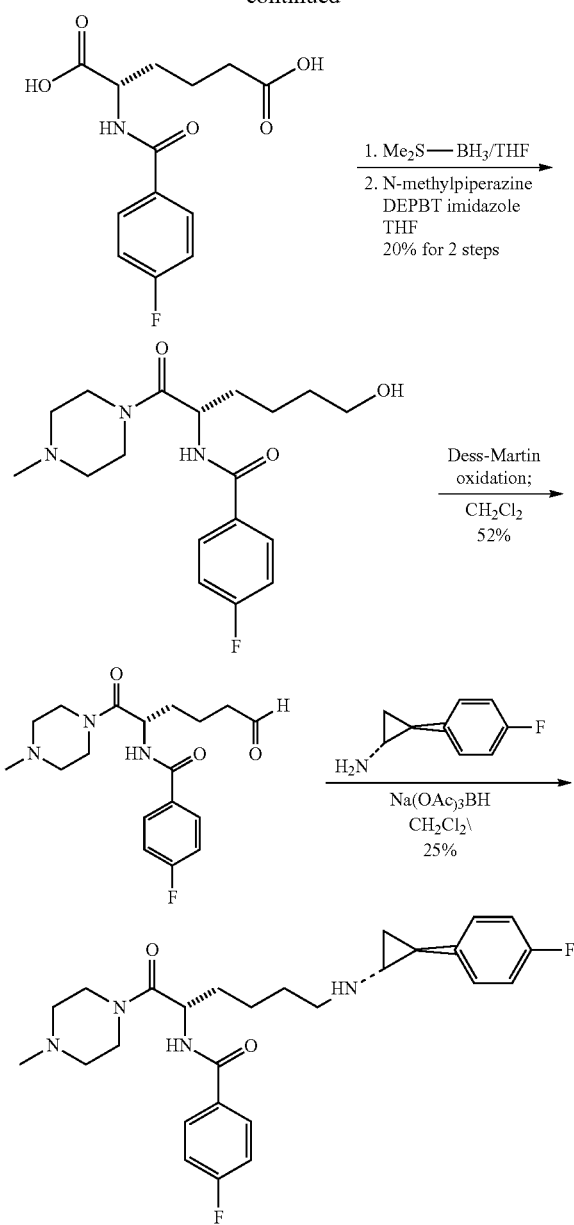

Scheme 1 depicts an example of a synthesis wherein R³ and R⁵ are each para-fluorophenyl in the final product. However, by substituting reagents wherein the fluorine is replaced by another substituent such as methoxy or chlorine, or wherein additional substituents on the phenyl are present, or wherein the phenyl is replaced by another aryl or a heteroaryl in either step 1 or step 4, additional compounds of Formula I can be made. The trans-2-phenyl-aminocyclopropane substituent can exist in two distinct steric forms that are prepared from the (+) and the (−) forms of the starting material trans-2-phenyl aminocyclopropane. Further, compounds where n=3 may be prepared from L-glutamic acid rather than L-adipic acid by the same methods. Additional variations can be accomplished through methods known in the art.

The invention is further illustrated by the following examples, which have not been made yet or tested. The methods exemplified below may also be extrapolated to compounds disclosed herein which may not yet have not been made or tested.

Intermediate A: (1R,2S)-2-(4-fluorophenyl)-1-methylcyclopropanamine

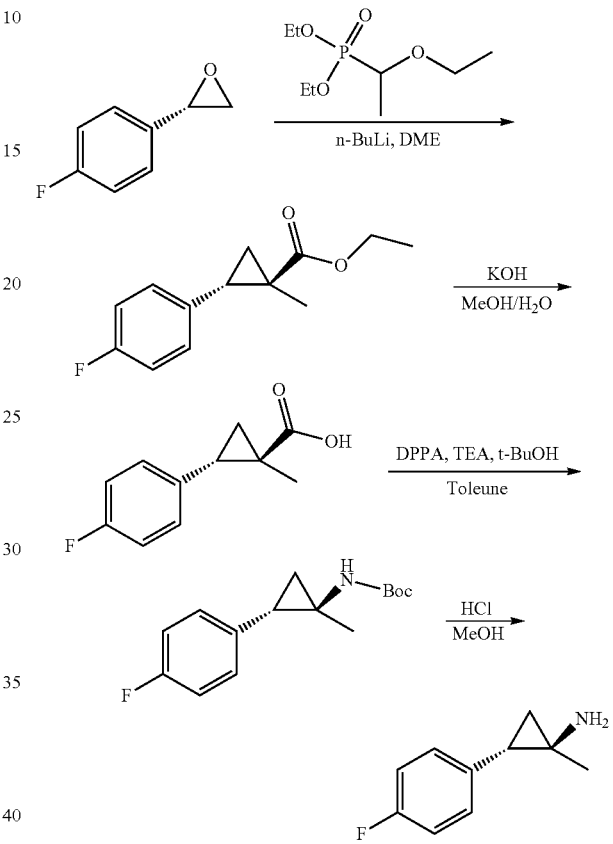

A solution of ethyl 2-(diethoxyphosphoryl)propanoate (3.45 g, 14.48 mmol, 2.00 equiv) in ethylene glycol dimethyl ether (20 mL) was treated with n-BuLi (2.5M) (5.8 mL) dropwise with stirring at 0° C. The resulting solution was stirred for 30 min at room temperature. To this was added 2-(4-fluorophenyl)oxirane (1 g, 7.24 mmol, 1.00 equiv). The resulting solution was stirred for 12 h while the temperature was maintained at 80° C. in an oil bath. The reaction mixture was cooled to RT. The reaction was then quenched by the addition of 20 mL of water. The resulting solution was extracted with ethyl acetate and the organic layers was dried and concentrated. The residue was chromatographed on silica gel and eluted with ethyl acetate/petroleum ether (1:100). This resulted in 1 g (62%) of ethyl (1R)-2-(4-fluorophenyl)-1-methylcyclopropane-1-carboxylate as yellow oil. A solution of ethyl (1R)-2-(4-fluorophenyl)-1-methylcyclopropane-1-carboxylate (1 g, 4.50 mmol, 1.00 equiv) in methanol/H₂O (10/2 mL) and potassium hydroxide (1.26 g, 22.46 mmol, 4.99 equiv) was stirred for 10 h at room temperature. The resulting solution was diluted with H₂O. The pH value of the solution was adjusted to 2 with hydrochloric acid (2 mol/L). The resulting solution was extracted with ethyl acetate and the organic layers combined and dried over anhydrous sodium sulfate and concentrated under vacuum. This resulted in 800 mg (92%) of (1R)-2-(4-fluorophenyl)-1-methylcyclopropane-1-carboxylic acid as yellow oil. A solution of (1R)-2-(4-fluorophenyl)-1-methylcyclopropane-1-carboxylic acid (400 mg, 2.06 mmol, 1.00 equiv) in toluene (10 mL) was mixed with diphenoxyphosphoryl azide (680 mg, 2.47 mmol, 1.20 equiv), and triethylamine (312 mg, 3.08 mmol, 1.50 equiv). The resulting solution was stirred for 30 min at 90° C. in an oil bath. Then, tert-butanol (2 mL) was added. The resulting solution was allowed to react, with stirring, for an additional 12 h while the temperature was maintained at 90° C. in an oil bath. The reaction mixture was cooled to room temperature and the resulting solution was diluted with ethyl acetate. The resulting mixture was washed with H₂O. The mixture was dried over anhydrous sodium sulfate and concentrated under vacuum. The residue was chromatographed on a silica gel column and eluted with ethyl acetate/petroleum ether (1:100). This resulted in 350 mg (64%) of tert-butyl N-[(1R)-2-(4-fluorophenyl)-1-methylcyclopropyl]carbamate as yellow oil. A solution of tert-butyl N-[(1R,2S)-2-(4-fluorophenyl)-1-methylcyclopropyl]carbamate (350 mg, 1.32 mmol, 1.00 equiv) in methanol (HCl) (10 mL) was stirred for 2 h at room temperature. The resulting solution was diluted with 10 mL of H₂O. The pH value of the solution was adjusted to 9 with saturated sodium bicarbonate solution. The resulting solution was extracted with 3×10 mL of ethyl acetate and the organic layers combined and dried over anhydrous sodium sulfate and concentrated under vacuum. This resulted in 200 mg (92%) of (1R,2S)-2-(4-fluorophenyl)-1-methylcyclopropan-1-amine as yellow oil.

Example 1: N—((S)-1-oxo-6-(((1R,2S)-2-phenylcyclopropyl)amino)-1-(pyrrolidin-1-yl)hexan-2-yl)benzamide

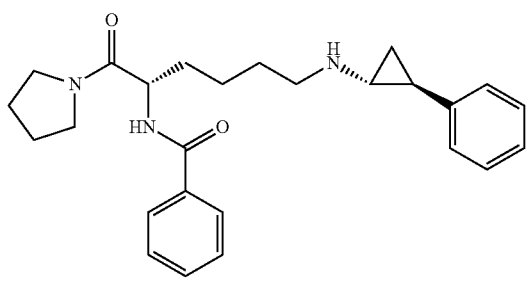 [SMILES: O=C(N[C@@H](CCCCN[C@@H]1C[C@H]1c1ccccc1)C(=O)N1CCCC1)c1ccccc1]

Reaction Scheme for Alkyl-Linked Compounds

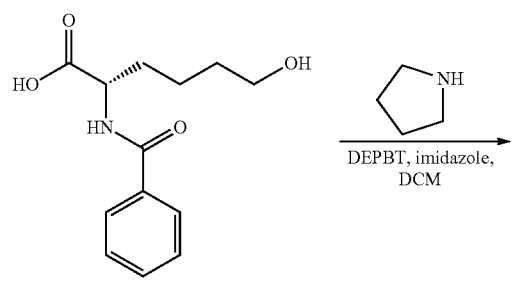

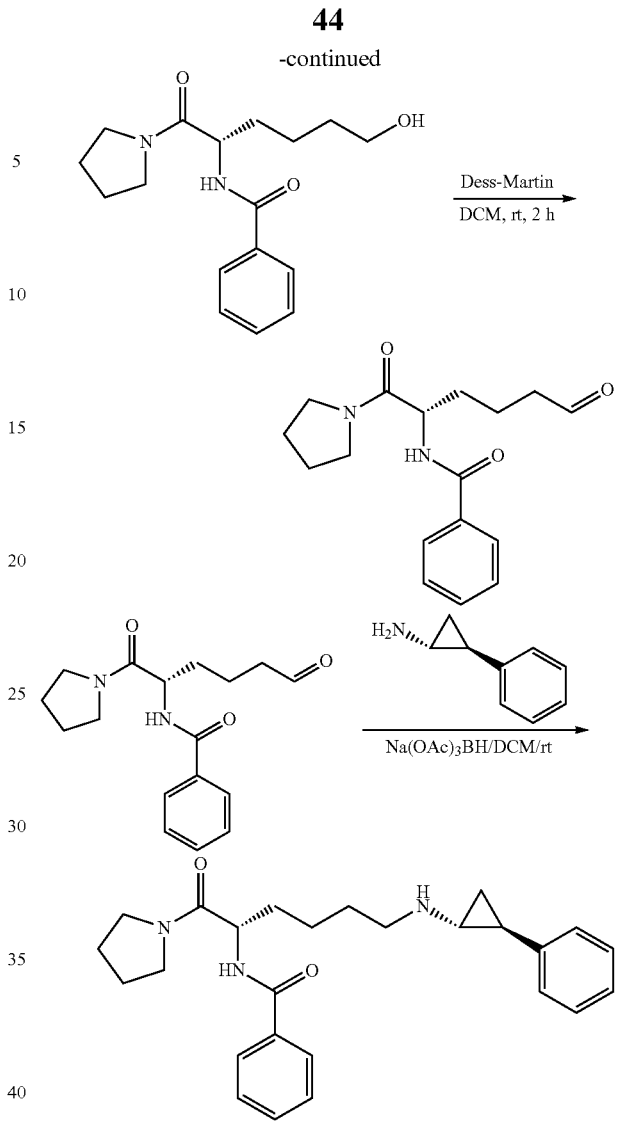

(S)-2-benzamido-6-hydroxyhexanoic acid was prepared from (S)-2-amino-6-hydroxyhexanoic acid. This material (1 g, 3.98 mmol, 1.00 equiv) in tetrahydrofuran was reacted with 3-(diethoxyphosphoryloxy)-1,2,3-benzotriazin-4(3H)-one (DEPBT) (2.4 g, 8.03 mmol, 2.00 equiv) and imidazole (542 mg, 7.97 mmol, 2.00 equiv). This was followed by the addition of a solution of pyrrolidine (283 mg, 3.98 mmol, 1.00 equiv) in tetrahydrofuran at 0° C. in 30 min. The resulting solution was stirred for 16 h at room temperature. The solution was diluted with KH₂PO₄(aq.). The aqueous layer was extracted with ethyl acetate and the organic layers were washed with brine and dried over anhydrous sodium sulfate. After filtration, solvent was removed under reduced pressure. The residue was purified by preparative HPLC and eluted with MeCN with 0.5% NH₄HCO₃. This resulted in 640 mg (53%) of (S)—N-(6-hydroxy-1-oxo-1-(pyrrolidin-1-yl)hexan-2-yl)benzamide as a light yellow oil. (S)—N-(6-hydroxy-1-oxo-1-(pyrrolidin-1-yl)hexan-2-yl)benzamide (640 mg, 2.10 mmol, 1.00 equiv) in dichloromethane (100 ml) was oxidized with Dess-Martin periodinane (DMP) (893 mg, 2.11 mmol, 1.00 equiv). The resulting solution was stirred for 30 min at 0° C. in a water/ice bath and was then diluted with Na₂SO₃(aq.) and NaHCO₃(aq.). The aqueous layers were extracted with ethyl acetate and the organic layers were washed with brine and dried over anhydrous sodium sulfate. After filtration, solvent was removed under reduced pressure. The residue was chromatographed on silica gel and eluted with ethyl acetate/petroleum ether (10:1). This gave 150 mg (24%) of (S)—N-(1,6-dioxo-1-(pyrrolidin-1-yl)hexan-2-yl)benzamide as a white solid. (S)—N-(1,6-dioxo-1-(pyrrolidin-1-yl)hexan-2-yl)benzamide (150 mg, 0.50 mmol, 1.00 equiv) was dissolved in dichloromethane (25 mL). (1R,2S)-2-phenylcyclopropanamine (66 mg, 0.50 mmol, 1.00 equiv) was added. After stirring 5 minutes, sodium triacetoxyborohydride (252 mg, 1.19 mmol, 2.40 equiv) was added. The resulting solution was stirred for 30 min at 0° C. After the reaction was completed, the resulting solution was diluted with sat..NaHCO₃. Then it was extracted with dichloromethane. The organic layers were washed with brine and dried over anhydrous sodium sulfate. Solvent was removed under reduced pressure and the residue was purified by Prep-HPLC (CAN/H₂O with 0.5% NH₄HCO₃). This resulted in 29 mg (14%) of N—((S)-1-oxo-6-4(1R,2S)-2-phenylcyclopropyl)amino)-1-(pyrrolidin-1-yl)hexan-2-yl)benzamide as colorless oil. ¹H NMR (300 MHz, CD₃OD-d₄) δ ppm: 7.85 (d, J=7.5 Hz, 2H), 7.60-7.00 (m, 8H), 4.85-4.75 (m, 1H), 3.92-3.80 (m, 1H), 3.70-3.30 (m, 4H), 2.74 (t, J=7.2 Hz, 1H), 2.36-2.28 (m, 1H), 2.07-1.75 (m, 7H), 1.74-1.37 (m, 4H), 1.10-0.95 (m, 2H); MS (ES, ink): 420 (M+H).

Example 2: N—((S)-1-oxo-6-(((1R,2S)-2-phenylcyclopropyl)amino)-1-(piperidin-1-yl)hexan-2-yl)benzamide

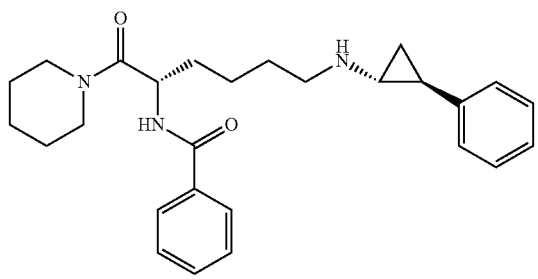 [SMILES: O=C(N[C@@H](CCCCN[C@@H]1C[C@H]1c1ccccc1)C(=O)N1CCCCC1)c1ccccc1]

N—((S)-1-oxo-6-(((1R,2S)-2-phenylcyclopropyl) amino)-1-(piperidin-1-yl)hexan-2-yl)benzamide was prepared in the same manner as was described for the synthesis of N—((S)-1-oxo-6-(((1R,2S)-2-phenylcyclopropyl)amino)-1-(pyrrolidin-1-yl)hexan-2-yl)benzamide. (S)-2-benzamido-6-hydroxyhexanoic acid was coupled with piperidine using 3-(diethoxyphosphoryloxy)-1,2,3-benzotriazin-4 (3H)-one and imidazole. The resultant alcohol (S)—N-(6-hydroxy-1-oxo-1-(piperidin-1-yl)hexan-2-yl)benzamide was oxidized under Dess-Martin conditions to the aldehyde (S)—N-(1,6-dioxo-1-(piperidin-1-yl)hexan-2-yl)benzamide. This was coupled with (1R,2S)-2-phenylcyclopropanamine under reductive amination conditions (Na(OAc)₃BH) to yield the desired product N—((S)-1-oxo-6-(((1R,2S)-2-phenylcyclopropyl)amino)-1-(piperidin-1-yl)hexan-2-yl) benzamide as a colorless oil. ES, m/z=434 (M+H). ¹H NMR (300 MHz, CD₃OD-d₄) δ ppm: 7.86 (d, J=7.2 Hz, 2H), 7.70-7.40 (m, 3H), 7.30-7.15 (m, 2H), 7.15-7.08 (m, 1H), 7.06 (d, J=7.2 Hz, 2H), 5.15-5.00 (m, 1H), 3.80-3.60 (m, 2H), 3.60-3.40 (m, 2H), 2.34 (t, J=7.2 Hz, 2H), 2.40-2.30 (m, 1H), 2.10-1.40 (m, 4H), 1.15-1.00 (m, 2H).

Example 3: 4-fluoro-N—((S)-6-(((1R,2S)-2-(4-fluorophenyl)cyclopropyl)amino)-1-(4-methylpiperazin-1-yl)-1-oxohexan-2-yl)benzamide

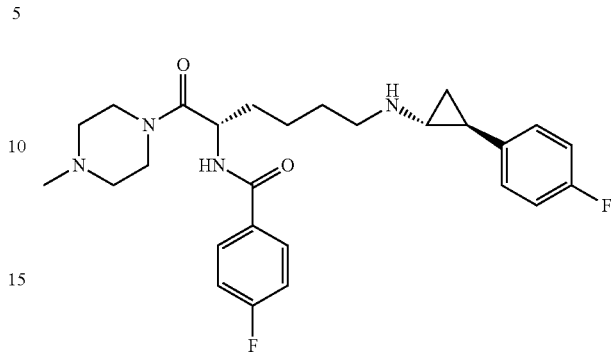

4-fluoro-N—((S)-6-(((1R,2S)-2-(4-fluorophenyl)cyclopropyl)amino)-1-(4-methylpiperazin-1-yl)-1-oxohexan-2-yl)benzamide was prepared in a manner analogous to the previous example. The alcohol 4-fluoro-N—((S)-6-(((1R,2S)-2-(4-fluorophenyl)cyclopropyl)amino)-1-(4-methylpiperazin-1-yl)-1-oxohexan-2-yl)benzamide was prepared by reduction of (S)-2-(4-fluorobenzamido)hexanedioic acid with Me₂S—BH₃. This type of reduction was used to prepare similar alcohols (e.g. The alcohol starting material (S)-2-benzamido-6-hydroxyhexanoic acid for the synthesis of N—((S)-1-oxo-6-(((1R,2S)-2-phenylcyclopropyl) amino)-1-(pyrrolidin-1-yl)hexan-2-yl)benzamide). Into a 1000-mL 3-necked round-bottom flask purged and maintained with an inert atmosphere of nitrogen, was placed a solution of (S)-2-(4-fluorobenzamido)hexanedioic acid (10 g, 35.30 mmol, 1.00 equiv) in tetrahydrofuran (300 ml). Then a solution of Me₂S—BH₃ (11 mL, 3.00 equiv) in tetrahydrofuran (50 ml) was added at 0° C. The resulting solution was stirred for 3 h at 0° C. in an ice/salt bath. The reaction was then quenched by the addition of 20 ml of methanol. The resulting mixture was concentrated under vacuum. The resulting solution was diluted with 300 ml of sat.Na₂CO₃. The resulting solution was extracted with 3×100 mL of ethyl acetate and the aqueous layers combined. The pH value of the solution was adjusted to 2 with hydrochloric acid (2 mol/L). The resulting solution was extracted with 3×200 ML of ethyl acetate and the organic layers combined. The resulting mixture was washed with 1×500 mL of brine. The mixture was dried over anhydrous sodium sulfate. The solids were filtered out. The resulting mixture was concentrated under vacuum. This resulted in 6 g (63%) of (S)-2-(4-fluorobenzamido)-6-hydroxyhexanoic acid as colorless oil. This material was reacted with N-methyl piperazine followed by Dess-Martin oxidation and coupling via reductive amination with (1R,2S)-2-(4-fluorophenyl)cyclopropanamine in the manner described for the synthesis of N—((S)-1-oxo-6-(((1R,2S)-2-phenylcyclopropyl)amino)-1-(pyrrolidin-1-yl)hexan-2-yl)benzamide to yield the desired product 4-fluoro-N—((S)-6-(((1R,2S)-2-(4-fluorophenyl)cyclopropyl)amino)-1-(4-methylpiperazin-1-yl)-1-oxohexan-2-yl)benzamide as colorless oil. ES, m/s=485*M+H). ¹H NMR (300 MHz, CD₃OD-d₄) δ ppm: 7.83 (dd, J₁=5.4 Hz, J₂=1.4 Hz, 2H), 7.18-7.04 (m, 3H), 7.00-6.87 (m, 4H), 5.17-5.05 (m, 1H), 3.78-3.50 (m, 4H), 2.71 (t, J=6.9 Hz, 2H), 2.30 (s, 3H), 2.28-2.21 (m, 1H), 1.90-1.78 (m, 2H), 1.72-1.31 (m, 9H), 1.07-0.96 (m, 1H), 0.94-0.86 (m, 1H).

Example 4: N—((S)-1-(4-methylpiperazin-1-yl)-1-oxo-6-(((1R,2S)-2-phenylcyclopropyl)amino)hexan-2-yl)benzamide

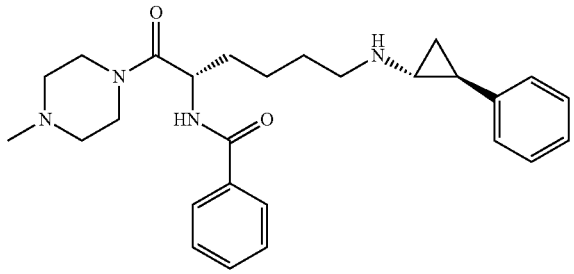 [SMILES: CN1CCN(C(=O)[C@H](CCCCN[C@@H]2C[C@H]2c2ccccc2)NC(=O)c2ccccc2)CC1]

N—((S)-1-(4-methylpiperazin-1-yl)-2-phenylcyclopropyl)amino)hexan-2-yl)benzamide was prepared in the same manner as was described for the synthesis of N—((S)-1-oxo-6-(((1R,2S)-2-phenylcyclopropyl)amino)-1-(pyrrolidin-1-yl)hexan-2-yl)benzamide. (S)-2-benzamido-6-hydroxyhexanoic acid was coupled with N-methyl piperidine using 3-(diethoxyphosphoryloxy)-1,2,3-benzotriazin-4(3H)-one (DEPBT) and imidazole. The resultant alcohol (S)—N-(6-hydroxy-1-(4-methylpiperazin-1-yl)-1-oxohexan-2-yl)benzamide was oxidized under Dess-Martin conditions to the aldehyde (S)—N-(1-(4-methylpiperazin-1-yl)-1,6-dioxohexan-2-yl)benzamide. This was coupled with (1R,2S)-2-phenylcyclopropanamine under reductive amination conditions (Na(OAc)$_3$BH) to yield the desired N—((S)-1-(4-methylpiperazin-1-yl)-1-oxo-6-(((1R,2S)-2-phenylcyclopropyl)amino)hexan-2-yl)benzamide as a colorless oil. $^1$H NMR (300 MHz, CD$_3$OD-d$_4$) δ ppm: 7.91-7.80 (m, 2H), 7.60-7.42 (m, 3H), 7.26-7.18 (m, 2H), 7.15-7.02 (m, 3H), 5.03 (dd, J=8.1 Hz, 6.0 Hz, 1H), 3.85-3.48 (m, 4H), 2.73 (t, J=7.2 Hz, 2H), 2.60-2.35 (m, 4H), 2.35-2.25 (m, 4H), 1.95-1.72 (m, 3H), 1.70-1.38 (m, 4H), 1.10-0.95 (m, 2H); MS (ES, m/z): 449 (M+H).

Example 5: 4-fluoro-N—((R)-3-((2-(((1R,2S)-2-(4-fluorophenyl)cyclopropyl)amino)ethyl)sulfonyl)-1-morpholino-1-oxopropan-2-yl)benzamide

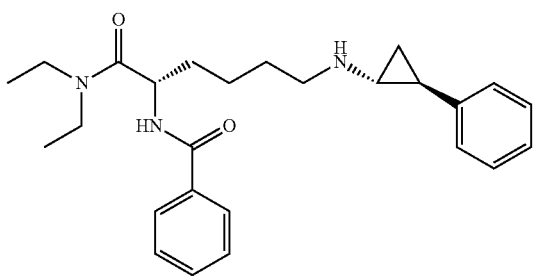 [SMILES: CCN(CC)C(=O)[C@H](CCCCN[C@@H]1C[C@H]1c1ccccc1)NC(=O)c1ccccc1]

4-fluoro-N—((R)-3-((2-(((1R,2S)-2-(4-fluorophenyl)cyclopropyl)amino)ethyl)sulfonyl)-1-morpholino-1-oxopropan-2-yl)benzamide was prepared by the method described for N—((S)-1-oxo-6-(((1R,2S)-2-phenylcyclopropyl)amino)-1-(pyrrolidin-1-yl)hexan-2-yl)benzamide. (S)-2-benzamido-6-hydroxyhexanoic acid was reacted with diethyl amine with 3-(diethoxyphosphoryloxy)-1,2,3-benzotriazin-4(3H)-one (DEPBT)/imidazole to give (S)—N-(1-(diethylamino)-6-hydroxy-1-oxohexan-2-yl)benzamide in 45% yield as a colorless oil. This was oxidized under Dess Martin conditions to give the aldehyde (S)—N-(1-(diethylamino)-1,6-dioxohexan-2-yl)benzamide in 45% yield as a yellow oil. The aldehyde was reacted with (1R,2S)-2-phenylcyclopropanamine under reductive amination conditions (Na(OAc)$_3$BH) to give N—((S)-1-(diethylamino)-1-oxo-6-(((1R,2S)-2-phenylcyclopropyl)amino)hexan-2-yl)benzamide as a light yellow oil (6% yield). ES, m/z=422 (M+H). $^1$H NMR (300 MHz, CD$_3$OD-d$_4$) δ ppm: 7.85 (dd, J$_1$=5.25 Hz, J$_2$=1.65 Hz, 2H), 7.68-7.40 (m, 3H), 7.22 (t, J=7.35 Hz, 2H), 7.15-7.00 (m, 3H), 4.94-5.05 (m, 1H), 3.60-3.45 (m, 3H), 3.30-3.21 (m, 1H), 2.73 (t, J=7.2 Hz, 1H), 2.27-2.35 (m, 1H), 1.79-1.72 (m, 3H), 1.67-1.39 (m, 4H), 1.31 (t, J=7.05 Hz, 3H), 1.14 (t, J=7.05 Hz, 3H), 1.10-0.95 (m, 2H)

Example 6: N—((S)-1-morpholino-1-oxo-6-(((1R,2S)-2-phenylcyclopropyl)amino)hexan-2-yl)benzamide

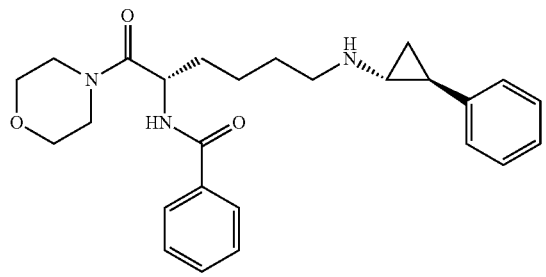 [SMILES: O=C(N[C@@H](CCCCN[C@@H]1C[C@H]1c1ccccc1)C(=O)N1CCOCC1)c1ccccc1]

N—((S)-1-morpholino-1-oxo-6-(((1R,2S)-2-phenylcyclopropyl)amino)hexan-2-yl)benzamide was prepared by the method that was described earlier for N—((S)-1-oxo-6-(((1R,2S)-2-phenylcyclopropyl)amino)-1-(pyrrolidin-1-yl)hexan-2-yl)benzamide. (S)-2-benzamido-6-hydroxyhexanoic acid was reacted with morpholine, 3-(diethoxyphosphoryloxy)-1,2,3-benzotriazin-4(3H)-one (DEPBT) and imidazole to give (S)—N-(6-hydroxy-1-morpholino-1-oxohexan-2-yl)benzamide in 37% yield as a colorless oil. This was oxidized under Dess-Martin conditions to give (S)—N-(1-morpholino-1,6-dioxohexan-2-yl)benzamide in 45% yield as a colorless oil. This material was reacted with (1R,2S)-2-phenylcyclopropanamine under reductive amination conditions (Na(OAc)$_3$BH) to give, after prep-hplc, a 7% yield of N—((S)-1-morpholino-1-oxo-6-(((1R,2S)-2-phenylcyclopropyl)amino)hexan-2-yl)benzamide as a light yellow oil. ES, m/z=436 (M+H). $^1$H NMR (300 MHz, CD$_3$OD-d$_4$) δ ppm: 7.85 (d, J=6.9 Hz, 2H), 7.60-7.50 (m, 1H), 7.46 (t, J=7.35 Hz, 2H), 7.22 (t, J=7.35 Hz, 2H), 7.15-7.08 (m, 1H), 7.05 (d, J=6.9 Hz, 2H), 5.00 (t, J=7.05 Hz, 1H), 3.80-3.48 (m, 8H), 2.32 (t, J=3.0 Hz, 2H), 2.36-2.08 (m, 1H), 1.95-1.86 (m, 1H), 1.86-1.72 (m, 2H), 1.70-1.54 (m, 2H), 1.54-1.40 (m, 2H), 0.97-1.12 (m, 2H)

Example 7: N-[(2S)-6-[[(1R,2S)-2-(4-fluorophenyl)cyclopropyl]amino]-1-oxo-1-(piperidin-1-yl)hexan-2-yl]pyridine-2-carboxamide

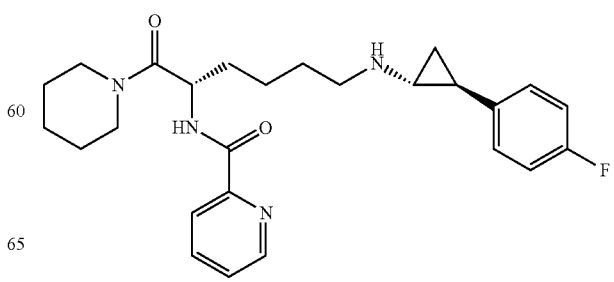

N-[(2S)-6-[[(1R,2S)-2-(4-fluorophenyl)cyclopropyl]amino]-1-oxo-1-(piperidin-1-yl)hexan-2-yl]pyridine-2-carboxamide was prepared by the method that was described for of N—((S)-1-oxo-6-(((1R,2S)-2-phenylcyclopropyl)amino)-1-(pyrrolidin-1-yl)hexan-2-yl)benzamide. A 240 mg sample of (S)—N-(6-hydroxy-1-oxo-1-(piperidin-1-yl)hexan-2-yl)picolinamide was converted under Dess-Martin conditions to the aldehyde (S)—N-(1,6-dioxo-1-(piperidin-1-yl)hexan-2-yl)picolinamide as a yellow oil. Under reductive amination conditions with (1R,2S)-2-(4-fluorophenyl)cyclopropanamine the aldehyde gave the product N—((S)-6-(((1R,2S)-2-(4-fluorophenyl)cyclopropyl)amino)-1-oxo-1-(piperidin-1-yl)hexan-2-yl)picolinamide as a light yellow oil. ES, m/z=453 (M+1). $^1$H NMR (300 MHz, DMSO-$_{d6}$, δ): 8.65 (d, J=3.3 Hz, 1H), 8.09 (d, J=7.8 Hz, 1H), 8.03-7.94 (m, 1H), 7.65-7.42 (m, 1H), 7.15-6.89 (m, 4H), 5.05-5.18 (m, 1H), 3.74-3.43 (m, 4H), 2.70 (t, J=7.4 Hz, 2H), 2.32-2.17 (m, 1H), 1.99-1.79 (m, 2H), 1.80-1.38 (m, 11H), 1.07-0.89 (m, 2H).

Example 8: N—((S)-6-(((1R,2S)-2-(4-fluorophenyl)-1-methylcyclopropyl)amino)-1-(4-(methylsulfonyl)piperazin-1-yl)-1-oxohexan-2-yl)benzamide

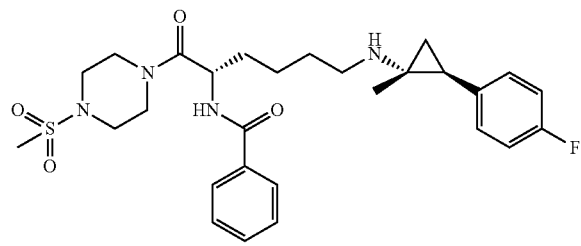 [SMILES: C[C@@]1(NCCCC[C@H](NC(=O)c2ccccc2)C(=O)N2CCN(S(C)(=O)=O)CC2)C[C@H]1c1ccc(F)cc1]

N—((S)-6-(((1R,2S)-2-(4-fluorophenyl)-1-methylcyclopropyl)amino)-1-(4-(methylsulfonyl)piperazin-1-yl)-1-oxohexan-2-yl)benzamide was prepared with a modification of the method that used that for N—((S)-1-oxo-6-(((1R,2S)-2-phenylcyclopropyl)amino)-1-(pyrrolidin-1-yl)hexan-2-yl)benzamide. The key alcohol intermediate (S)—N-(6-hydroxy-1-(4-(methylsulfonyl)piperazin-1-yl)-1-oxohexan-2-yl)benzamide was prepared in a slightly different manner than was described earlier. (2S)-2-amino-6-methoxy-6-oxohexanoic acid was first reacted with benzoyl chloride to give (S)-2-benzamido-6-methoxy-6-oxohexanoic acid. This was converted to the amide (S)-methyl 5-benzamido-6-(4-(methylsulfonyl)piperazin-1-yl)-6-oxohexanoate with 1-methane sulfonylpiperazine/HATU and DIEA. The ester was hydrolyzed with LiOH in methanol/water to yield the acid (S)-5-benzamido-6-(4-(methylsulfonyl)piperazin-1-yl)-6-oxohexanoic acid in 72% yield as a yellow solid. This was reduced with BH$_3$/THF to give the alcohol (S)—N-(6-hydroxy-1-(4-(methylsulfonyl)piperazin-1-yl)-1-oxohexan-2-yl)benzamide in 59% yield as a yellow oil. This was converted to the mesylate (S)—N-(1-(4-(methylsulfonyl)piperazin-1-yl)-1,6-dioxohexan-2-yl)benzamide using methane sulfonyl chloride and triethyl amine. The mesylate was a white solid. Yield was 40%. The mesylate was reacted in sn2 fashion with (S)-5-benzamido-6-(4-(methylsulfonyl)piperazin-1-yl)-6-oxohexanoic acid in the presence of DIEA/KI in acetonitrile to give N—((S)-6-(((1R,2S)-2-(4-fluorophenyl)-1-methylcyclopropyl)amino)-1-(4-(methylsulfonyl)piperazin-1-yl)-1-oxohexan-2-yl)benzamide as a white solid in 18% yield. ES, m/z=545 (M+H). 1H NMR (300 MHz, CDCl3, ppm): 7.80-7.83 (m, 2H), 7.51-7.53 (m, 3H), 7.07-7.12 (m, 2H), 6.92-7.01 (m, 1H), 5.13-5.18 (m, 1H), 3.88-4.05 (m, 2H), 3.43-3.92 (m, 4H), 3.09-3.21 (m, 2H), 2.72-2.80 (m, 5H), 2.12-2.17 (m, 1H), 1.50-1.89 (m, 6H), 0.81-1.11 (m, 4H)

N—((S)-1-oxo-6-(((1R,2S)-2-phenylcyclopropyl)amino)-1-(pyrrolidin-1-yl)hexan-2-yl)benzamide: This preparation is similar to that of N—((S)-1-oxo-6-(((1R,2S)-2-phenylcyclopropyl)amino)-1-(pyrrolidin-1-yl)hexan-2-yl)benzamide via Dess-Martin oxidation and reductive amination to form product. However, the synthesis of intermediate (S)—N-(6-hydroxy-1-(4-(methylsulfonyl)piperazin-1-yl)-1-oxohexan-2-yl)benzamide differed in that this method gave superior optical purity.

Example 9: N—((S)-6-(((1R,2S)-2-(4-fluorophenyl)cyclopropyl)amino)-1-(4-(methylsulfonyl)piperazin-1-yl)-1-oxohexan-2-yl)benzamide

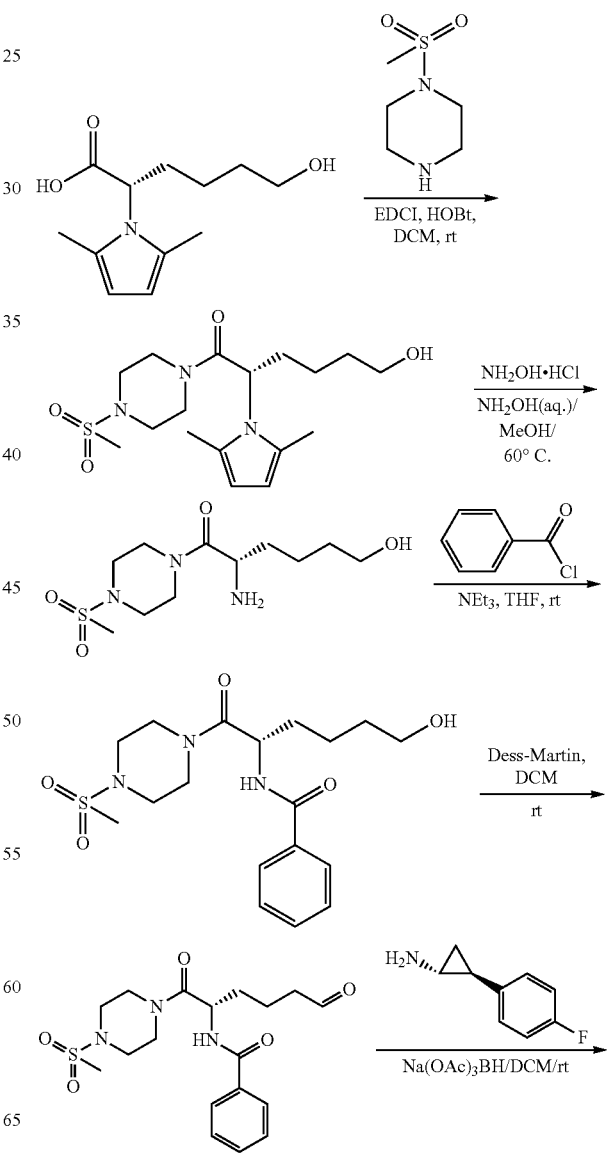

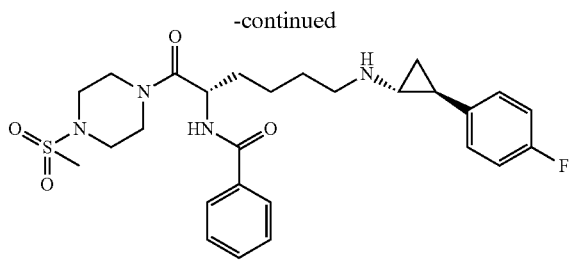

N—((S)-6-(((1R,2S)-2-(4-fluorophenyl)cyclopropyl)amino)-1-(4-(methylsulfonyl)piperazin-1-yl)-1-oxohexan-2-yl)benzamide. A solution of (S)-2-(2,5-dimethyl-1H-pyrrol-1-yl)-6-hydroxyhexanoic acid (820 mg, 3.64 mmol, 1.00 equiv) in dichloromethane 1-methanesulfonylpiperazine (2.18 g, 13.27 mmol, 3.00 equiv), 1-Ethyl-3-(3-dimethylaminopropyl)carbodiimide "EDCI" (1.7 g, 2.00 equiv) and hydroxybenzatriazole, "HOBT" (1.2 g, 2.00 equiv) was stirred for 1 h at room temperature. After the reaction was completed, the reaction was quenched with water and extracted with dichloromethane. The organic layers were washed with brine, dried over sodium sulfate, concentrated, and chromatographed on silica gel and eluted with ethyl acetate/petroleum ether (1:3). This resulted in 340 mg (25%) of (S)-2-(2,5-dimethyl-1H-pyrrol-1-yl)-6-hydroxy-1-(4-(methylsulfonyl)piperazin-1-yl)hexan-1-one as a yellow solid. A solution this material (440 mg, 1.18 mmol, 1.00 equiv) in ethanol was treated with a solution of NH$_2$OH.HCl (430 mg, 5.20 equiv) in water and NH$_2$OH (1.97 g, 28.70 equiv). The resulting solution was stirred for 6 days at 80° C. The reaction mixture was concentrated under vacuum and quenched with ice water. The pH was adjusted to pH 10 with aqueous NaOH and the mixture was extracted with ethyl acetate. The organics were concentrated and the residue chromatographed on silica gel and eluted with dichloromethane/methanol (10:1). This resulted in 210 mg (60%) of (S)-2-amino-6-hydroxy-1-(4-(methylsulfonyl) piperazin-1-yl)hexan-1-one as a solid. A 322 mg sample of this material (1.1 mmol, 1.0 equiv in tetrahydrofuran and NEt$_3$ (133 mg, 1.32 mmol, 1.20 equiv was reacted with a solution of benzoyl chloride (185 mg, 1.32 mmol, 1.20 equiv) in tetrahydrofuran at 0° C. during addition and stirred for 1 h at room temperature. The reaction mixture was diluted with water and extracted with ethyl acetate. The organic phase was washed with brine, dried, and concentrated. The residue was chromatographed on silica gel and eluted with ethyl acetate/petroleum ether (1:5). This resulted in 304 mg (70%) of (S)-2-amino-6-hydroxy-1-(4-(methylsulfonyl)piperazin-1-yl)hexan-1-one as colorless oil. This (S)-2-amino-6-hydroxy-1-(4-(methylsulfonyl)piperazin-1-yl)hexan-1-one was oxidized to the corresponding aldehyde in the manner described for N—((S)-1-oxo-6-4(1R,2S)-2-phenylcyclopropyl)amino)-1-(pyrrolidin-1-yl)hexan-2-yl)benzamide. Yield 66%. The resulting (S)—N-(1-(4-(methylsulfonyl)piperazin-1-yl)-1,6-dioxohexan-2-yl)benzamide was reacted with (1R,2S)-2-(4-fluorophenyl)cyclopropanamine under the reductive amination conditions described earlier to yield the desired N—((S)-6-(((1R,2S)-2-(4-fluorophenyl)cyclopropyl)amino)-1-(4-(methylsulfonyl)piperazin-1-yl)-1-oxohexan-2-yl)benzamide as a colorless oil, yield 14%. ES, m/z=457 (M+H). $^1$H NMR (300 MHz, CD$_3$OD-d$_4$) δ ppm: 7.86 (d, J=7.2 Hz, 2H), 7.43-7.60 (m, 3H), 6.90-7.12 (m, 4H), 5.03 (t, J=7.05 Hz, 1H), 3.89-4.03 (m, 2H), 3.62-3.77 (m, 1H), 3.45-3.58 (m, 1H), 3.33-3.45 (m, 2H), 3.20-3.330 (m, 1H), 3.08-3.20 (m, 1H), 2.87 (s, 3H), 2.73 (t, J=8.2 Hz, 2H), 2.25-2.32 (m, 1H), 1.78-1.95 (m, 3H), 1.40-1.68 (m, 4H), 0.92-1.08 (m, 2H).

Example 10: N—((S)-6-(((1R,2S)-2-(4-fluorophenyl)cyclopropyl)amino)-1-oxo-1-(piperidin-1-yl)hexan-7-yl)benzamide

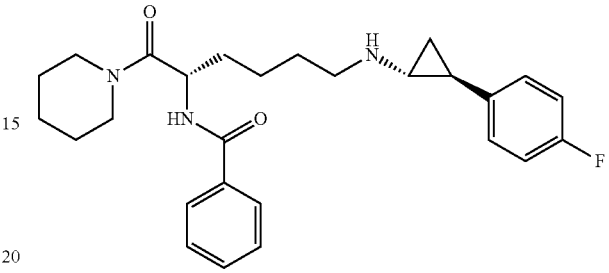

N—((S)-6-(((1R,2S)-2-(4-fluorophenyl)cyclopropyl)amino)-1-oxo-1-(piperidin-1-yl)hexan-2-yl)benzamide was prepared by the same method that was described for N—((S)-1-oxo-6-(((1R,2S)-2-phenylcyclopropyl)amino)-1-(pyrrolidin-1-yl)hexan-2-yl)benzamide. (S)-2-(2,5-dimethyl-1H-pyrrol-1-yl)-6-hydroxyhexanoic acid was reacted with piperidine/EDCl/HOBt to yield (S)-2-(2,5-dimethyl-1H-pyrrol-1-yl)-6-hydroxy-1-(piperidin-1-yl)hexan-1-one. This was deprotected with hydroxyl amine in methanol to yield (S)-2-amino-6-hydroxy-1-(piperidin-1-yl)hexan-1-one which could be reacted with benzoyl chloride and triethylamine to yield (S)—N-(6-hydroxy-1-oxo-1-(piperidin-1-yl)hexan-2-yl)benzamide. This alcohol was oxidized under Dess-Martin conditions to yield the aldehyde (S)—N-(1,6-dioxo-1-(piperidin-1-yl)hexan-2-yl)benzamide. The aldehyde was, in turn, coupled with (1R,2S)-2-(4-fluorophenyl)cyclopropanamine under reductive amination conditions (Na(OAc)$_3$BH) to yield the product N—((S)-6-(((1R,2S)-2-(4-fluorophenyl)cyclopropyl)amino)-1-oxo-1-(piperidin-1-yl)hexan-2-yl)benzamide as a light yellow oil. $^1$H NMR (300 MHz, CD$_3$OD-d$_4$) δ ppm: 7.92-7.83 (m, 2H), 7.60-7.45 (m, 3H), 7.12-7.00 (m, 2H), 7.00-6.90 (m, 2H), 5.07 (dd, J=8.1 Hz, 5.7 Hz, 1H), 3.75-3.42 (m, 4H), 2.72 (t, J=7.2 Hz, 2H), 2.31-2.25 (m, 1H), 1.95-1.40 (m, 13H), 1.10-0.90 (m, 2H); MS (ES, m/z): 452 (M+H).

Example 11: N—((S)-6-(((1R,2S)-2-(4-fluorophenyl)cyclopropyl)amino)-1-morpholino-1-oxohexan-2-yl)benzamide N—((S)-6-(((1R,2S)-2-(4-fluorophenyl)cyclopropyl)amino)-1-morpholino-1-oxohexan-2-yl)benzamide was prepared by the same method that was described for N—((S)-1-oxo-6-(((1R,2S)-2-phenylcyclopropyl)amino)-1-(pyrrolidin-1-yl)hexan-2-yl)benzamide. (S)-2-(2,5-dimethyl-1H-pyrrol-1-yl)-6-hydroxyhexanoic acid was reacted with morpholine/EDCl/HOBt to yield (S)-2-(2,5-dimethyl-1H-pyrrol-1-yl)-6-hydroxy-1-morpholinohexan-1-one with a 69% yield. This was deprotected with hydroxyl amine in methanol to yield (S)-2-amino-6-hydroxy-1-morpholinohexan-1-one which could be reacted with benzoyl chloride and triethylamine to yield (S)—N-(6-hydroxy-1-morpholino-1-oxohexan-2-yl)benzamide with a 63% yield on deprotection and 69% on amide formation. This alcohol was oxidized under Dess-Martin conditions to yield the aldehyde (S)—N-(1-morpholino-1,6-dioxohexan-2-yl)benzamide with a 70% yield. The aldehyde was, in turn, coupled with (1R,2S)-2-(4-fluorophenyl)cyclopropanamine under reductive amination conditions (Na(OAc)₃BH) to yield the product N—((S)-6-(((1R,2S)-2-(4-fluorophenyl)cyclopropyl)amino)-1-morpholino-1-oxohexan-2-yl)benzamide with a yield of 21% after purification by prep HPLC. ES, m/z=454 (M+H). ¹H NMR (300 MHz, CD₃OD-d₄) δ ppm: 7.85 (dd, J₁=5.1 Hz, J₂=1.8 Hz 2H), 7.83-7.45 (m, 3H), 7.09-7.04 (m, 2H), 6.98-6.92 (m, 2H), 5.03 (d, J=4.05 Hz, 1H), 3.72-3.67 (m, 8H), 2.72 (d, J=7.2 Hz, 2H), 2.29-2.27 (m, 1H), 0.95-1.90 (m, 10H)

Example 12: N—((S)-6-(((1R,2S)-2-(4-fluorophenyl)cyclopropyl)amino)-1-(4-methylpiperazin-1-yl)-1-oxohexan-2-yl)benzamide

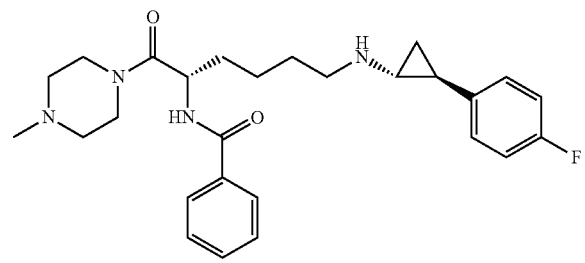 [SMILES: CN1CCN(C(=O)[C@H](CCCCN[C@@H]2C[C@H]2c2ccc(F)cc2)NC(=O)c2ccccc2)CC1]

N—((S)-6-(((1R,2S)-2-(4-fluorophenyl)cyclopropyl)amino)-1-(4-methylpiperazin-1-yl)-1-oxohexan-2-yl)benzamide was prepared by the same method that was described for N—((S)-1-oxo-6-(((1R,2S)-2-phenylcyclopropyl)amino)-1-(pyrrolidin-1-yl)hexan-2-yl)benzamide. (S)—N-(6-hydroxy-1-(4-methylpiperazin-1-yl)-1-oxohexan-2-yl)benzamide was prepared in the usual way. This alcohol was oxidized under Dess-Martin conditions to yield the aldehyde (S)—N-(1-(4-methylpiperazin-1-yl)-1,6-dioxohexan-2-yl)benzamide as a yellow solid with a 75% yield. The aldehyde was, in turn, coupled with (1R,2S)-2-(4-fluorophenyl)cyclopropanamine under reductive amination conditions (Na(OAc)₃BH) to yield the product N—((S)-6-(((1R,2S)-2-(4-fluorophenyl)cyclopropyl)amino)-1-(4-methylpiperazin-1-yl)-1-oxohexan-2-yl)benzamide with a yield of 3% after purification by prep HPLC on a chiral column. ES, m/z=467 (M+1). H-NMR: (CD3OD, ppm): 7.86-7.85 (d, J=1.8 Hz, 2H), 7.59-7.52 (m, 1H), 7.50-7.41 (m, 2H), 7.12-7.01 (m, 2H), 6.98-6.88 (t, J=8.7 Hz, 2H), 5.01-5.12 (d, J=6 Hz, 1H), 3.86-3.69 (m, 2H), 3.67-3.43 (m, 2H), 2.66-2.78 (m, 2H), 2.56-2.39 (m, 4H), 2.34-2.21 (m, 4H), 1.98-1.73 (m, 3H), 1.64-1.38 (m, 4H), 0.91-1.11 (m, 2H)

Example 13: 4-fluoro-N—((S)-6-(((1R,2S)-2-(4-fluorophenyl)cyclopropyl)amino)-1-oxo-1-(piperidin-1-yl)hexan-2-yl)

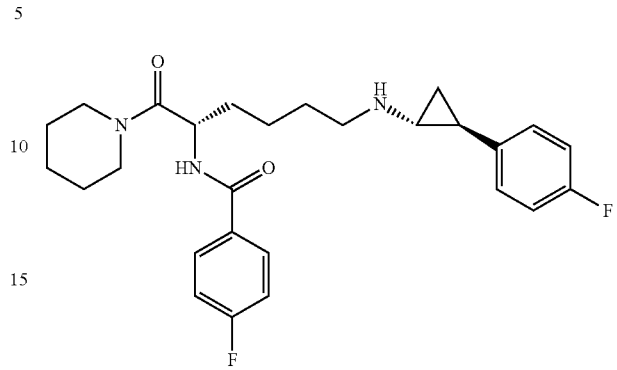

4-fluoro-N—((S)-6-(((1R,2S)-2-(4-fluorophenyl)cyclopropyl)amino)-1-oxo-1-(piperidin-1-yl)hexan-2-yl) (S)-4-fluoro-N-(6-hydroxy-1-oxo-1-(piperidin-1-yl)hexan-2-yl)benzamide was prepared in a manner similar to that exemplified in the synthesis of N—((S)-1-oxo-6-(((1R,2S)-2-phenylcyclopropyl)amino)-1-(pyrrolidin-1-yl)hexan-2-yl)benzamide. The alcohol precursor (S)-4-fluoro-N-(6-hydroxy-1-oxo-1-(piperidin-1-yl)hexan-2-yl)benzamide was oxidized under des-Martin conditions and the resultant aldehyde was coupled with (1R,2S)-2-(4-fluorophenyl)cyclopropanamine under the usual reductive amination conditions to yield the desired product 4-fluoro-N—((S)-6-(((1R,2S)-2-(4-fluorophenyl)cyclopropyl)amino)-1-oxo-1-(piperidin-1-yl)hexan-2-yl) as a colorless oil. ES, m/z=470 (M+H). ¹H NMR (300 MHz, CD₃OD-d₄) δ ppm: 7.91-7.74 (m, 2H), 7.20 (m, 2H), 7.01-7.12 (m, 2H), 6.94 (t, 2H), 5.05 (t, J=6.9 Hz, 1H), 3.42-3.73 (m, 4H), 2.73 (t, J=7.2 Hz, 2H), 2.25-2.33 (m, 1H), 1.52-1.97 (m, 13H), 0.92-1.08 (m, 2H)

Example 14: N—((S)-6-(((1R,2S)-2-(4-fluorophenyl)cyclopropyl)amino)-1-oxo-1-(piperidin-1-yl)hexan-2-yl)-4-(trifluoromethyl)benzamide

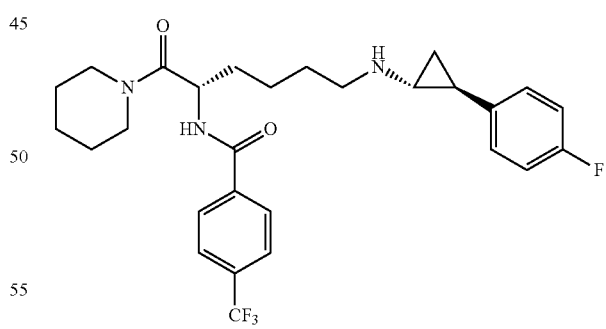

N—((S)-6-(((1R,2S)-2-(4-fluorophenyl)cyclopropyl)amino)-1-oxo-1-(piperidin-1-yl)hexan-2-yl)-4-(trifluoromethyl)benzamide was prepared in a manner similar to that exemplified in the synthesis of N—((S)-1-oxo-6-(((1R,2S)-2-phenylcyclopropyl)amino)-1-(pyrrolidin-1-yl)hexan-2-yl)benzamide. The alcohol (S)—N-(6-hydroxy-1-oxo-1-(piperidin-1-yl)hexan-2-yl)-4-(trifluoromethyl)benzamide was oxidized under des-Martin conditions and the resultant aldehyde (S)—N-(1,6-dioxo-1-(piperidin-1-yl)hexan-2-yl)-4-(trifluoromethyl)benzamide was coupled with (1R,2S)-2-(4-fluorophenyl)cyclopropanamine under the usual reductive amination conditions to yield the desired product N—((S)-6-(((1R,2S)-2-(4-fluorophenyl)cyclopropyl)amino)-1-oxo-1-(piperidin-1-yl)hexan-2-yl)-4-(trifluoromethyl)benzamide as an off-white semi-solid. ES, m/z=520 (M+1). H-NMR (CD₃OD, ppm): 8.14-7.89 (m, 2H), 7.88-7.71 (d, J=7.5 Hz, 2H), 7.26-6.83 (m, 4H), 5.13 (s, 1H), 3.59-3.81 (m, 2H), 3.58-3.38 (m, 2H), 3.02-2.71 (b, 2H), 2.62-2.33 (b, 1H), 2.21-1.95 (b, 1H), 1.91-1.36 (m, 12H), 1.27-1.11 (m, 2H).

Example 15: N—((S)-6-(((1R,2S)-2-(4-fluorophenyl)cyclopropyl)amino)-1-oxo-1-(piperidin-1-yl)hexan-2-yl)-[1,1'-biphenyl]-4-carboxamide

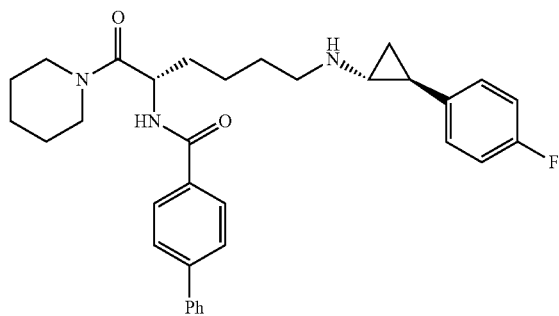 [SMILES: O=C(N[C@@H](CCCCN[C@@H]1C[C@H]1c1ccc(F)cc1)C(=O)N1CCCCC1)c1ccc(-c2ccccc2)cc1]

N—((S)-6-(((1R,2S)-2-(4-fluorophenyl)cyclopropyl)amino)-1-oxo-1-(piperidin-1-yl)hexan-2-yl)-[1,1'-biphenyl]-4-carboxamide was prepared by the same method that was described for N—((S)-1-oxo-6-(((1R,2S)-2-phenylcyclopropyl)amino)-1-(pyrrolidin-1-yl)hexan-2-yl)benzamide. (S)-2-amino-6-hydroxy-1-(piperidin-1-yl)hexan-1-one was reacted with 4-phenylbenzoyl chloride and triethylamine to yield (S)—N-(1,6-dioxo-1-(piperidin-1-yl)hexan-2-yl)-[1,1'-biphenyl]-4-carboxamide. This alcohol was oxidized under Dess-Martin conditions to yield the aldehyde (S)—N-(1,6-dioxo-1-(piperidin-1-yl)hexan-2-yl)-[1,1'-biphenyl]-4-carboxamide. The aldehyde was, in turn, coupled with (1R,2S)-2-(4-fluorophenyl)cyclopropanamine under reductive amination conditions (Na(OAc)₃BH) to yield the product N—((S)-6-(((1R,2S)-2-(4-fluorophenyl)cyclopropyl)amino)-1-oxo-1-(piperidin-1-yl)hexan-2-yl)-[1,1'-biphenyl]-4-carboxamide as a colorless oil. ES, m/z: 528 (M+1). H-NMR: (CD₃OD, ppm): 7.94 (d, J=8.4 Hz, 2H), 7.90-7.65 (m, 4H), 7.60-7.35 (m, 3H), 7.20-7.00 (m, 2H), 7.00-6.90 (m, 2H), 5.12 (t, J=7.2 Hz, 1H), 3.85-3.40 (m, 4H), 2.74 (t, J=7.2 Hz, 1H), 2.40-2.30 (m, 1H), 2.00-1.45 (m, 13H), 1.15-0.85 (m, 2H).

Example 16: N—((S)-1-(1,1-dioxidothiomorpholino)-6-(((1R,2S)-2-(4-fluorophenyl)cyclopropyl)amino)-1-oxohexan-2-yl)benzamide

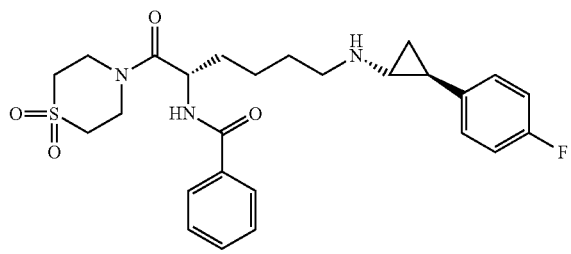

N—((S)-1-(1,1-dioxidothiomorpholino)-6-(((1R,2S)-2-(4-fluorophenyl)cyclopropyl)amino)-1-oxohexan-2-yl)benzamide was prepared in a manner similar to that described for N—((S)-1-oxo-6-(((1R,2S)-2-phenylcyclopropyl)amino)-1-(pyrrolidin-1-yl)hexan-2-yl)benzamide. Dess-Martin oxidation resulted in 80 mg (80%) of N-[(2S)-1-(1,1-dioxo-1[6],4-thiomorpholin-4-yl)-1,6-dioxohexan-2-yl]benzamide as a yellow solid. Coupling under reductive amination conditions with (1R,2S)-2-(4-fluorophenyl)cyclopropanamine yielded the desired product in 24% yield as an off white solid. ES, m/z=502 (M+1). H-NMR–:(DMSO-d6, ppm): 8.90 (d, J=7.2 Hz, 2H), 7.89 (d, J=7.2 Hz, 2H), 7.46 (d, J=7.2 Hz, 2H), 7.15-6.90 (m, 4H), 4.95-4.80 (m, 1H), 4.28-4.05 (m, 2H), 3.95-3.80 (m, 1H), 3.75-3.55 (m, 1H), 3.38-3.12 (m, 3H), 3.12-2.95 (m, 1H), 2.70-2.45 (m, 2H), 2.25-2.15 (m, 1H), 1.85-1.60 (m, 3H), 1.55-1.30 (m, 4H), 1.00-0.80 (m, 2H).

Example 17: 4-fluoro-N—((R)-3-((2-(((1R,2S)-2-(4-fluorophenyl)-1-methylcyclopropyl)amino)ethyl)sulfonyl)-1-morpholino-1-oxopropan-2-yl)benzamide Reaction Scheme for SO₂-Linker

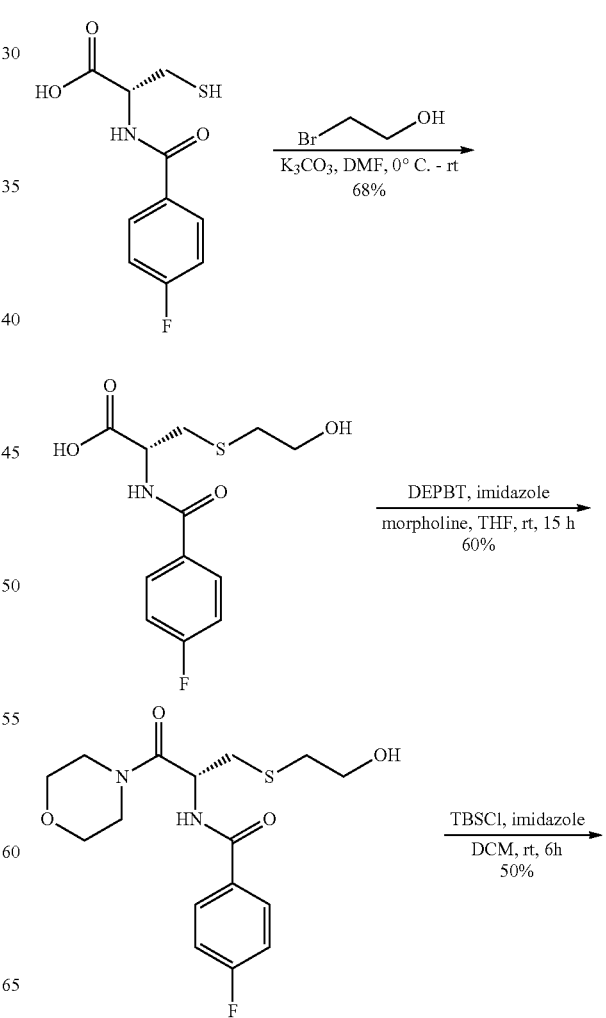

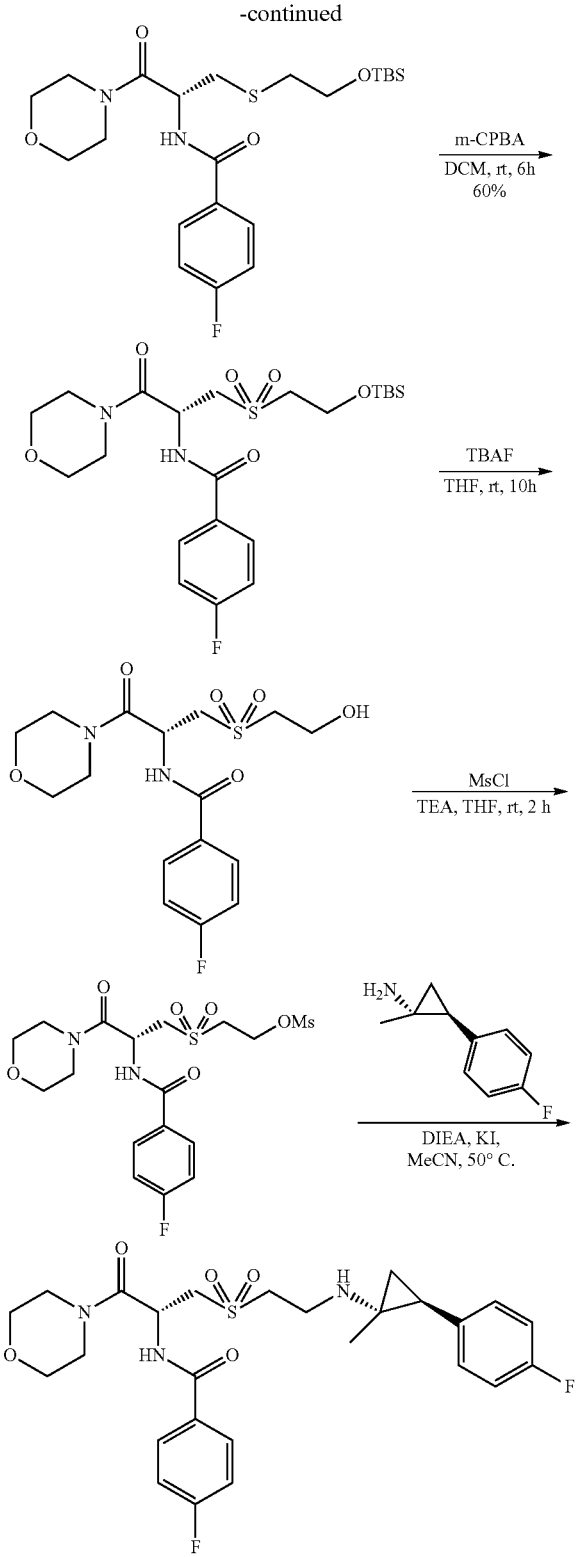

4-fluoro-N—((R)-3-((2-(((1R,2S)-2-(4-fluorophenyl)-1-methylcyclopropyl)amino)ethyl)sulfonyl)-1-morpholino-1-oxopropan-2-yl)benzamide.

A solution of (R)-2-(4-fluorobenzamido)-3-mercaptopropanoic acid (5 g, 20.55 mmol) in N,N-dimethylformamide (50 mL) was stirred with potassium methaneperoxoate (5.7 g, 40.94 mmol). This was followed by the addition of a solution of 2-bromoethan-1-ol (2.8 g, 22.41 mmol) in N,N-dimethylformamide (20 mL) dropwise with stirring at 0° C. The resulting solution was stirred for 5 h at room temperature. The resulting solution was diluted with 200 mL of H₂O. The pH value of the solution was adjusted to 3 with hydrochloric acid (2 mol/L). The resulting solution was extracted with ethyl acetate and the organic layers combined and dried over anhydrous sodium sulfate and concentrated under vacuum. The residue was chromatographed on silica gel and eluted with dichloromethane/methanol (20:1). This resulted in 4 g (68%) of (R)-2-(4-fluorobenzamido)-3-((2-hydroxyethyl)thio)propanoic acid as yellow oil. (R)-4-fluoro-N-(3-((2-hydroxyethyl)thio)-1-morpholino-1-oxopropan-2-yl)benzamide as yellow oil. To a solution of (R)-2-(4-fluorobenzamido)-3-((2-hydroxyethyl)thio)propanoic acid (4 g, 13.92 mmol, 1.00 equiv) in tetrahydrofuran (50 mL), was added 3-(diethoxyphosphoryloxy)-1,2,3-benzotriazin-4(3H)-one (DEPBT) (6.25 g, 20.90 mmol, 1.50 equiv) and imidazole (1.42 g, 20.88 mmol, 1.50 equiv). The mixture was stirred for 30 minutes at 0° C. Then morpholine (1.2 g, 13.77 mmol, 0.99 equiv) was added. The resulting solution was stirred for 12 h at room temperature. The resulting solution was diluted with 200 mL of ethyl acetate. The resulting mixture was washed with brine. The organic layers was dried over anhydrous sodium sulfate and concentrated under vacuum. The residue was chromatographed on silica gel and eluted with ethyl acetate/petroleum ether (1:10). This resulted in 3 g (60%) of the desired product. To a solution of this (R)-4-fluoro-N-(3-((2-hydroxyethyl)thio)-1-morpholino-1-oxopropan-2-yl)benzamide (3 g, 8.42 mmol, 1.00 equiv) in dichloromethane (30 mL) and imidazole (1.14 g, 16.76 mmol, 1.99 equiv) was added tert-butyldimethylsilyl chloride "TBSCl" (1.9 g, 12.58 mmol, 1.49 equiv), dropwise at 0° C. The resulting solution was stirred for 6 h at room temperature. The reaction was then quenched by the addition of water. The resulting solution was extracted with dichloromethane and the organic layers combined and dried over anhydrous sodium sulfate and concentrated under vacuum. The residue was chromatographed on silica gel and eluted with ethyl acetate/petroleum ether (1:30). This resulted in 2 g (50%) of (R)—N-(3-((2-((tert-butyldimethylsilyl)oxy)ethyl)thio)-1-morpholino-1-oxopropan-2-yl)-4-fluorobenzamide which was white solid. A solution of (R)—N-(3-((2-((tert-butyldimethylsilyl)oxy)ethyl)thio)-1-morpholino-1-oxopropan-2-yl)-4-fluorobenzamide (2 g, 4.25 mmol, 1.00 equiv) and meta-chloroperbenzoic acid, "m-CPBA" (1.84 g, 10.66 mmol, 2.51 equiv) was for 6 h at room temperature. This was diluted with of DCM. The resulting mixture was washed with of saturated sodium bicarbonate solution. This was washed with of brine. The organic layers was dried over anhydrous sodium sulfate and concentrated under vacuum. The residue was chromatographed column with ethyl acetate/petroleum ether (1:30). This resulted in 1.3 g (61%) of (R)—N-(3-((2-((tert-butyldimethylsilyl)oxy)ethyl)sulfonyl)-1-morpholino-1-oxopropan-2-yl)-4-fluorobenzamide as a white solid. This was dissolved in THF and treated with tetrabutylammonium fluoride, "TBAF" with stirring for 10 h. The reaction was diluted with ethyl acetate and washed with brine. The mixture was dried over anhydrous sodium sulfate and concentrated under vacuum. The residue was chromatographed on a silica gel column and eluted with ethyl acetate/petroleum ether (1:20). This resulted in 300 mg (78%) of (R)-4-fluoro-N-(3-((2-hydroxyethyl)sulfonyl)-1-morpholino-1-oxopropan-2-yl)benzamide as yellow oil. This alcohol was converted to the mesylate with methanesulfonyl chloride, "MsCl" and triethyl amine and the mesylate was reacted with (1R,2S)-2-(4-fluorophenyl)-1-methylcyclopropanamine to yield 4-fluoro-N—((R)-3-((2-(((1R,2S)-2-(4-fluorophenyl)-1-methylcyclopropyl)amino)ethyl)sulfonyl)-1-morpholino-1-oxopropan-2-yl)benzamide in a 28% yield as a white solid. ES, m/z: [M+H]=536; H-NMR (400 MHz, CDCl$_3$): δ 7.87~7.82 (m, 2H), 7.17~7.07 (m, 4H), 0.99~6.95 (m, 2H), 5.70~5.65 (m, 1H), 3.81~3.64 (m, 10H), 3.42~3.50 (m, 1H), 3.39~3.33 (m, 3H), 2.22~2.30 (m, 1H), 1.10~1.20 (m, 1H), 1.00 (s, 3H), 0.90~0.87 (m, 1H).

Example 18: 4-fluoro-N—((R)-3-((2-(((1R,2S)-2-(4-methoxyphenyl)cyclopropyl)amino)ethyl)sulfonyl)-1-morpholino-1-oxopropan-2-yl)benzamide

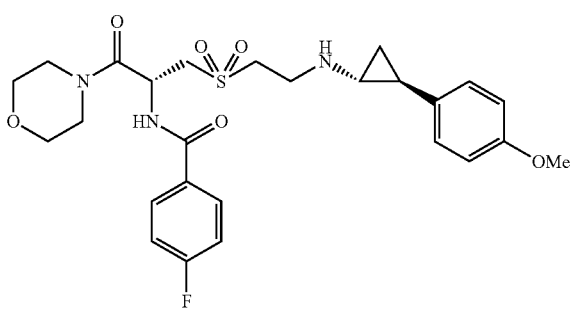 [SMILES: COc1ccc([C@@H]2C[C@H]2NCCS(=O)(=O)C[C@H](NC(=O)c2ccc(F)cc2)C(=O)N2CCOCC2)cc1]

The method that was described for the synthesis of 4-fluoro-N—((R)-3-((2-(((1R,2S)-2-(4-fluorophenyl)-1-methylcyclopropyl)amino)ethyl)sulfonyl)-1-morpholino-1-oxopropan-2-yl)benzamide was used in the preparation of 4-fluoro-N—((R)-3-((2-(((1R,2S)-2-(4-methoxyphenyl)cyclopropyl)amino)ethyl)sulfonyl)-1-morpholino-1-oxopropan-2-yl)benzamide. The mesylate, 4-fluoro-N—((R)-3-((2-(((1R,2S)-2-(4-methoxyphenyl)cyclopropyl)amino)ethyl)sulfonyl)-1-morpholino-1-oxopropan-2-yl)benzamide, was prepared by the methods described earlier. The mesylate was reacted with (1R,2S)-2-(4-methoxyphenyl)cyclopropanamine in the presence of DIEA/KI in acetonitrile at 50 degrees to give the desired 4-fluoro-N—((R)-3-((2-(((1R,2S)-2-(4-methoxyphenyl)cyclopropyl)amino)ethyl)sulfonyl)-1-morpholino-1-oxopropan-2-yl)benzamide as a white solid. ES, m/z=534 (M+H). H-NMR (300 MHz, CDCl$_3$): δ 7.86~7.81 (m, 2H), 7.12~7.07 (m, 2H), 6.97~6.94 (m, 2H), 6.81~6.78 (m, 2H), 5.67~5.64 (m, 1H), 3.80~3.77 (m, 4H), 3.71~3.58 (m, 11H), 3.42~3.38 (m, 2H), 2.48~2.42 (m, 1H), 2.20~2.10 (m, 1H), 2.28~4.23 (m, 1H), 1.03~1.00 (m, 1H).

Example 19: 4-fluoro-N—((R)-3-((2-(((1R,2S)-2-(4-fluorophenyl)cyclopropyl)amino)ethyl)sulfonyl)-1-morpholino-1-oxopropan-2-yl)benzamide

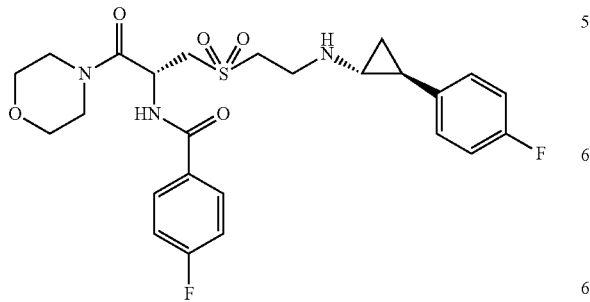

4-fluoro-N—((R)-3-((2-(((1R,2S)-2-(4-fluorophenyl)cyclopropyl)amino)ethyl)sulfonyl)-1-morpholino-1-oxopropan-2-yl)benzamide was prepared by the method used to prepare 4-fluoro-N—((R)-3-((2-(((1R,2S)-2-(4-fluorophenyl)-1-methylcyclopropyl)amino)ethyl)sulfonyl)-1-morpholino-1-oxopropan-2-yl)benzamide. The mesylate (R)-2-((2-(4-fluorobenzamido)-3-morpholino-3-oxopropyl)sulfonyl)ethyl methanesulfonate was prepared as described earlier. This was reacted with (1R,2S)-2-(4-fluorophenyl)cyclopropanamine and DIEA/KI in acetonitrile at 50 degrees to yield 4-fluoro-N—((R)-3-((2-(((1R,2S)-2-(4-fluorophenyl)cyclopropyl)amino)ethyl)sulfonyl)-1-morpholino-1-oxopropan-2-yl)benzamide as a white solid. ES, m/z:=522 (M+H). H-NMR (300 MHz, CDCl$_3$): δ 7.85~7.81 (m, 2H), 7.14~7.08 (m, 2H), 7.00~6.90 (m, 4H), 5.69~5.62 (m, 1H), 3.79~3.54 (m, 12H), 3.40~3.35 (m, 2H), 2.44~2.42 (m, 1H), 2.18~2.14 (m, 1H), 1.28~1.23 (m, 1H), 1.09~1.03 (m, 1H).

Example 20: 4-fluoro-N—((S)-3-(2-(((1R,2S)-2-(4-fluorophenyl)cyclopropyl)amino)ethoxy)-1-morpholino-1-oxopropan-2-yl)benzamide Reaction Scheme for Oxygen-Linked Compounds:

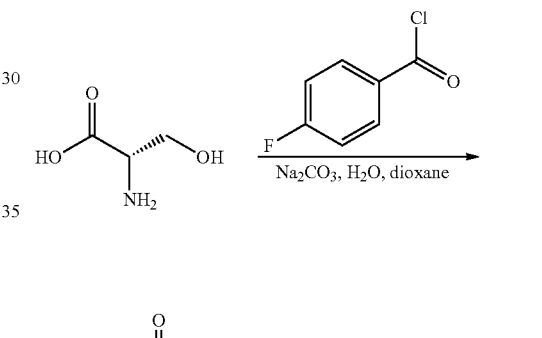

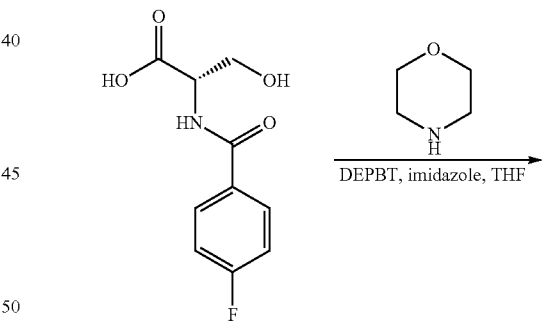

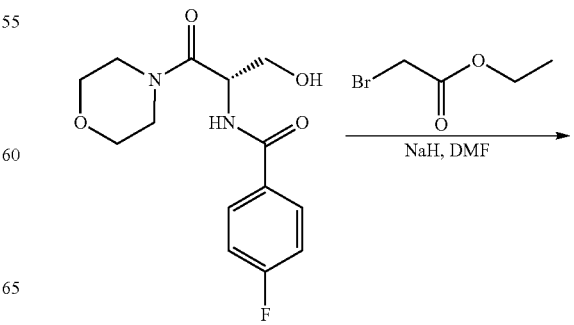

61

-continued

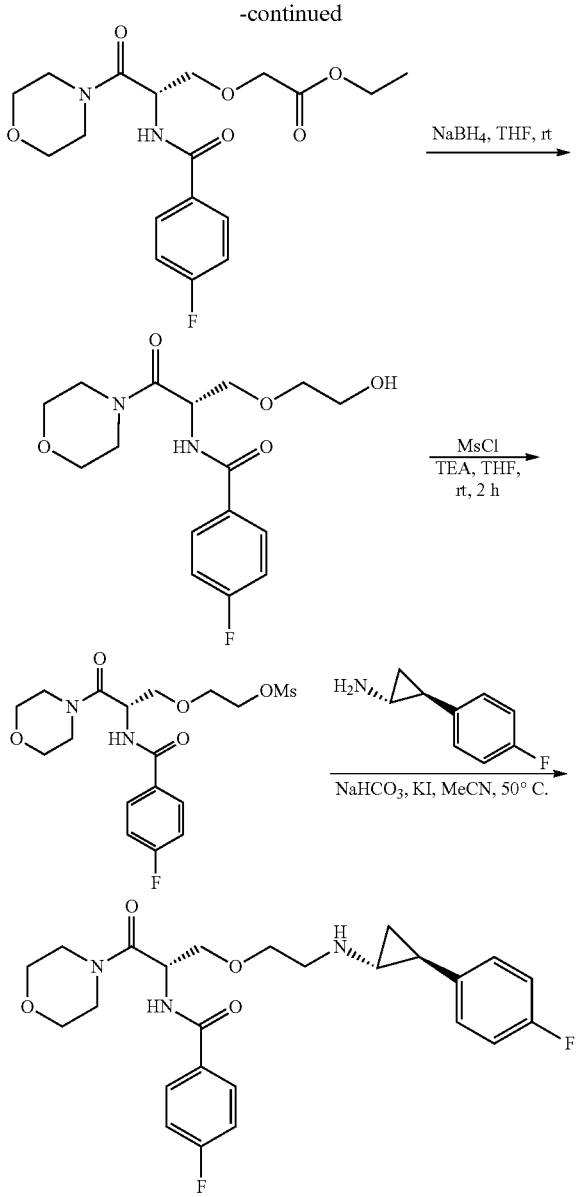

A solution of (2S)-2-amino-3-hydroxypropanoic acid (21 g, 199.82 mmol, 1.00 equiv) in H₂O/dioxane (450/210 mL) was treated with sodium carbonate in water. To this was added a solution of 4-fluorobenzoyl chloride in dioxane at 0° C. The solution was stirred for 1 h at 0° C. The reaction was extracted with ethyl acetate. The water layers were acidified and extracted with ethyl acetate. The organic layers were washed with brine and dried over anhydrous sodium sulfate and concentrated to yield 45 g (99%) of (S)-2-(4-fluorobenzamido)-3-hydroxypropanoic acid as a white solid. The material (4 g) was dissolved in tetrahydrofuran and treated with 3-(diethoxyphosphoryloxy)-1,2,3-benzotriazin-4(3H)-one, (DEPBT) (10.54 g, 2.00 equiv) and imidazole (2.4 g, 2.00 equiv), and, after stirring 30 min, morpholine (1.53 g, 17.56 mmol, 1.00 equiv) in tetrahydrofuran at 0° C. and then at RT for 16. The reaction was diluted with 150 mL of KH₂PO₄(aq.) and extracted with ethyl acetate. The organics were washed with brine and dried over anhydrous sodium sulfate. After concentration, the residue was chromatographed on silica gel and eluted with 10/1 dichloromethane/

62 methanol (10:1). This resulted in 800 mg (15%) of (S)-4-fluoro-N-(3-hydroxy-1-morpholino-1-oxopropan-2-yl) benzamide as a yellow oil. This was dissolved in DMF and treated with sodium hydride (130 mg, 5.42 mmol, 2.00 equiv) at 0° C. The mixture was stirred for 30 min at 25° C. This was followed by the addition of a solution of ethyl 2-bromoacetate (903 mg, 5.41 mmol, 2.00 equiv) in N,N-dimethylformamide at 0° C. The resulting solution was stirred for 16 h at 25° C. The reaction was then quenched by the addition of 10 mL of water/ice. The resulting solution was diluted with H₂O and extracted with ethyl acetate. After a brine wash, the organics were dried and concentrated and then chromatographed on silica gel and eluted with ethyl acetate/petroleum ether (1:1). This resulted in 500 mg (48%) of (S)-ethyl 2-(2-(4-fluorobenzamido)-3-morpholino-3-oxopropoxy)acetate as a light yellow oil. This was dissolved in THF and treated with NaBH₄ (100 mg, 2.64 mmol, 2.00 equiv at 0° C. The resulting solution was stirred for 16 h at 25° C. The reaction was quenched with water/ice and extracted with ethyl acetate. The organics were washed with brine, dried over sodium sulfate, concentrated, and chromatographed on silica gel and eluted with ethyl acetate/petroleum ether (1:0). This resulted in 350 mg (79%) of (S)-4-fluoro-N-(3-(2-hydroxyethoxy)-1-morpholino-1-oxopropan-2-yl)benzamide as colorless oil. This was converted to the mesylate using MsCl/TEA/THF in the usual way (81% as an off white solid) and the mesylate was reacted with (1R,2S)-2-(4-fluorophenyl)cyclopropanamine to yield the desired 4-fluoro-N—((S)-3-(2-(((1R,2S)-2-(4-fluorophenyl)cyclopropyl)amino)ethoxy)-1-morpholino-1-oxopropan-2-yl)benzamide as a light yellow oil (12%). ES, m/z=474 (M+H). ¹H NMR (300 MHz, CD₃OD-d₄) δ ppm: 7.76 (dd, J₁=5.4 Hz, J₂=8.4 Hz, 2H), 7.16 (d, J=7.5 Hz, 1H), 7.04 (t, J=8.4 Hz, 2H), 7.4-6.85 (m, 4H), 5.22 (dd, J₁=7.2 Hz, J₂=12.6 Hz, 1H), 3.90-3.48 (m, 12H), 2.84 (t, J=5.1 Hz, 2H), 2.40-2.25 (m, 1H), 2.05-1.80 (m, 1H), 1.03-0.99 (m, 1H), 0.95-0.80 (m, 1H)

Example 21: 4-fluoro-N—((S)-3-(2-(((1R,2S)-2-(4-fluorophenyl)cyclopropyl)amino)acetamido)-1-morpholino-1-oxopropan-2-yl)benzamide Reaction Scheme for Amine-Linked Compounds

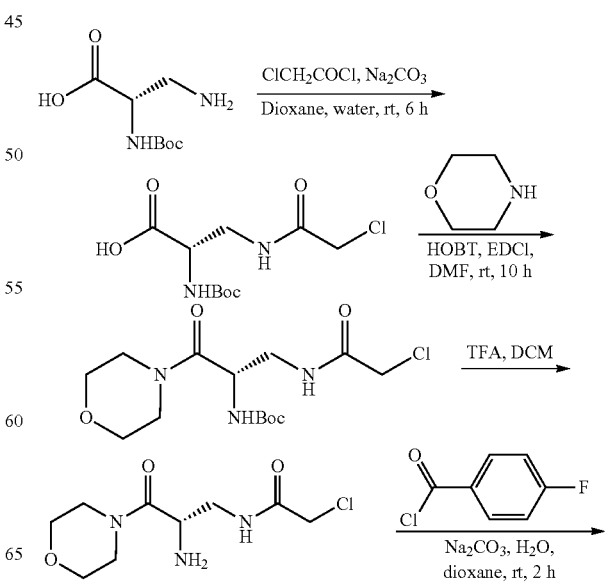

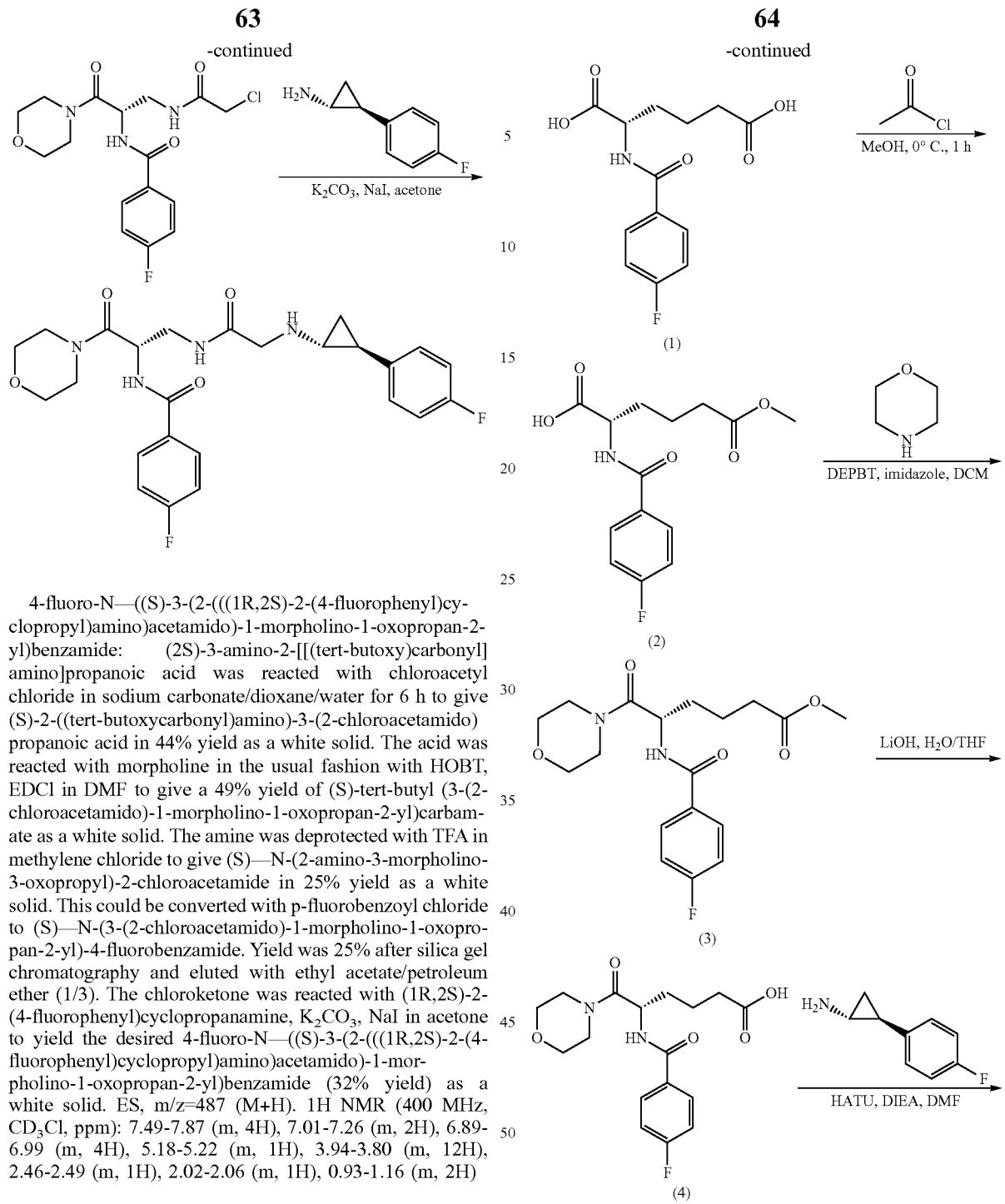

4-fluoro-N—((S)-3-(2-(((1R,2S)-2-(4-fluorophenyl)cy-clopropyl)amino)acetamido)-1-morpholino-1-oxopropan-2-yl)benzamide: (2S)-3-amino-2-[[(tert-butoxy)carbonyl]amino]propanoic acid was reacted with chloroacetyl chloride in sodium carbonate/dioxane/water for 6 h to give (S)-2-((tert-butoxycarbonyl)amino)-3-(2-chloroacetamido)propanoic acid in 44% yield as a white solid. The acid was reacted with morpholine in the usual fashion with HOBT, EDCl in DMF to give a 49% yield of (S)-tert-butyl (3-(2-chloroacetamido)-1-morpholino-1-oxopropan-2-yl)carbamate as a white solid. The amine was deprotected with TFA in methylene chloride to give (S)—N-(2-amino-3-morpholino-3-oxopropyl)-2-chloroacetamide in 25% yield as a white solid. This could be converted with p-fluorobenzoyl chloride to (S)—N-(3-(2-chloroacetamido)-1-morpholino-1-oxopropan-2-yl)-4-fluorobenzamide. Yield was 25% after silica gel chromatography and eluted with ethyl acetate/petroleum ether (1/3). The chloroketone was reacted with (1R,2S)-2-(4-fluorophenyl)cyclopropanamine, K₂CO₃, NaI in acetone to yield the desired 4-fluoro-N—((S)-3-(2-(((1R,2S)-2-(4-fluorophenyl)cyclopropyl)amino)acetamido)-1-morpholino-1-oxopropan-2-yl)benzamide (32% yield) as a white solid. ES, m/z=487 (M+H). 1H NMR (400 MHz, CD₃Cl, ppm): 7.49-7.87 (m, 4H), 7.01-7.26 (m, 2H), 6.89-6.99 (m, 4H), 5.18-5.22 (m, 1H), 3.94-3.80 (m, 12H), 2.46-2.49 (m, 1H), 2.02-2.06 (m, 1H), 0.93-1.16 (m, 2H)

Example 22: 4-fluoro-N—((S)-6-(((1R,2S)-2-(4-fluorophenyl)cyclopropyl)amino)-1-morpholino-1,6-dioxohexan-2-yl)benzamide

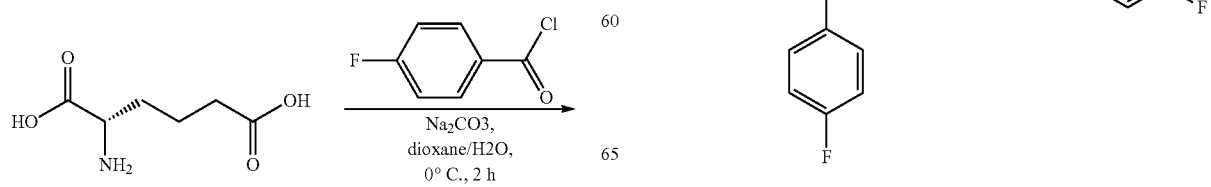

Step 1. (S)-2-(4-fluorobenzamido)hexanedioic Acid (1)

In a 1000-mL round-bottom flask, was placed a solution of (2S)-2-aminohexanedioic acid (10 g, 62.05 mmol, 1.00 equiv) in hydrogen chloride (0.5 mol/L) (250 mL). Then dioxane (80 mL) was added. This was followed by the addition of a solution of sodium carbonate (23.1 g, 3.50 equiv) in water (60 mL) and a solution of 4-fluorobenzoyl chloride (11.8 g, 74.42 mmol, 1.20 equiv) in dioxane (20 mL) were added dropwise with stirring at 0° C. at the same time. The resulting solution was stirred for 1 h at 0° C. in a water/ice bath. After the reaction was completed, the resulting solution was extracted with 2×400 mL of ethyl acetate. Then the pH value of the aqueous layers was adjusted to 2 with hydrogen chloride (1 mol/L). The aqueous layers were extracted with 3×400 mL of ethyl acetate and the organic layers combined. The organic layers were washed with 1×1000 mL of brine and dried over anhydrous sodium sulfate. After filtration, solvent was removed under reduced pressure. The residue was washed with 1×100 mL of DCM. This resulted in 11 g (63%) of (S)-2-(4-fluorobenzamido)hexanedioic acid as a white solid.

Step 2. (S)-2-(4-fluorobenzamido)-6-methoxy-6-oxohexanoic Acid (2)

Into a 1000-mL round-bottom flask, was placed a solution of (S)-2-(4-fluorobenzamido)hexanedioic acid (10 g, 35.30 mmol, 1.00 equiv) in methanol (360 mL). This was followed by the addition of acetyl chloride (3.3 g, 42.04 mmol, 1.20 equiv) dropwise with stirring at 0° C. in 30 min. The resulting solution was stirred for 60 min at 0° C. After the reaction was completed, $Na_2CO_3$(aq.) was added to the reaction. The resulting solution was extracted with 3×300 mL of ethyl acetate and then. Then the pH value of the aqueous layers were adjusted to 2 with hydrogen chloride (1 mol/L). The aqueous layers were extracted with 3×400 mL of ethyl acetate and the organic layers combined. The organic layers were washed with 1×1000 mL of brine and dried over anhydrous sodium sulfate. After filtration, solvent was removed under reduced pressure. This resulted in 6.4 g (61%) of (S)-2-(4-fluorobenzamido)-6-methoxy-6-oxohexanoic acid as colorless oil

Step 3. (S)-methyl 5-(4-fluorobenzamido)-6-morpholino-6-oxohexanoate (3)

Into a 250-mL 3-necked round-bottom flask, was placed a solution of (S)-2-(4-fluorobenzamido)-6-methoxy-6-oxohexanoic acid (3.5 g, 11.77 mmol, 1.00 equiv) in tetrahydrofuran (90 mL), DEPBT (7 g, 23.41 mmol, 2.00 equiv) and imidazole (1.6 g, 2.00 equiv). The mixture solution was stirred for 30 min at 0° C. To this was added a solution of morpholine (1 g, 11.48 mmol, 1.00 equiv) in tetrahydrofuran (30 mL) dropwise with stirring at 0° C. in 30 min. The resulting solution was stirred for 16 h at room temperature. The resulting solution was diluted with 150 mL of $KH_2PO_4$ (aq.). The resulting solution was extracted with 3×150 mL of ethyl acetate and the organic layers combined. The resulting mixture was washed with 1×300 mL of brine. The mixture was dried over anhydrous sodium sulfate and concentrated under vacuum. The residue was applied onto a silica gel column with ethyl acetate/petroleum ether (1:1). This resulted in 1.7 g (39%) of (S)-methyl 5-(4-fluorobenzamido)-6-morpholino-6-oxohexanoate as yellow oil

Step 4. (S)-5-(4-fluorobenzamido)-6-morpholino-6-oxohexanoic Acid (4)

Into a 100-mL round-bottom flask, was placed a solution of (S)-methyl 5-(4-fluorobenzamido)-6-morpholino-6-oxohexanoate (1.6 g, 4.37 mmol, 1.00 equiv) in tetrahydrofuran (16 mL). This was followed by the addition of a solution of LiOH (112 mg, 4.68 mmol, 1.10 equiv) in water (14.4 mL) dropwise with stirring at 0° C. in 5 min. The resulting solution was stirred for 1 h at 25° C. The resulting mixture was concentrated under vacuum. The residue was diluted with 20 mL of water. The resulting solution was extracted with 2×20 mL of ethyl acetate and the aqueous layers combined. The pH value of the solution was adjusted to 2 with hydrogen chloride (1 mol/L). The resulting solution was extracted with 3×30 mL of ethyl acetate and the organic layers combined. The resulting mixture was washed with 1×40 mL of brine. The mixture was dried over anhydrous sodium sulfate and concentrated under vacuum. This resulted in 1.3 g (84%) of (S)-5-(4-fluorobenzamido)-6-morpholino-6-oxohexanoic acid as light yellow oil

Step 5. 4-fluoro-N—((S)-6-((1R,2S)-2-(4-fluorophenyl)cyclopropylamino)-1-morpholino-1,6-dioxohexan-2-yl)benzamide Into a 100-mL round-bottom flask, was placed a solution of (S)-5-(4-fluorobenzamido)-6-morpholino-6-oxohexanoic acid (200 mg, 0.60 mmol, 1.00 equiv) in N,N-dimethylformamide (30 mL), HATU (500 mg, 1.31 mmol, 2.00 equiv), DIEA (170 mg, 1.32 mmol, 2.00 equiv) and (1R,2S)-2-(4-fluorophenyl)cyclopropanamine (94.3 mg, 0.62 mmol, 1.10 equiv). The resulting solution was stirred for 2 h at 25° C. The resulting solution was diluted with 100 mL of $H_2O$. The resulting solution was extracted with 3×30 mL of ethyl acetate and the organic layers combined. The organic layers were washed with 1×100 mL of Brine. The mixture was dried over anhydrous sodium sulfate. The solids were filtered out. The resulting mixture was concentrated under vacuum. The crude product was purified by Prep-HPLC. This resulted in 196.1 mg (67%) of 4-fluoro-N—((S)-6-((1R,2S)-2-(4-fluorophenyl)cyclopropylamino)-1-morpholino-1,6-dioxohexan-2-yl)benzamide as a white solid. $^1$H NMR (300 MHz, $CD_3OD$-$d_4$) δ ppm: 7.95 (dd, $J_1$=6.7 Hz, $J_2$=3.15 Hz, 2H), 7.23-7.25 (m, 4H), 6.99 (t, J=9.3 Hz, 2H), 4.87-5.04 (m, 1H), 3.73-3.58 (m, 8H), 2.84-2.79 (m, 1H), 2.29-2.75 (m, 2H), 2.04-1.99 (m, 1H), 1.84-1.72 (m, 4H), 1.19-1.14 (m, 2H). LC/MS: (ES, m/z): 486 [M+H]$^+$

Example 23: N—((S)-6-((1R,2S)-2-(4-fluorophenyl)cyclopropylamino)-1-oxo-1-(piperidin-1-yl)hexan-2-yl)-1H-imidazole-5-carboxamide

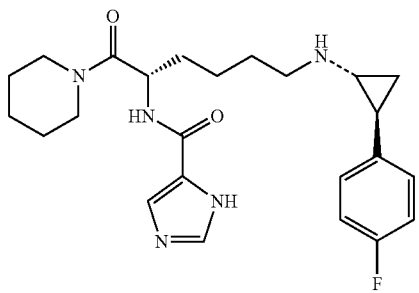

Example 24: 4-fluoro-N—((S)-6-((1R,2S)-2-(4-fluorophenyl)cyclopropylamino)-1-(4-methylpiperazin-1-yl)-1,6-dioxohexan-2-yl)benzamide

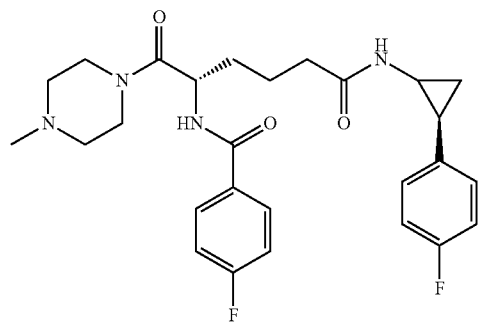

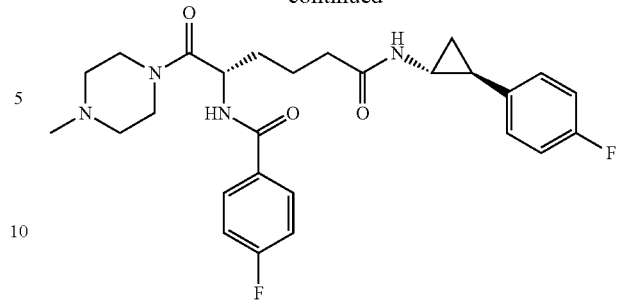

Step 1. (S)-methyl 5-(4-fluorobenzamido)-6-(4-methylpiperazin-1-yl)-6-oxohexanoate (1)

Into a 500-mL 3-necked round-bottom flask, was placed a solution of (S)-2-(4-fluorobenzamido)-6-methoxy-6-oxohexanoic acid (3.5 g, 11.77 mmol, 1.00 equiv) in tetrahydrofuran (90 mL), DEPBT (7 g, 23.41 mmol, 2.00 equiv) and imidazole (1.6 g, 23.53 mmol, 2.00 equiv). The mixture solution was stirred for 30 min at 0° C. This was followed by the addition of a solution of 1-methylpiperazine (1.2 g, 11.98 mmol, 1.00 equiv) in tetrahydrofuran (50 mL) dropwise with stirring at 0° C. in 40 min. The resulting solution was stirred for 16 h at 25° C. The resulting solution was diluted with 150 mL of $KH_2PO_4$ (aq.). The resulting solution was extracted with 3×150 mL of ethyl acetate and the organic layers combined. The resulting mixture was washed with 1×300 mL of brine. The mixture was dried over anhydrous sodium sulfate and concentrated under vacuum. The residue was applied onto a silica gel column with ethyl acetate/petroleum ether (1:1). This resulted in 2.4 g (54%) of (S)-methyl 5-(4-fluorobenzamido)-6-(4-methylpiperazin-1-yl)-6-oxohexanoate as light yellow oil.

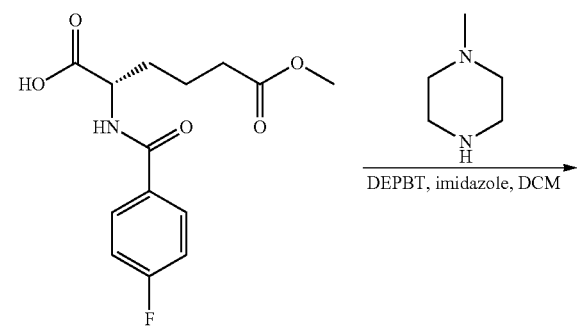

Step 2. (S)-5-(4-fluorobenzamido)-6-(4-methylpiperazin-1-yl)-6-oxohexanoic acid (2)

Into a 100-mL round-bottom flask, was placed a solution of (S)-methyl 5-(4-fluorobenzamido)-6-(4-methylpiperazin-1-yl)-6-oxohexanoate (1.75 g, 4.64 mmol, 1.00 equiv) in tetrahydrofuran (17 mL). This was followed by the addition of a solution of LiOH (118 mg, 4.93 mmol, 1.10 equiv) in $H_2O$ (15 mL) dropwise with stirring at 0° C. The resulting solution was stirred for 1 h at 25° C. The resulting mixture was concentrated under vacuum. This resulted in 1.3 g (crude) (77%) of (S)-5-(4-fluorobenzamido)-6-(4-methylpiperazin-1-yl)-6-oxohexanoic acid as yellow oil.

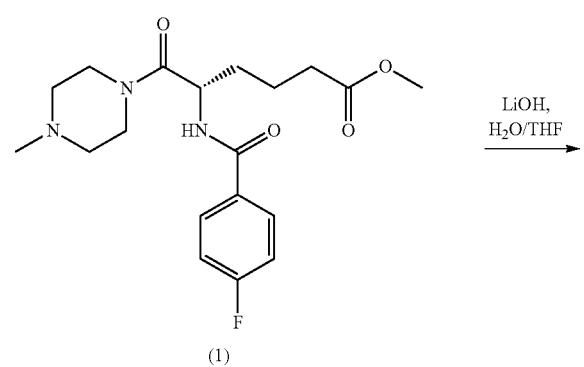

Step 3. 4-fluoro-N—((S)-6-((1R,2S)-2-(4-fluorophenyl)cyclopropylamino)-1-(4-methylpiperazin-1-yl)-1,6-dioxohexan-2-yl)benzamide Into a 100-mL round-bottom flask, was placed a solution of (S)-5-(4-fluorobenzamido)-6-(4-methylpiperazin-1-yl)-6-oxohexanoic acid (400 mg, 1.10 mmol, 1.00 equiv) in N,N-dimethylformamide (50 mL), HATU (832 mg, 2.19 mmol, 2.00 equiv), DIEA (284 mg, 2.20 mmol, 2.00 equiv) and (1R,2S)-2-(4-fluorophenyl)cyclopropanamine (182 mg, 1.20 mmol, 1.10 equiv). The resulting solution was stirred for 1 h at 25° C. The resulting mixture was concentrated under vacuum. The crude product was purified by Prep-HPLC. This resulted in 63.1 mg (11%) of 4-fluoro-N—((S)-6-((1R,2S)-2-(4-fluorophenyl)cyclopropylamino)-1-(4-

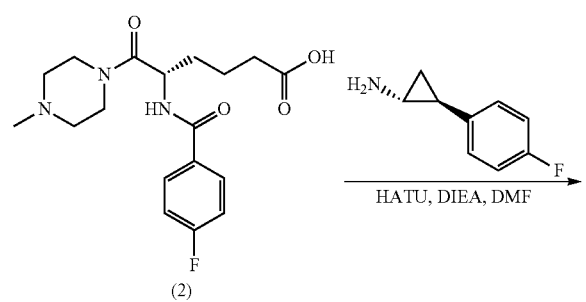

methylpiperazin-1-yl)-1,6-dioxohexan-2-yl)benzamide as a white solid. ¹H NMR (300 MHz, CD₃OD-d₄) δ ppm: 7.95 (dd, J₁=6.7 Hz, J₂=3.15 Hz, 2H), 7.23-7.25 (m, 4H), 6.99 (t, J=9.3 Hz, 2H), 4.87-5.04 (m, 1H), 3.73-3.58 (m, 8H), 2.84-2.79 (m, 1H), 2.29-2.75 (m, 2H), 2.04-1.99 (m, 1H), 1.84-1.72 (m, 4H), 1.19-1.14 (m, 2H). LC/MS: (ES, m/z): 486 [M+H]⁺

Example 25: 4-fluoro-N—((S)-3-(2-((1R,2S)-2-(4-methoxyphenyl)cyclopropylamino)-2-oxoethoxy)-1-morpholino-1-oxopropan-2-yl)benzamide

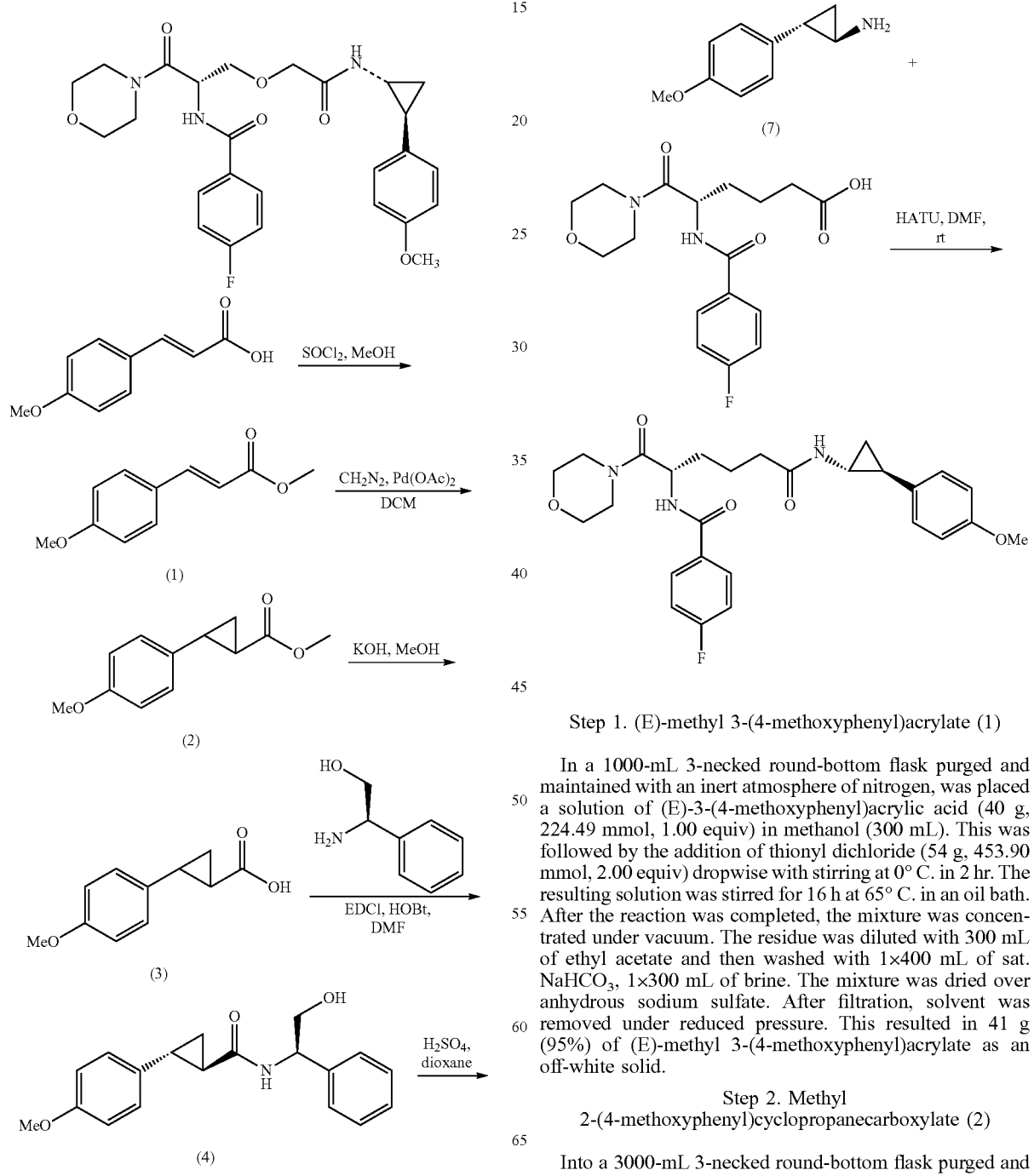

Step 1. (E)-methyl 3-(4-methoxyphenyl)acrylate (1)

In a 1000-mL 3-necked round-bottom flask purged and maintained with an inert atmosphere of nitrogen, was placed a solution of (E)-3-(4-methoxyphenyl)acrylic acid (40 g, 224.49 mmol, 1.00 equiv) in methanol (300 mL). This was followed by the addition of thionyl dichloride (54 g, 453.90 mmol, 2.00 equiv) dropwise with stirring at 0° C. in 2 hr. The resulting solution was stirred for 16 h at 65° C. in an oil bath. After the reaction was completed, the mixture was concentrated under vacuum. The residue was diluted with 300 mL of ethyl acetate and then washed with 1×400 mL of sat. NaHCO₃, 1×300 mL of brine. The mixture was dried over anhydrous sodium sulfate. After filtration, solvent was removed under reduced pressure. This resulted in 41 g (95%) of (E)-methyl 3-(4-methoxyphenyl)acrylate as an off-white solid.

Step 2. Methyl 2-(4-methoxyphenyl)cyclopropanecarboxylate (2)

Into a 3000-mL 3-necked round-bottom flask purged and maintained with an inert atmosphere of nitrogen, was placed a solution of (E)-methyl 3-(4-methoxyphenyl)acrylate (41 g, 213.31 mmol, 1.00 equiv) in dichloromethane (500 mL), Pd(OAc)$_2$ (480 mg, 2.14 mmol, 0.01 equiv). This was followed by the addition of a solution of CH$_2$N$_2$ in ether (1500 mL) dropwise with stirring at −5° C. The resulting solution was stirred for 4 h at 0° C. After the reaction was completed, the reaction was quenched by the addition of 4 mL of AcOH. The resulting mixture was washed with 1×400 mL of sat.Na$_2$CO$_3$ and then concentrated under vacuum. The residue was applied onto a silica gel column with ethyl acetate/petroleum ether (1:3). The collected fractions were combined and concentrated under vacuum. This resulted in 42 g (97%) of methyl 2-(4-methoxyphenyl)cyclopropanecarboxylate as an off-white solid.

Step 3.
2-(4-methoxyphenyl)cyclopropanecarboxylic Acid (3)

Into a 1000-mL round-bottom flask, was placed a solution of methyl 2-(4-methoxyphenyl)cyclopropanecarboxylate (42 g, 203.65 mmol, 1.00 equiv) in methanol (250 mL), then a solution of potassium hydroxide ((57 g, 1.02 mol, 5.00 equiv) in methanol (200 mL) was added. The resulting solution was stirred for 5 h at room temperature. After the reaction was completed, it was concentrated under vacuum. The residue was diluted with 1000 mL of H$_2$O. The pH value of the solution was adjusted to 2 with hydrogen chloride (2 mol/L). The resulting solution was extracted with 3×1000 mL of dichloromethane and the organic layers combined. The combined organic layers were washed with 1×1500 mL of brine and dried over anhydrous sodium sulfate. After filtration, solvent was removed under reduced pressure. This resulted in 36 g (90%) of 2-(4-methoxyphenyl)cyclopropanecarboxylic acid as an off-white solid.

Step 4. (1R,2R)—N—((R)-2-hydroxy-1-phenylethyl)-2-(4-methoxyphenyl)cyclopropanecarboxamide (4)

Into a 1000-mL round-bottom flask, was placed a solution of 2-(4-methoxyphenyl)cyclopropanecarboxylic acid (36 g, 187.29 mmol, 1.00 equiv) in N,N-dimethylformamide (500 mL), HOBt (25 g, 185.02 mmol, 1.00 equiv), EDCI (36 g, 187.79 mmol, 1.00 equiv), (2R)-2-amino-2-phenylethan-1-ol (26 g, 189.53 mmol, 1.00 equiv). The resulting solution was stirred for 2 h at room temperature. After the reaction was completed, the mixture was poured into 300 mL of ice/water with stirring. The solids were collected by filtration. The residue was applied onto a silica gel column with dichloromethane/ethyl acetate (10:1-1:1). This resulted in 10.0 g (17%) of (1R,2R)—N—((R)-2-hydroxy-1-phenylethyl)-2-(4-methoxyphenyl)cyclopropanecarboxamide as a white solid.

Step 5.
(1R,2R)-2-(4-methoxyphenyl)cyclopropanecarboxylic acid (5)

Into a 250-mL round-bottom flask, was placed a solution of (1R,2R)—N—((R)-2-hydroxy-1-phenylethyl)-2-(4-methoxyphenyl)cyclopropanecarboxamide (10 g, 32.12 mmol, 1.00 equiv) in 1,4-dioxane (70 mL) and sulfuric acid (70 mL, 3 mol/L). The resulting solution was stirred for 16 h at 100° C. in an oil bath. After the reaction was completed, it was cooled to room temperature. The resulting mixture was concentrated under vacuum. The residue was diluted with 300 mL of water, extracted with 3×300 mL of ethyl acetate and the organic layers combined. The combined organic layers were washed with 1×500 mL of brine and dried over anhydrous sodium sulfate. After filtration, solvent was removed under reduced pressure. This resulted in 4.8 g (78%) of (1R,2R)-2-(4-methoxyphenyl)cyclopropanecarboxylic acid as an off-white solid.

Step 6. Tert-butyl (1R,2S)-2-(4-methoxyphenyl)cyclopropylcarbamate (6)

Into a 250-mL round-bottom flask, was placed a solution of (1R,2R)-2-(4-methoxyphenyl)cyclopropanecarboxylic acid (4.8 g, 24.97 mmol, 1.00 equiv) in tert-Butanol (50 mL), DPPA (6.9 g, 25.07 mmol, 1.00 equiv), TEA (2.5 g, 24.71 mmol, 1.00 equiv). The resulting solution was stirred for 5 h at 90° C. in an oil bath. After the reaction was completed, it was concentrated under vacuum. The residue was applied onto a silica gel column with ethyl acetate/petroleum ether (1:10). The collected fractions were combined and concentrated under vacuum. This resulted in 2.5 g (38%) of tert-butyl (1R,2S)-2-(4-methoxyphenyl)cyclopropylcarbamate as a light yellow solid.

Step 7.
(1R,2S)-2-(4-methoxyphenyl)cyclopropanamine (7)

Into a 100-mL round-bottom flask, was placed a solution of tert-butyl (1R,2S)-2-(4-methoxyphenyl)cyclopropylcarbamate (2.5 g, 9.49 mmol, 1.00 equiv) in HCl/MeOH (40 mL). The resulting solution was stirred for 2 h at room temperature. After the reaction was completed, it was concentrated under vacuum. The resulting solution was diluted with 50 mL of H$_2$O, extracted with 2×30 mL of ethyl acetate and the aqueous layers combined. Sat.NaHCO$_3$ was employed to adjust the pH to 9. The resulting solution was extracted with 3×40 mL of ethyl acetate and the organic layers combined. The combined organic layers were washed with 1×100 mL of brine and dried over anhydrous sodium sulfate. After filtration, solvent was removed under reduced pressure. This resulted in 1.4 g (90%) of (1R,2S)-2-(4-methoxyphenyl)cyclopropanamine as light yellow oil. $^1$H-NMR (300 MHz, CDCl$_3$): δ ppm: 7.00-6.90 (m, 2H), 6.83-6.76 (m, 2H), 3.77 (s, 3H), 2.52-2.45 (m, 1H), 1.85-1.78 (m, 1H), 1.72 (s, 2H), 1.02-0.86 (m 2H).

Step 8. 4-fluoro-N—((S)-6-((1R,2S)-2-(4-methoxyphenyl)cyclopropylamino)-1-morpholino-1,6-dioxohexan-2-yl)benzamide Into a 100-mL round-bottom flask, was placed a solution of (S)-5-(4-fluorobenzamido)-6-morpholino-6-oxohexanoic acid (200 mg, 0.57 mmol, 1.00 equiv), HATU (500 mg, 1.31 mmol, 2.00 equiv) and DIEA (170 mg, 1.32 mmol, 2.00 equiv) in N, N-dimethylformamide (30 mL). The mixture was stirring for 5 min at room temperature. Then (1R,2S)-2-(4-methoxyphenyl)cyclopropanamine (102 mg, 0.62 mmol, 1.10 equiv) was added. The resulting solution was continued to stir for 2 h at room temperature. After the reaction was completed, it was diluted with 50 mL of H$_2$O. The resulting solution was extracted with 3×30 mL of ethyl acetate and the organic layers combined. The organic layers were washed with 1×100 mL of brine and dried over anhydrous sodium sulfate. After filtration, solvent was removed under reduced pressure. The residue was purified by Prep-HPLC (ACN/H$_2$O with 0.5% NH$_4$HCO$_3$). This resulted in 138.7 mg (49%) of 4-fluoro-N—((S)-6-((1R,2S)-2-(4-methoxyphenyl)cyclopropylamino)-1-morpholino-1,6-dioxohexan-2-yl)benzamide as a white solid. 41 NMR (400 MHz, CD$_3$OD-d$_4$) δ ppm: 8.00-7.90 (m, 2H), 7.25-7.17 (m, 2H), 7.15-7.05 (m, 2H), 6.88-6.80 (m, 2H), 5.05-5.00 (m, 1H), 3.87-3.55 (m, 11H), 2.85-2.76 (m, 1H), 2.35-2.20 (m, 2H), 2.00-1.92 (m, 1H), 1.90-1.64 (m, 4H), 1.18-1.05 (m, 2H); MS (ES, ink): 498 (M+H).

Example 26: 4-fluoro-N—(S)-6-((1R,2S)-2-(4-methoxyphenyl)cyclopropylamino)-1-(4-methylpiperazin-1-yl)-1,6-dioxohexan-2-yl)benzamide

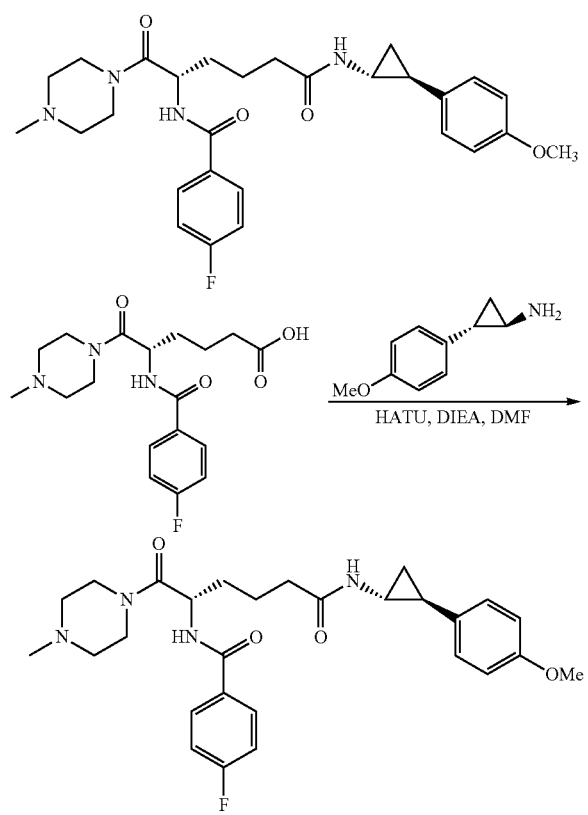

Into a 100-mL round-bottom flask, was placed a solution of (S)-5-(4-fluorobenzamido)-6-(4-methylpiperazin-1-yl)-6-oxohexanoic acid (300 mg, 0.83 mmol, 1.00 equiv) in N,N-dimethylformamide (30), HATU (624 mg, 1.64 mmol, 2.00 equiv), DIEA (213 mg, 1.65 mmol, 2.00 equiv) and (1R,2S)-2-(4-methoxyphenyl)cyclopropanamine (Example 25 Step 7) (147 mg, 0.90 mmol, 1.10 equiv). The resulting solution was stirred for 1 h at 25° C. The resulting mixture was concentrated under vacuum. The crude product was purified by Prep-HPLC. This resulted in 78.3 mg (19%) of 4-fluoro-N—((S)-6-((1R,2S)-2-(4-methoxyphenyl)cyclopropylamino)-1-(4-methylpiperazin-1-yl)-1,6-dioxohexan-2-yl)benzamide as a white solid. $^1$H NMR (300 MHz, CD$_3$OD-d$_4$) δ ppm: 7.90-8.00 (m, 2H), 7.22 (m, 2H), 7.08 (d, J=6.6 Hz, 2H), 6.85 (d, J=6.6 Hz, 2H), 5.02-5.08 (m, 1H), 3.78 (s, 3H), 3.53-3.75 (m, 3H), 2.77-2.86 (m, 1H), 2.42-2.56 (m, 4H), 2.33 (s, 3H), 2.23-2.30 (m, 2H), 1.95-2.05 (m, 1H), 1.66-1.87 (m, 4H), 1.07-1.19 (m, 2H). LC/MS (ES, m/z): 511 [M+H]$^+$.

Example 27: N-[(2S)-6-[[(1R,2S)-2-(4-fluorophenyl)-1-methylcyclopropyl]amino]-1-(4-methanesulfonylpiperazin-1-yl)-1-oxohexan-2-yl]-N-methylbenzamide

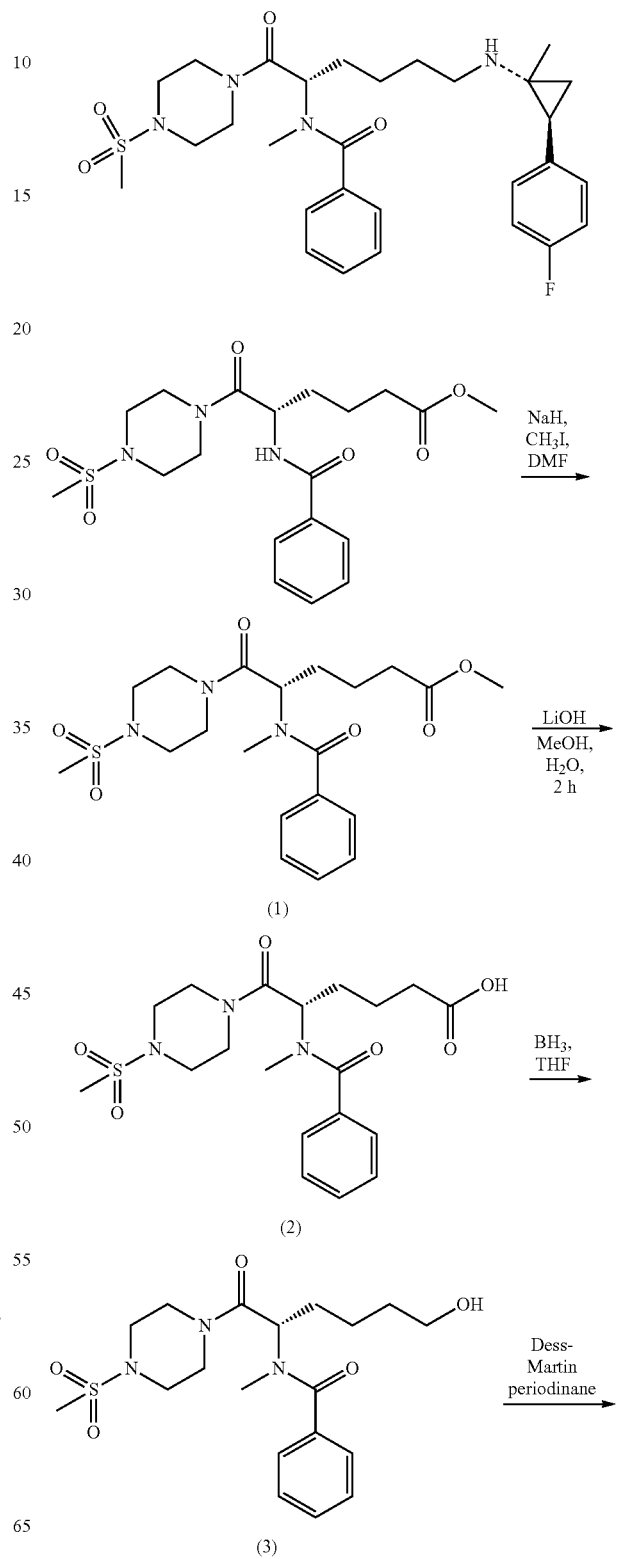

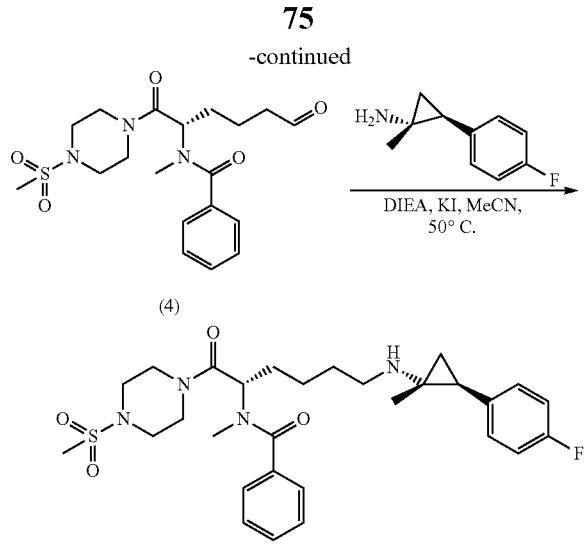

Step 1. Methyl (5S)-6-(4-methanesulfonylpiperazin-1-yl)-5-(N-methyl-1-phenylformamido)-6-oxohexanoate (1)

Into a 100-mL round-bottom flask, was placed a solution of methyl (5S)-6-(4-methanesulfonylpiperazin-1-yl)-6-oxo-5-(phenylformamido)hexanoate (100 mg, 0.24 mmol, 1.00 equiv) in N,N-dimethylformamide (20 mL), sodium hydride (10 mg, 0.42 mmol, 1.77 equiv), MeI (100 mg). The resulting solution was stirred for 1 overnight at 25° C. After the reaction was completed, the reaction was then quenched by the addition of water (100 mL). The resulting mixture was extracted with ethyl acetate (4×50 mL) and the organic layers were combined. The resulting mixture was washed with brine (3×50 mL), dried over anhydrous sodium sulfate and filtered. The filtrate was concentrated under vacuum. The obtained residue was purified by silica gel column chromatography using ethyl acetate/petroleum ether (1/3). This resulted in 50 mg (48%) of methyl (5S)-6-(4-methanesulfonylpiperazin-1-yl)-5-(N-methyl-1-phenylformamido)-6-oxohexanoate as a yellow solid.

Step 2. (5S)-6-(4-methanesulfonylpiperazin-1-yl)-5-(N-methyl-1-phenylformamido)-6-oxohexanoic acid (2)

Into a 100-mL round-bottom flask, was placed a solution of methyl (5S)-6-(4-methanesulfonylpiperazin-1-yl)-5-(N-methyl-1-phenylformamido)-6-oxohexanoate (100 mg, 0.23 mmol, 1.00 equiv) in tetrahydrofuran (30 mL), a solution of LiOH (100 mg) in water (20 mL). The resulting solution was stirred for 1 h at room temperature. After the reaction was completed. The reaction was then quenched by the addition of water (100 mL). The resulting mixture was extracted with ethyl acetate (4×50 mL) and the organic layers were combined. The resulting mixture was washed with brine (3×50 mL), dried over anhydrous sodium sulfate and filtered. The filtrate was concentrated under vacuum. The obtained residue was purified by silica gel column chromatography using ethyl acetate/petroleum ether (1/3). This resulted in 50 mg (52%) of (5S)-6-(4-methanesulfonylpiperazin-1-yl)-5-(N-methyl-1-phenylformamido)-6-oxohexanoic acid as a white solid.

Step 3. N-[(2S)-6-hydroxy-1-(4-methanesulfonylpiperazin-1-yl)-1-oxohexan-2-yl]-N-methylbenzamide (3)

Into a 100-mL round-bottom flask, was placed (5S)-6-(4-methanesulfonylpiperazin-1-yl)-5-(N-methyl-1-phenylformamido)-6-oxohexanoic acid (100 mg, 0.24 mmol, 1.00 equiv), BH₃/DCM (10 mL). The resulting solution was stirred for 1 h at room temperature. After the reaction was completed. The reaction was then quenched by the addition of water (100 mL). The resulting mixture was extracted with ethyl acetate (4×50 mL) and the organic layers were combined. The resulting mixture was washed with brine (3×50 mL), dried over anhydrous sodium sulfate and filtered. The filtrate was concentrated under vacuum. The obtained residue was purified by silica gel column chromatography using ethyl acetate/petroleum ether (1/3). This resulted in 50 mg (52%) of N-[(2S)-6-hydroxy-1-(4-methanesulfonylpiperazin-1-yl)-1-oxohexan-2-yl]-N-methylbenzamide as yellow oil.

Step 4. N-[(2S)-1-(4-methanesulfonylpiperazin-1-yl)-1,6-dioxohexan-2-yl]-N-methylbenzamide (4)

Into a 100-mL round-bottom flask, was placed N-[(2S)-6-hydroxy-1-(4-methanesulfonylpiperazin-1-yl)-1-oxohexan-2-yl]-N-methylbenzamide (200 mg, 0.49 mmol, 1.00 equiv), Dess-Martin (200 mg), dichloromethane (30 mL). The resulting solution was stirred for 1 h at room temperature after the reaction was completed. The reaction was then quenched by the addition of water (100 mL). The resulting mixture was extracted with ethyl acetate (4×50 mL) and the organic layers were combined. The resulting mixture was washed with brine (3×50 mL), dried over anhydrous sodium sulfate and filtered. The filtrate was concentrated under vacuum. The obtained residue was purified by silica gel column chromatography using ethyl acetate/petroleum ether (1/3). This resulted in 150 mg (75%) of N-[(2S)-1-(4-methanesulfonylpiperazin-1-yl)-1,6-dioxohexan-2-yl]-N-methylbenzamide as a white solid.

Step 5. N-[(2S)-6-[[(1R,2S)-2-(4-fluorophenyl)-1-methylcyclopropyl]amino]-1-(4-methanesulfonylpiperazin-1-yl)-1-oxohexan-2-yl]-N-methylbenzamide Into a 100-mL round-bottom flask, was placed a solution of N-[(2S)-1-(4-methanesulfonylpiperazin-1-yl)-1,6-dioxohexan-2-yl]-N-methylbenzamide (150 mg, 0.37 mmol, 1.00 equiv) in dichloromethane (30 mL), Na(OAc)₃BH (200 mg), (1R,2S)-2-(4-fluorophenyl)-1-methylcyclopropan-1-amine hydrochloride (150 mg, 0.74 mmol, 2.03 equiv). The resulting solution was stirred for 1 h at room temperature. After the reaction was complete, the reaction was then quenched by the addition of water (100 mL). The resulting mixture was extracted with ethyl acetate (4×50 mL) and the organic layers were combined. The resulting mixture was washed with brine (3×50 mL), dried over anhydrous sodium sulfate and filtered. The filtrate was concentrated under vacuum. The obtained residue was purified by silica gel column chromatography using ethyl acetate/petroleum ether (1/3). This resulted in 22.7 mg (11%) of N-[(2S)-6-[[(1R,2S)-2-(4-fluorophenyl)-1-methylcyclopropyl]amino]-1-(4-methanesulfonylpiperazin-1-yl)-1-oxohexan-2-yl]-N-methylbenzamide as a light yellow solid. 1H NMR (300 MHz, MeOD, ppm): 7.48-7.53 (m, 5H), 7.25-7.35 (m, 2H), 7.05-7.15 (m, 2H), 5.56-5.65 (m, 1H), 3.18-3.95 (m, 9H), 2.89-2.90 (m, 6H), 2.60-2.70 (m, 1H), 1.13-2.08 (m, 12H). LC/MS (ES, m/z): 559 [M+H]+.

Example 28: N-[(2S)-6-[[(1R,2S)-2-(4-fluorophenyl)cyclopropyl]amino]-1-(4-methanesulfonylpiperazin-1-yl)-1-oxohexan-2-yl]-N-methylbenzamide

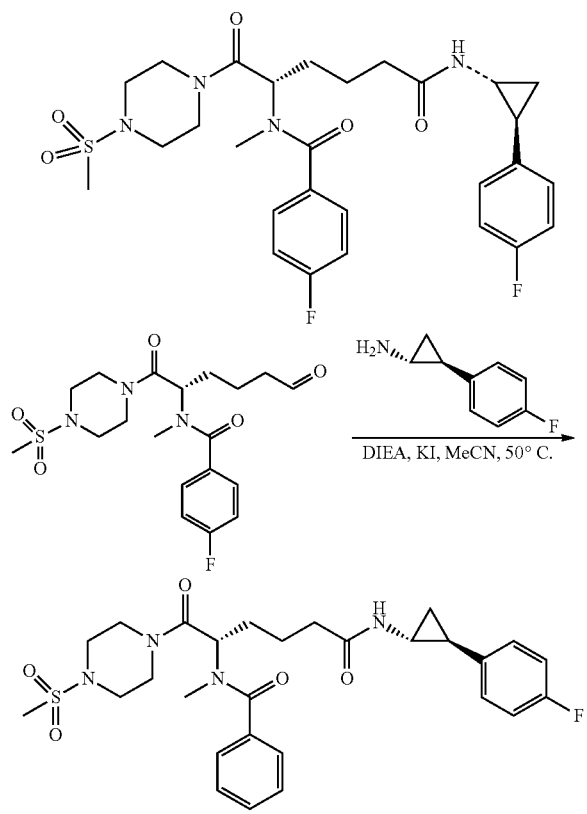

Into a 100-mL round-bottom flask, was placed a solution of N-[(2S)-1-(4-methanesulfonylpiperazin-1-yl)-1,6-dioxohexan-2-yl]-N-methylbenzamide (150 mg, 0.37 mmol, 1.00 equiv) in dichloromethane (60 mL), (1R,2S)-2-(4-fluorophenyl)cyclopropan-1-amine hydrochloride (100 mg, 0.53 mmol, 1.45 equiv), Na(OAc)$_3$BH (100 mg). The resulting solution was stirred for 1 h at room temperature. After the reaction was complete, the reaction was then quenched by the addition of water (100 mL). The resulting mixture was extracted with ethyl acetate (4×50 mL) and the organic layers were combined. The resulting mixture was washed with brine (3×50 mL), dried over anhydrous sodium sulfate and filtered. The filtrate was concentrated under vacuum. The obtained residue was purified by silica gel column chromatography using ethyl acetate/petroleum ether (1/3). This resulted in 67 mg (34%) of N-[(2S)-6-[[(1R,2S)-2-(4-fluorophenyl)cyclopropyl]amino]-1-(4-methanesulfonylpiperazin-1-yl)-1-oxohexan-2-yl]-N-methylbenzamide as an off-white solid. 1H NMR (400 MHz, CDCL3, ppm): 7.30-7.45 (m, 5H), 6.90-7.10 (m, 4H), 5.55-5.59 (m, 1H), 3.75-3.85 (m, 4H), 3.25-3.35 (m, 4H), 2.83-2.94 (m, 8H), 2.40-2.48 (m, 1H), 1.71-2.25 (m, 5H), 1.25-1.51 (m, 3H), 1.02-1.14 (m, 1H). LC/MS (ES, m/z): 545 [M+H]+.

Example 29: 4-fluoro-N-[(2S)-5-[[(1R,2S)-2-(4-fluorophenyl)cyclopropyl]amino]-1-(4-methanesulfonylpiperazin-1-yl)-1-oxopentan-2-yl]benzamide

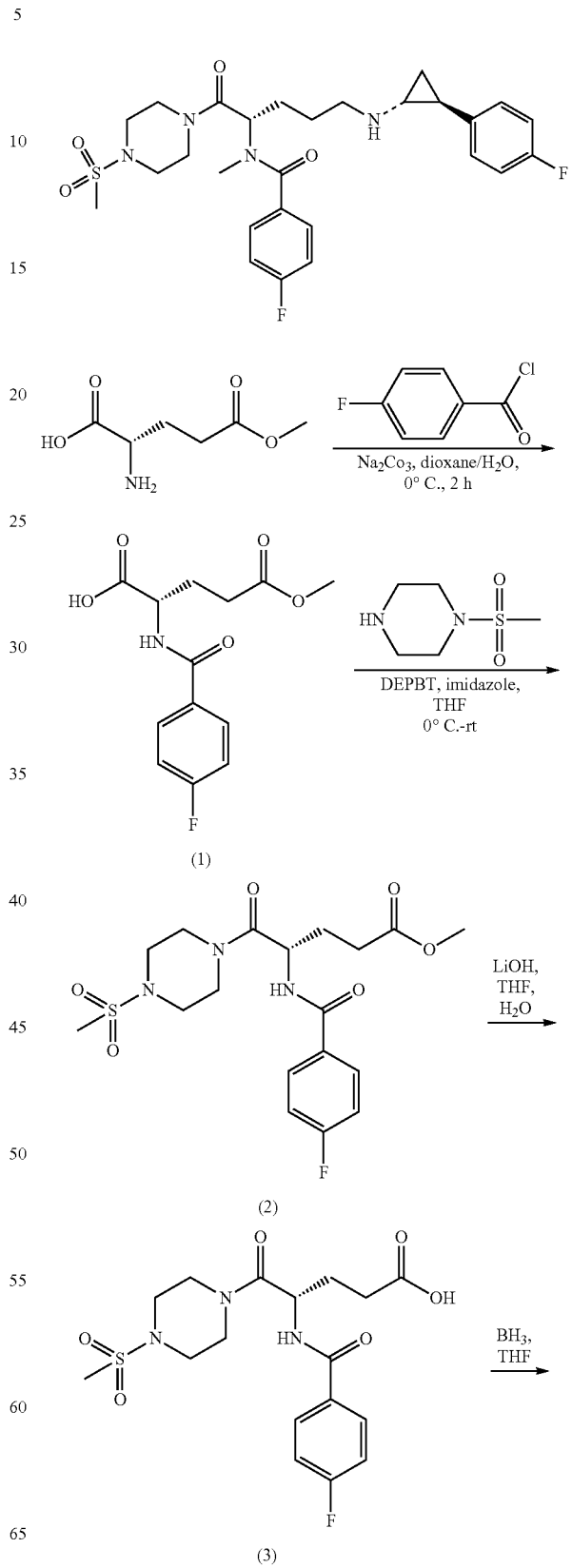

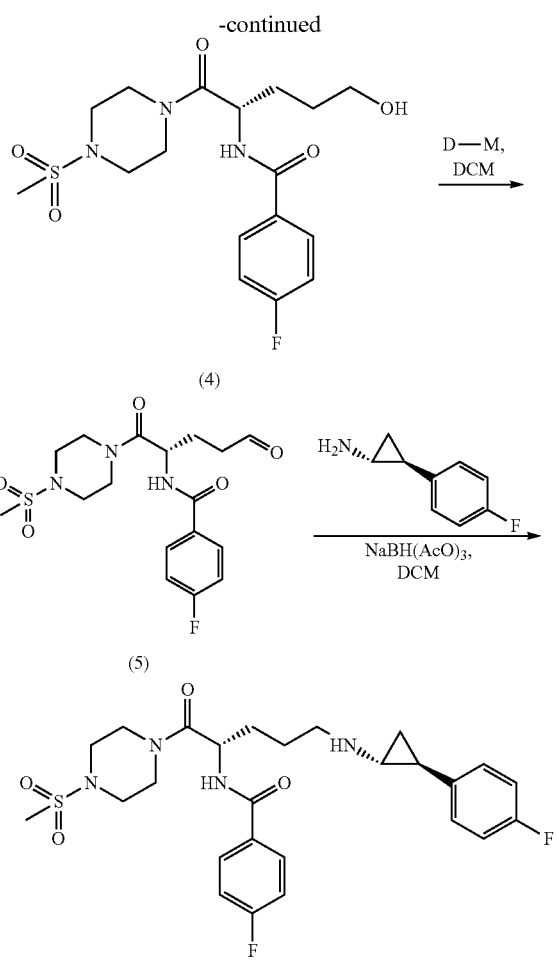

Step 1. (2S)-2-[(4-fluorophenyl)formamido]-5-methoxy-5-oxopentanoic Acid (1)

Into a 500-mL round-bottom flask, was placed a solution of (2S)-2-amino-5-methoxy-5-oxopentanoic acid (20 g, 124.10 mmol, 1.00 equiv) in dioxane (200 mL), a solution of sodium carbonate (20 g, 188.70 mmol, 1.52 equiv) in water (100 mL), 4-fluorobenzoyl chloride (20 g, 126.14 mmol, 1.02 equiv). The resulting solution was stirred for 2 h at 0° C. in a water bath. The resulting solution was extracted with 2×100 mL of ethyl acetate and the organic layers combined and dried over anhydrous magnesium sulfate and concentrated under vacuum. This resulted in 15 g (43%) of (2S)-2-[(4-fluorophenyl)formamido]-5-methoxy-5-oxopentanoic acid as an off-white solid.

Step 2. Methyl (4S)-4-[(4-fluorophenyl)formamido]-5-(4-methanesulfonylpiperazin-1-yl)-5-oxopentanoate (2)

Into a 250-mL round-bottom flask, was placed a solution of (2S)-2-[(4-fluorophenyl)formamido]-5-methoxy-5-oxopentanoic acid (8 g, 28.30 mmol, 1.00 equiv) in tetrahydrofuran (200 mL), DEPBT (15 g), imidazole (10 g), 1-methanesulfonylpiperazine (8 g, 48.71 mmol, 1.38 equiv). The resulting solution was stirred for 1 overnight at room temperature. After the reaction was completed, The mixture was diluted with 300 mL of H$_2$O. The aqueous phase was extracted with 3×200 mL of dichloromethane and the organic layers were combined. The organic layers were washed with 1×500 mL of brine and then dried with anhydrous sodium sulphate. After filtration, solvent was removed under reduced pressure. The residue was concentrated under vacuum and then applied onto a silica gel column with dichloromethane/methanol (10:1). This resulted in 6 g (50%) of methyl (4S)-4-[(4-fluorophenyl)formamido]-5-(4-methanesulfonylpiperazin-1-yl)-5-oxopentanoate as an off-white solid.

Step 3. (S)-4-(4-fluorobenzamido)-5-(4-(methylsulfonyl)piperazin-1-yl)-5-oxopentanoic acid (3)

Into a 100-mL round-bottom flask, was placed methyl (4S)-4-[(4-fluorophenyl)formamido]-5-(4-methanesulfonylpiperazin-1-yl)-5-oxopentanoate (1 g, 2.33 mmol, 1.00 equiv), methanol (30 mL), water (30 mL), and lithium hydroxide (1.5 g, 41.76 mmol, 24.88 equiv). The resulting solution was stirred for 3 h at room temperature. The pH value of the solution was adjusted to 6 with hydrogen chloride (12 mol/L). The resulting solution was extracted with 3×50 mL of ethyl acetate and the organic layers combined and concentrated under vacuum. This resulted in 700 mg (72%) of (S)-4-(4-fluorobenzamido)-5-(4-(methylsulfonyl)piperazin-1-yl)-5-oxopentanoic acid as a white solid.

Step 4. 4-fluoro-N-[(2S)-5-hydroxy-1-(4-methanesulfonylpiperazin-1-yl)-1-oxopentan-2-yl]benzamide (4)

Into a 100-mL round-bottom flask, was placed a solution of (S)-4-(4-fluorobenzamido)-5-(4-(methylsulfonyl)piperazin-1-yl)-5-oxopentanoic acid (700 mg, 1.68 mmol, 1.00 equiv) in tetrahydrofuran (60 mL), BH$_3$ (1 mL). The resulting solution was stirred for 3 h at room temperature. After the reaction was completed, The mixture was diluted with 300 mL of H$_2$O. The aqueous phase was extracted with 3×200 mL of dichloromethane and the organic layers were combined. The organic layers were washed with 1×500 mL of brine and then dried with anhydrous sodium sulphate. After filtration, solvent was removed under reduced pressure. The residue was concentrated under vacuum and then applied onto a silica gel column with dichloromethane/methanol (10:1). This resulted in 500 mg (73%) of 4-fluoro-N-[(2S)-5-hydroxy-1-(4-methanesulfonylpiperazin-1-yl)-1-oxopentan-2-yl]benzamide as a white solid.

Step 5. 4-fluoro-N-[(2S)-1-(4-methanesulfonylpiperazin-1-yl)-1,5-dioxopentan-2-yl]benzamide (5)

Into a 100-mL round-bottom flask, was placed 4-fluoro-N-[(2S)-5-hydroxy-1-(4-methanesulfonylpiperazin-1-yl)-1-oxopentan-2-yl]benzamide (200 mg, 0.50 mmol, 1.00 equiv), dichloromethane (20 mL), D-M (800 mg). The resulting solution was stirred for 2 h at room temperature. After the reaction was completed, The mixture was diluted with 300 mL of H$_2$O. The aqueous phase was extracted with 3×200 mL of dichloromethane and the organic layers were combined. The organic layers were washed with 1×500 mL of brine and then dried with anhydrous sodium sulphate. After filtration, solvent was removed under reduced pressure. The residue was concentrated under vacuum and then applied onto a silica gel column with dichloromethane/methanol (10:1). This resulted in 100 mg (50%) of 4-fluoro- N-[(2S)-1-(4-methanesulfonylpiperazin-1-yl)-1,5-dioxo-pentan-2-yl]benzamide as yellow oil.

Step 6. 4-fluoro-N-[(2S)-5-[[(1R,2S)-2-(4-fluoro-phenyl)cyclopropyl]amino]-1-(4-methanesulfo-nylpiperazin-1-yl)-1-oxopentan-2-yl]benzamide Into a 100-mL round-bottom flask, was placed a solution of 4-fluoro-N-[(2S)-1-(4-methanesulfonylpiperazin-1-yl)-1,5-dioxopentan-2-yl]benzamide (20 mg, 0.05 mmol, 1.00 equiv) in dichloromethane (mL), (1R,2S)-2-(4-fluorophenyl)cyclopropan-1-amine (40 mg, 0.26 mmol, 5.28 equiv), NaBH(AcO)$_3$ (50 mg). The resulting solution was stirred for 30 min at room temperature. After the reaction was completed, The mixture was diluted with 300 mL of H$_2$O. The aqueous phase was extracted with 3×200 mL of dichloromethane and the organic layers were combined. The organic layers were washed with 1×500 mL of brine and then dried with anhydrous sodium sulphate. After filtration, solvent was removed under reduced pressure. The residue was concentrated under vacuum and then applied onto a silica gel column with dichloromethane/methanol (10:1). This resulted in 3.4 mg (13%) of 4-fluoro-N-[(2S)-5-[[(1R,2S)-2-(4-fluorophenyl)cyclopropyl]amino]-1-(4-methane-sulfonylpiperazin-1-yl)-1-oxopentan-2-yl]benzamide as yellow oil. $^1$H NMR (MeOD, 400 MHz, ppm): 7.91-7.92 (m, 2H), 7.19-7.42 (m, 4H), 7.02-7.10 (m, 2H), 5.10-5.22 (m, 1H), 3.88-3.98 (m, 2H), 3.50-3.65 (m, 2H), 3.18-3.33 (m, 4H), 2.95-2.96 (m, 1H), 1.86-2.01 (m, 4H), 1.22-1.59 (m, 5H), 0.88-0.97 (m, 1H). LC/MS (ES, m/z): 535 [M+H]+.

Example 30: 1-((S)-6-((1R,2S)-2-(4-fluorophenyl)cyclopropylamino)-1-oxo-1-(piperidin-1-yl)hexan-2-yl)-3-phenylurea

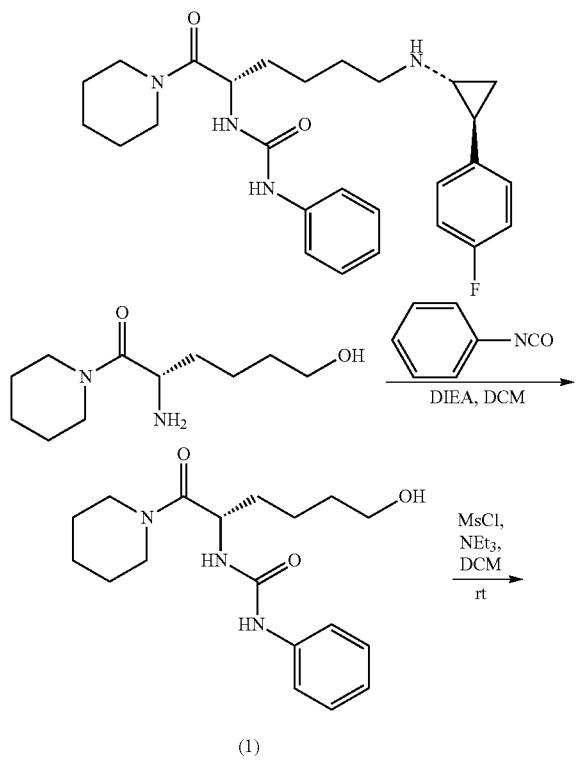

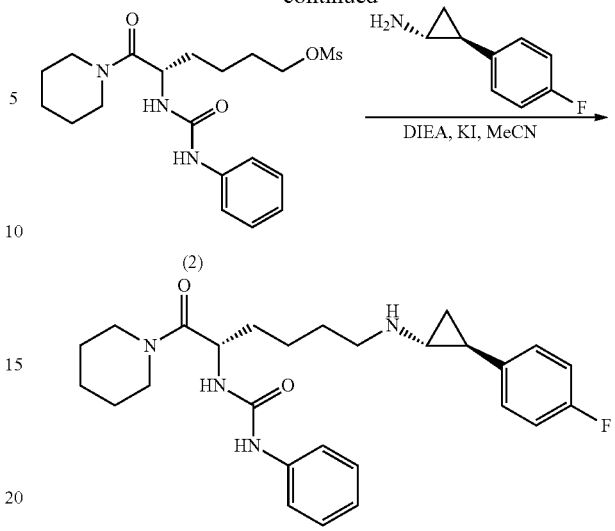

Step 1. (S)-1-(6-hydroxy-1-oxo-1-(piperidin-1-yl)hexan-2-yl)-3-phenylurea (1)

Into a 50-mL round-bottom flask, was placed (S)-2-amino-6-hydroxy-1-(piperidin-1-yl)hexan-1-one (200 mg, 0.93 mmol, 1.00 equiv), dichloromethane (25 mL), phenyl isocyanate (111 mg, 0.93 mmol, 1.00 equiv) at 0° C. in a water/ice bath. To this was added DIEA (362 mg, 2.80 mmol, 3.00 equiv) at the same temperature. The resulting solution was stirred for 1 h at room temperature. After the reaction was completed, it was diluted with 100 mL of DCM and then washed with 1×75 mL of H$_2$O, 1×75 mL of brine. The combined organic layers were dried over anhydrous sodium sulfate. After filtration, solvent was removed under reduced pressure. The residue was applied onto a silica gel column with ethyl acetate/petroleum ether (1:10). This resulted in 220 mg (71%) of (S)-1-(6-hydroxy-1-oxo-1-(piperidin-1-yl)hexan-2-yl)-3-phenylurea as light yellow oil.

Step 2. (S)-6-oxo-5-(3-phenylureido)-6-(piperidin-1-yl)hexyl methanesulfonate (2)

Into a 50-mL round-bottom flask, was placed (S)-1-(6-hydroxy-1-oxo-1-(piperidin-1-yl)hexan-2-yl)-3-phenylurea (220 mg, 0.66 mmol, 1.00 equiv), tetrahydrofuran (25 mL), NEt$_3$ (132 mg, 2.00 equiv). The reaction was cooled to 0° C. in a water/ice bath. MsCl (117 mg, 1.50 equiv) was added dropwise at that temperature. The resulting solution was stirred for 3 h at room temperature. After the reaction was completed, it was diluted with 100 mL of H$_2$O. The resulting solution was extracted with 3×100 mL of ethyl acetate and the organic layers combined. The combined organic layers were washed with 1×200 mL of brine and dried over anhydrous sodium sulfate. After filtration, solvent was removed under reduced pressure. The residue was applied onto a silica gel column with ethyl acetate/hexane (1:3). This resulted in 230 mg (85%) of (S)-6-oxo-5-(3-phenylureido)-6-(piperidin-1-yl)hexyl methanesulfonate as light yellow oil.

Step 3. 1-((S)-6-((1R,2S)-2-(4-fluorophenyl)cyclo-propylamino)-1-oxo-1-(piperidin-1-yl)hexan-2-yl)-3-phenylurea Into a 50-mL round-bottom flask, was placed (1R,2S)-2-(4-fluorophenyl)cyclopropanamine (85 mg, 0.56 mmol, 1.00 equiv), MeCN (25 mL), (S)-6-oxo-5-(3-phenylureido)-6-(piperidin-1-yl)hexyl methanesulfonate (230 mg, 0.56 mmol, 1.00 equiv), DIEA (145 mg, 1.12 mmol, 2.00 equiv), KI (9 mg, 0.05 mmol, 0.10 equiv). The resulting solution was stirred for 36 h at 60° C. in an oil bath. After the reaction was completed, the solution was diluted with 150 mL of DCM, and then washed with 1×100 mL of H₂O, 1×100 mL of brine. The combined organic layers were dried over anhydrous sodium sulfate. After filtration, solvent was removed under reduced pressure. The residue was purified by Prep-HPLC (ACN/H₂O with 0.5% NH₄HCO₃). This resulted in 5.8 mg (2%) of 1-((S)-6-(((1R,2S)-2-(4-fluorophenyl)cyclopropylamino)-1-oxo-1-(piperidin-1-yl)hexan-2-yl)-3-phenylurea as a white solid. ¹H NMR (300 MHz, CD₃OD-d₄) δ ppm: 7.40-7.15 (m, 4H), 7.15-6.90 (m, 5H), 4.76-4.52 (m, 1H), 3.70-3.42 (m, 4H), 2.72 (t, J=7.2 Hz, 2H), 2.32-2.25 (m, 1H), 1.95-1.85 (m, 1H), 1.82-1.35 (m, 12H), 1.10-0.85 (m, 2H); MS (ES, m/z): 467 (M+H).

Example 31: 1-((S)-6-(((1R,2S)-2-(4-fluorophenyl)cyclopropylamino)-1-oxo-1-(piperidin-1-yl)hexan-2-yl)-3-methylurea

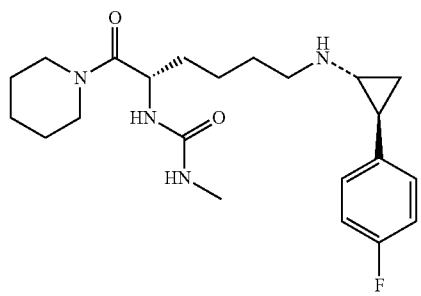

The title compound may be made in a manner analogous to the method set forth in Example 30 and by methods known in the art.

Example 32: 3,4-dichloro-N—((S)-5-((1S,2R)-2-(4-fluorophenyl)cyclopropylamino)-1-(4-(methylsulfonyl)piperazin-1-yl)-1-oxopentan-2-yl)benzamide

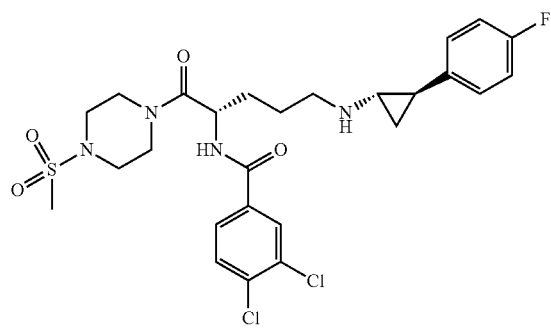 [SMILES: CS(=O)(=O)N1CCN(C(=O)[C@H](CCCN[C@H]2C[C@@H]2c2ccc(F)cc2)NC(=O)c2ccc(Cl)c(Cl)c2)CC1]

The title compound may be made by the method below and by methods known in the art.

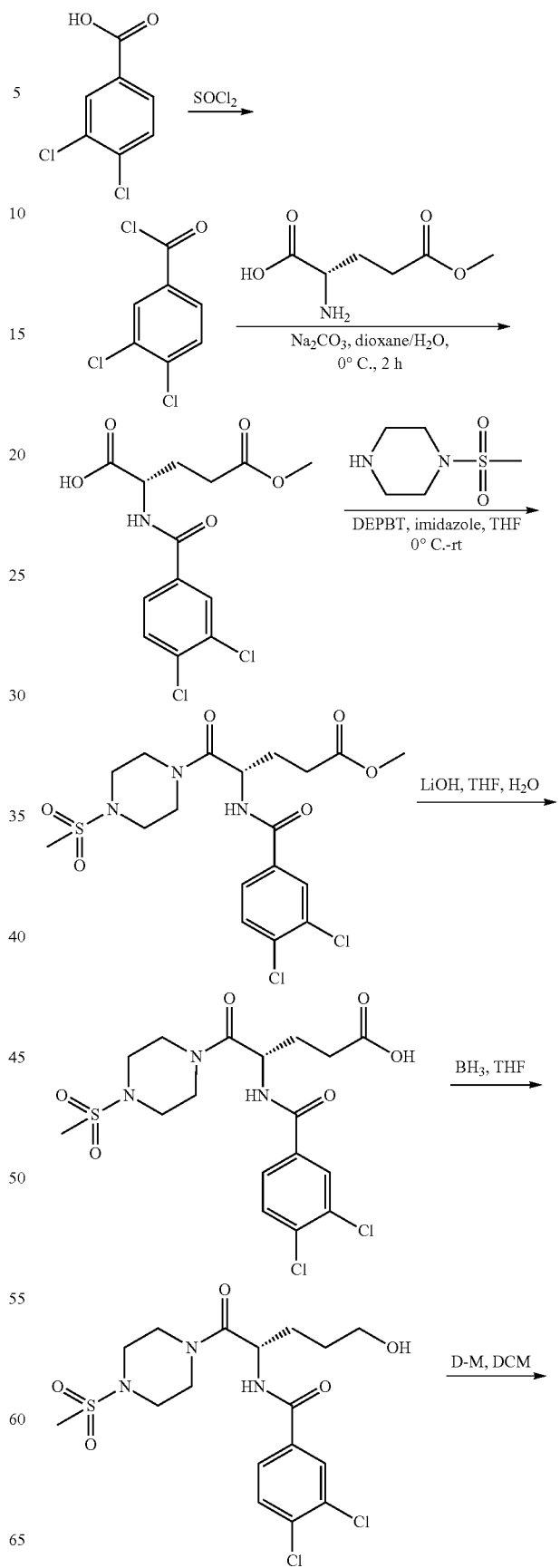

85
-continued
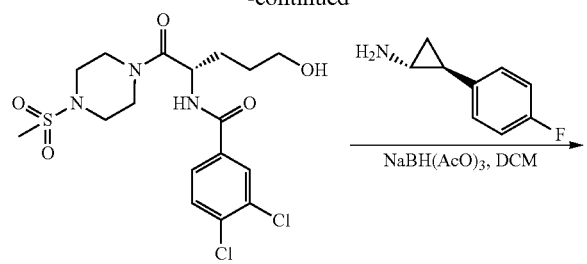
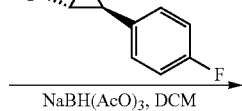
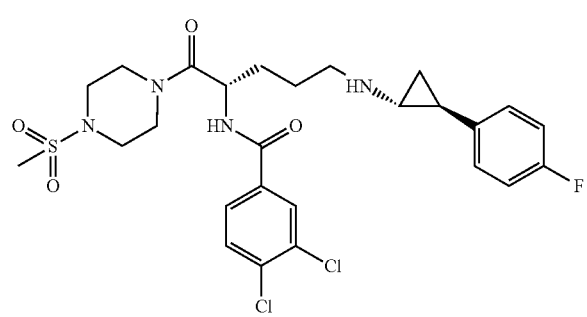
Example 33: 4-fluoro-N—((S)-5-((1R,2S)-2-(4-fluorophenyl)cyclopropylamino)-1-(4-(methylsulfonyl)piperazin-1-yl)-1-oxopentan-2-yl)-N-methylbenzamide
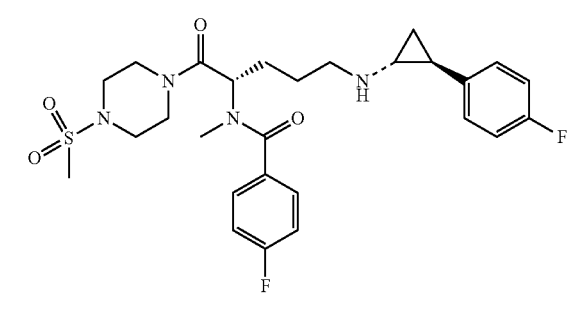
The title compound may be made by the method below and by methods known in the art.
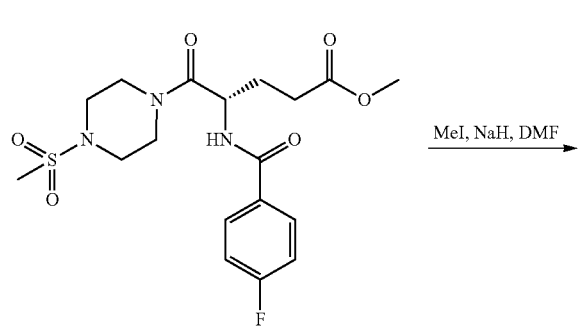
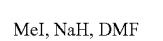
86
-continued
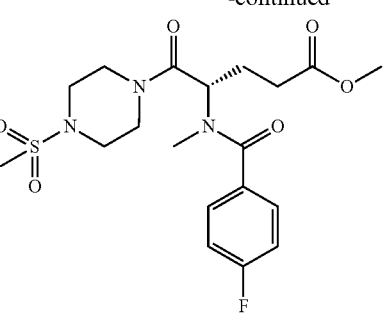
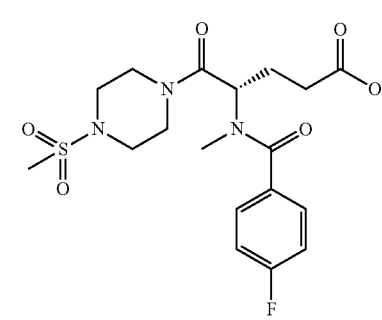
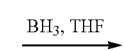
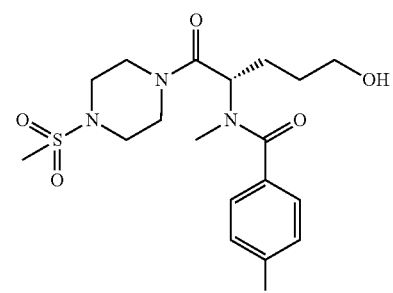
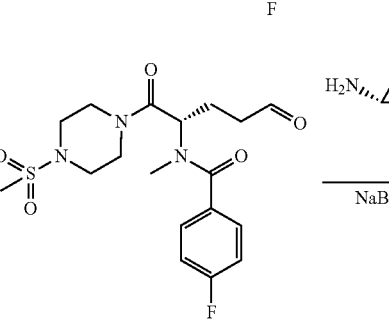
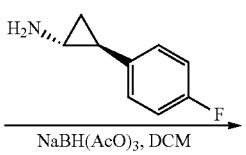
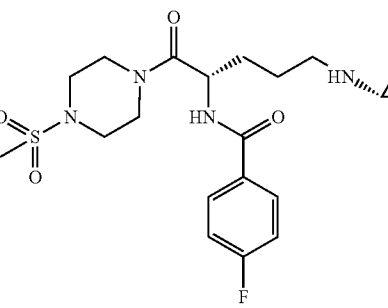

Example 34: 4-fluoro-N—((S)-5-((1S,2R)-2-(4-fluorophenyl)cyclopropylamino)-1-(4-methylpiperazin-1-yl)-1-oxopentan-2-yl)benzamide

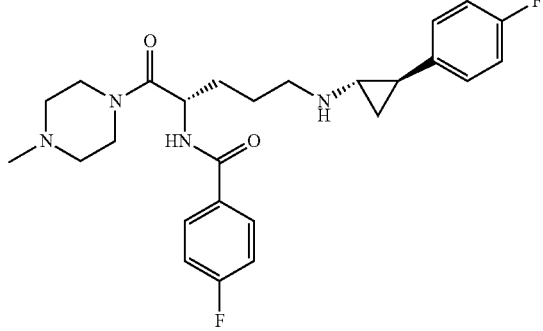

The title compound may be made by the method below and by methods known in the art.

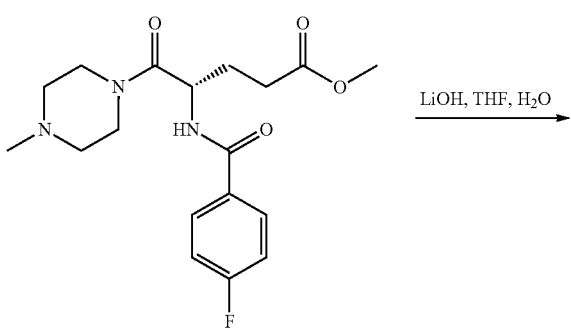

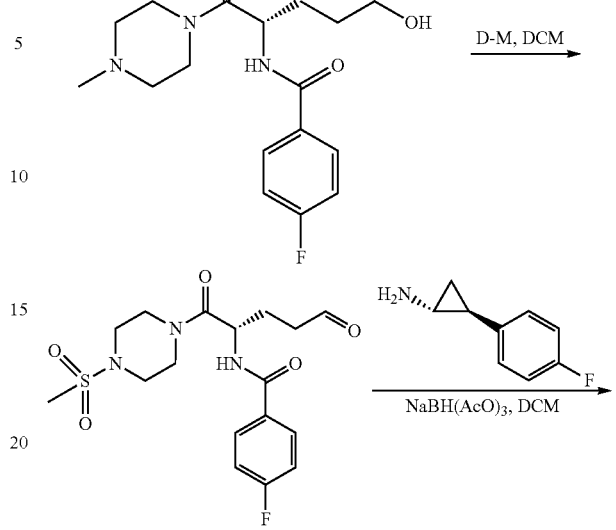

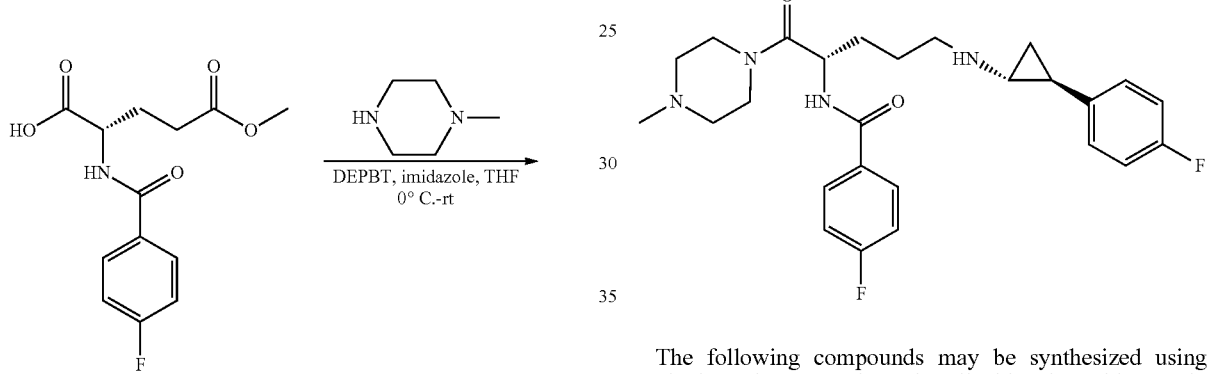

The following compounds may be synthesized using methods analogous to those described herein and known in the art, using appropriate starting materials and reagents. In the following structures, it should be understood that mixtures of or single isomers, such as racemic mixtures and alternate enantiomers, zwitterions, and the like may be prepared, e.g. by using appropriate L- or D-isomer, or chiral or achiral compound, as a staring material or reagent, or by employing a separation step.

Therefore, in certain embodiments in the compounds below, the configuration of the substituents off the cyclopropylamine is trans to the phenyl. In certain embodiments, the trans configuration is R, S; in others, it is S, R. Furthermore, in certain embodiments, the core contains a L-isomer, for example as shown in Formula II. Additional Examples include:

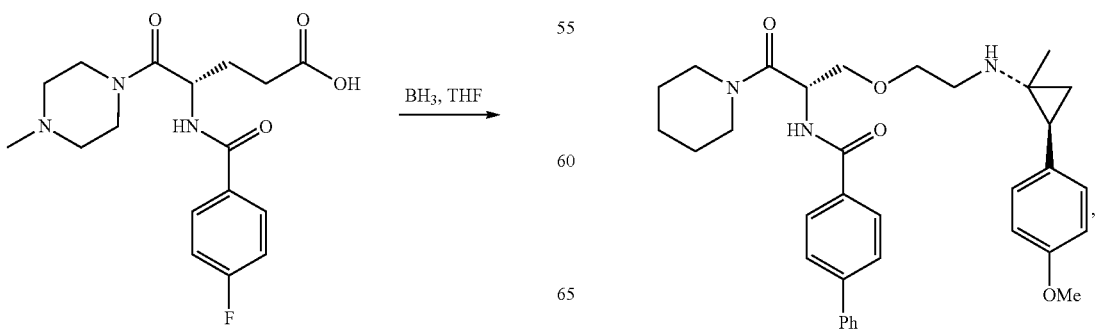

89
-continued
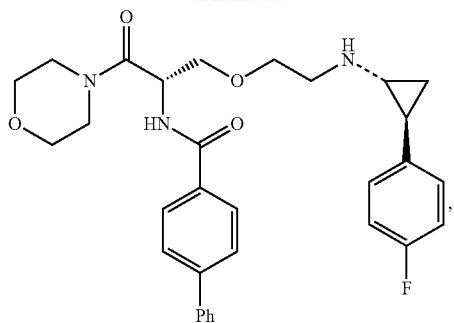
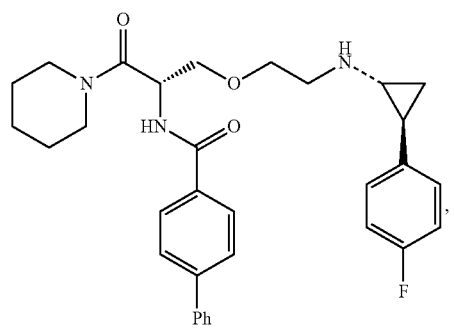
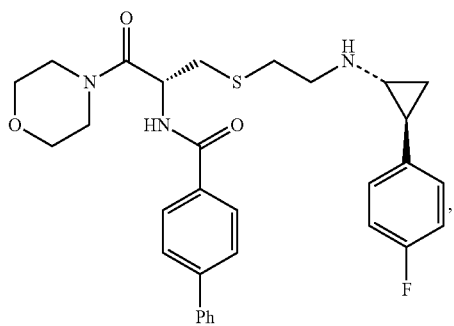
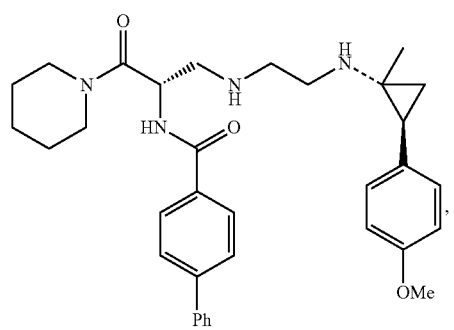
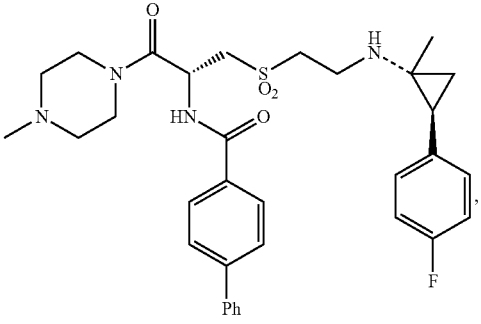
90
-continued
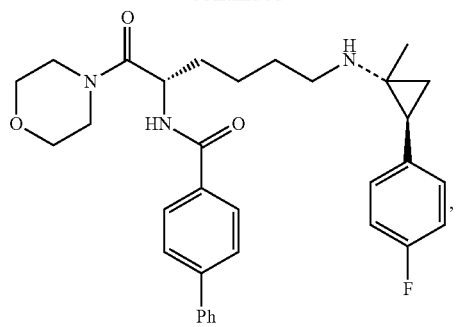
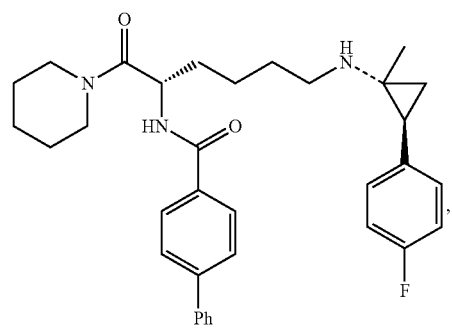
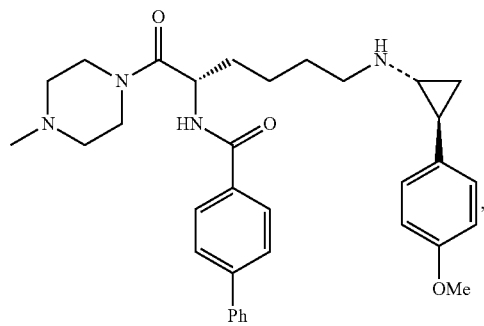
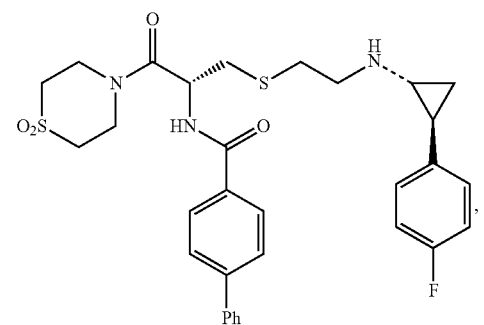
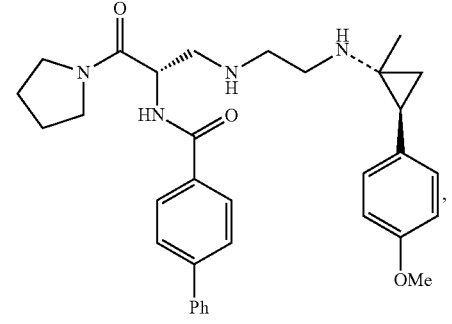

91
-continued
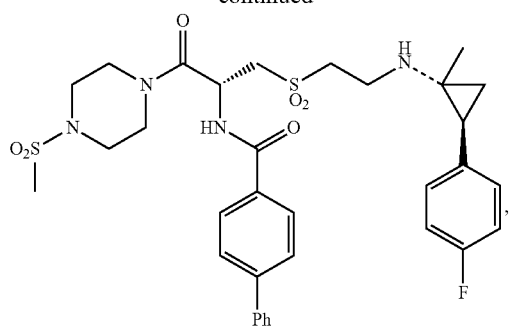
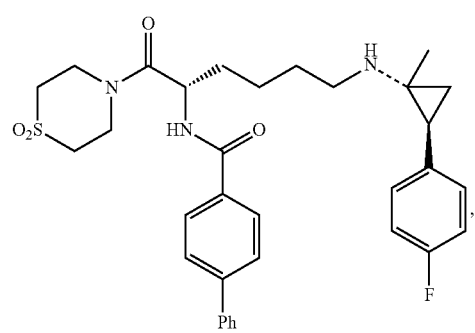
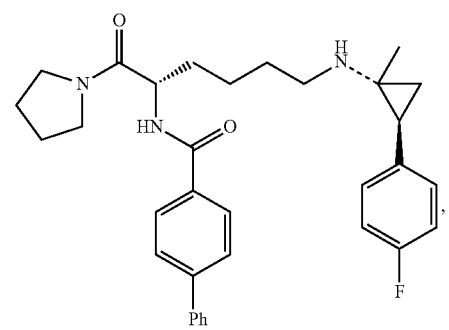
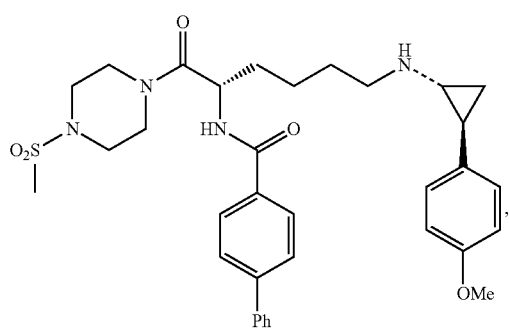
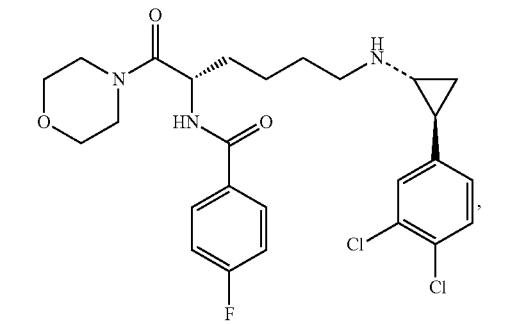
92
-continued
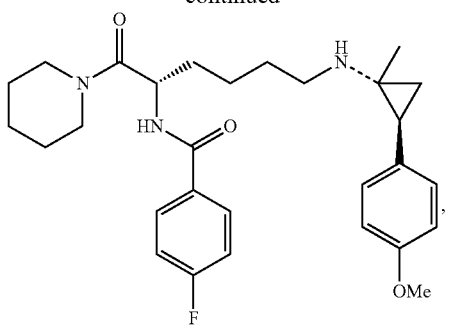
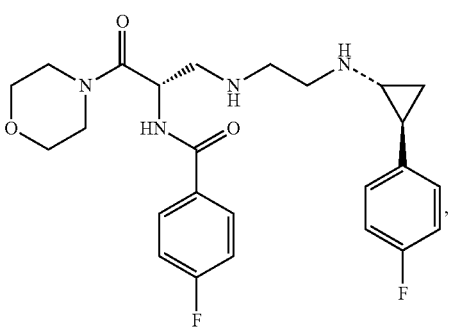
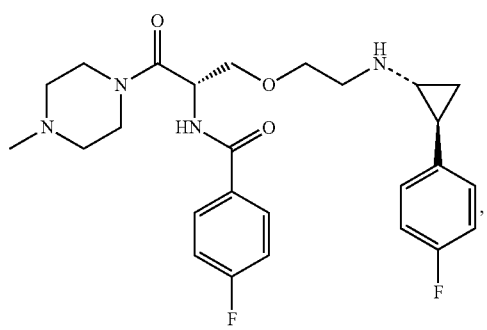
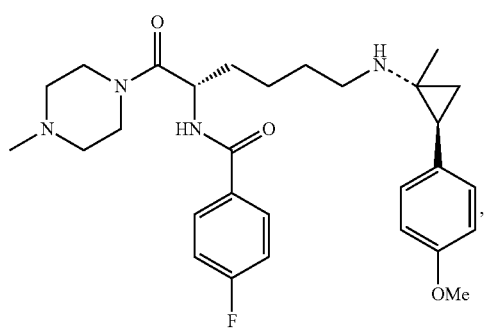
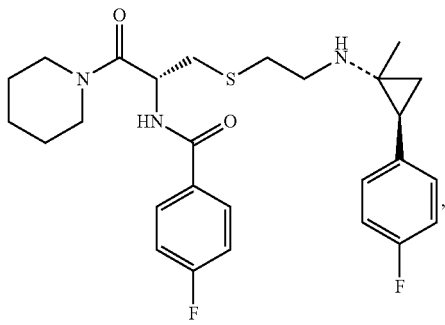

93
-continued
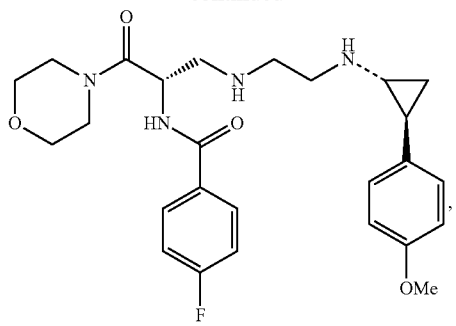
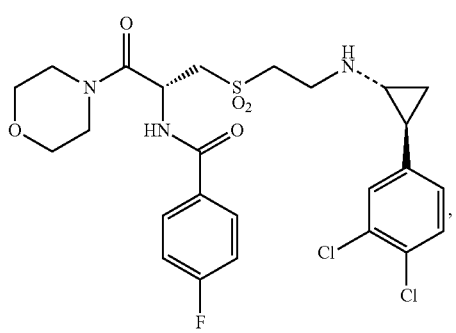
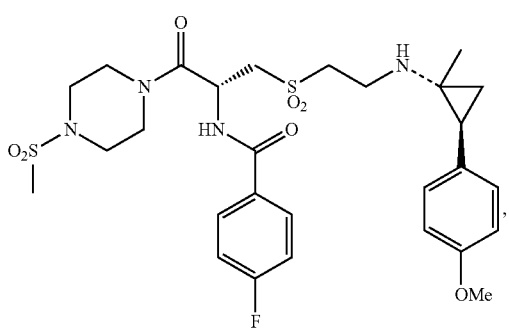
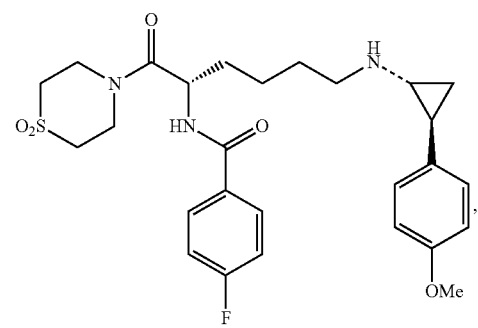
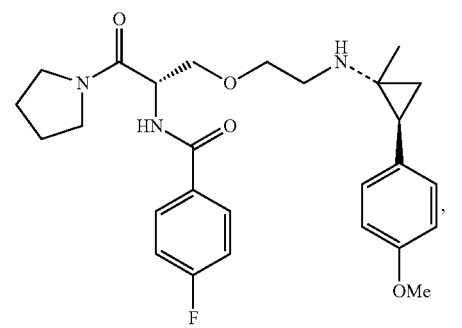
94
-continued
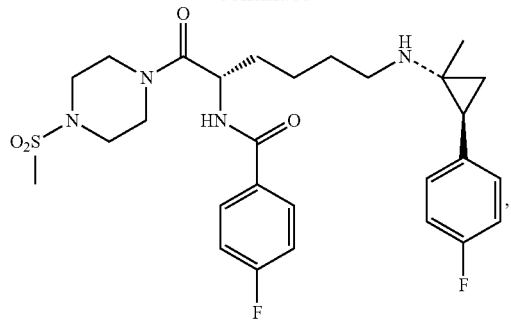
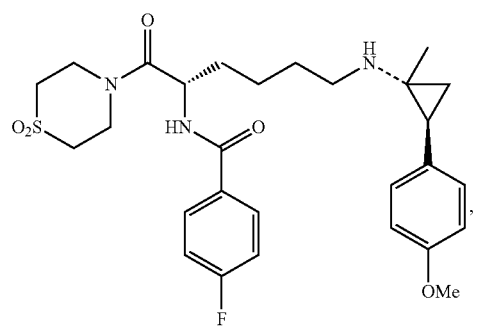
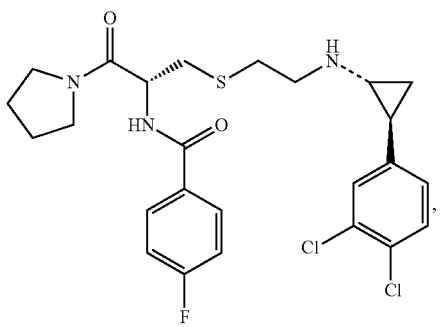
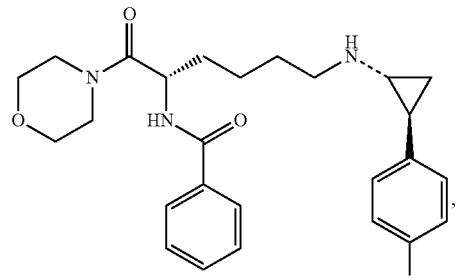
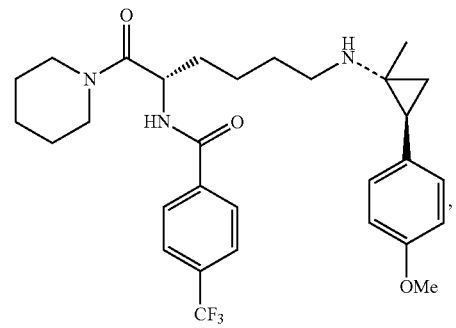

95
-continued
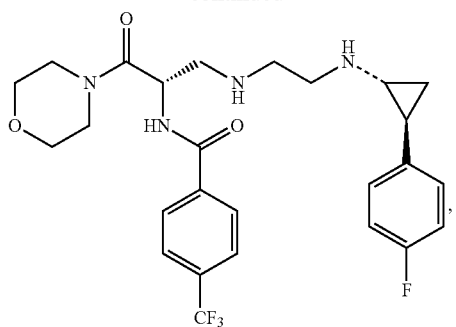
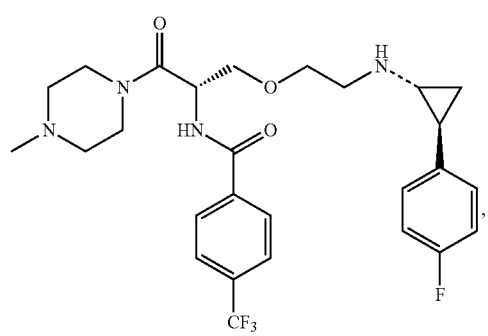
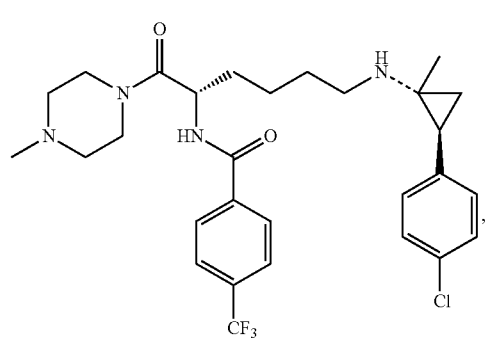
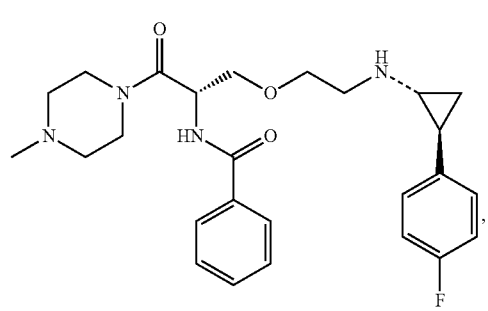
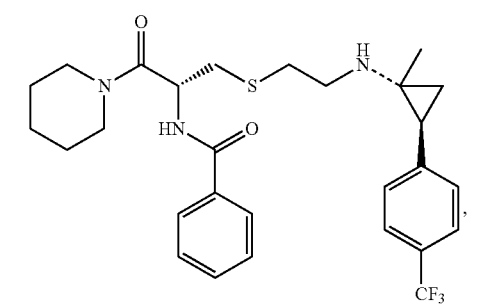
96
-continued
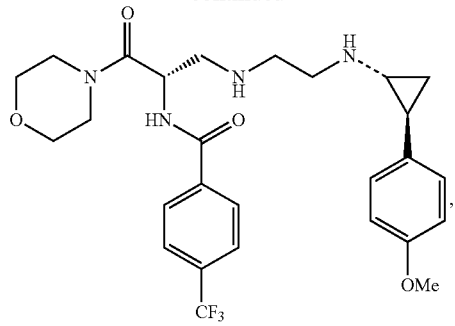
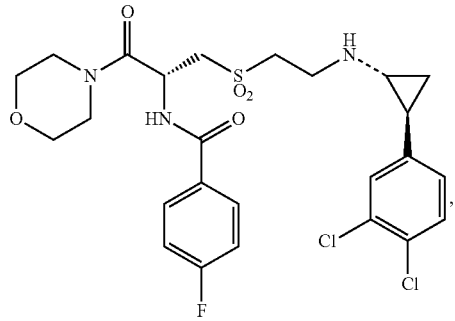
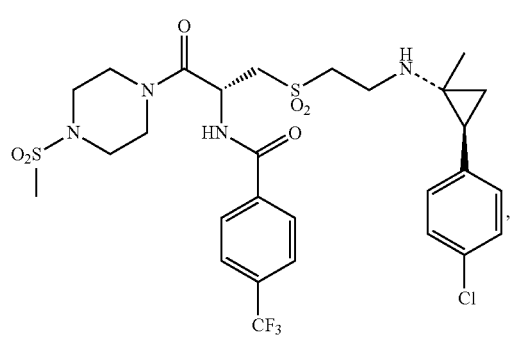
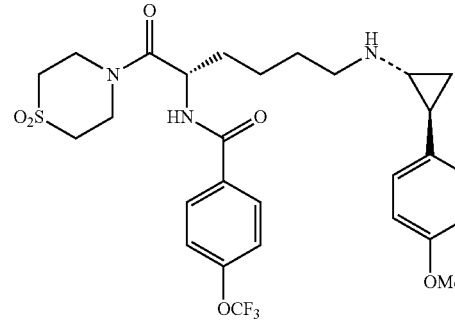
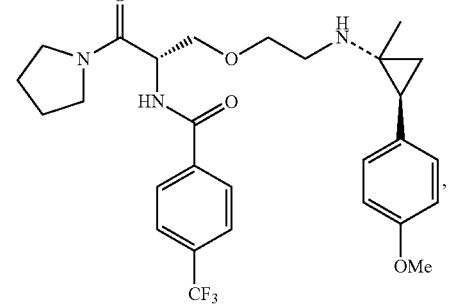

97
-continued
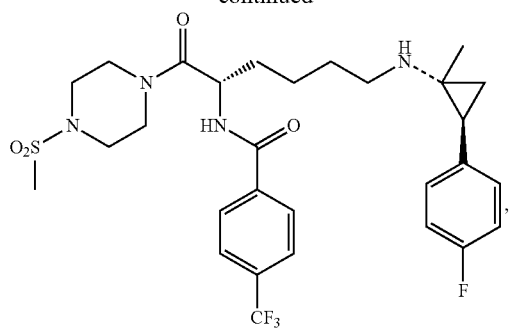
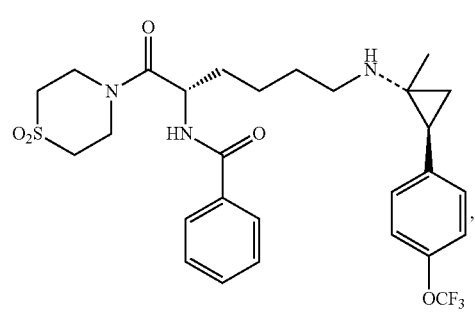
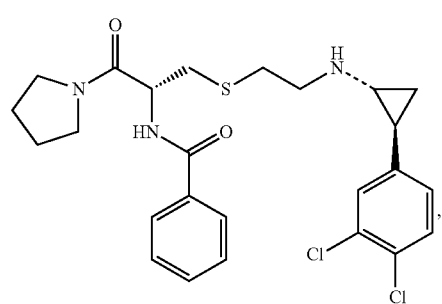
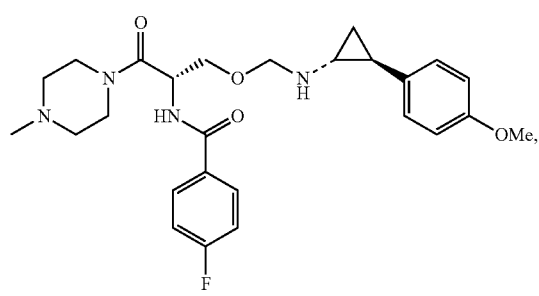
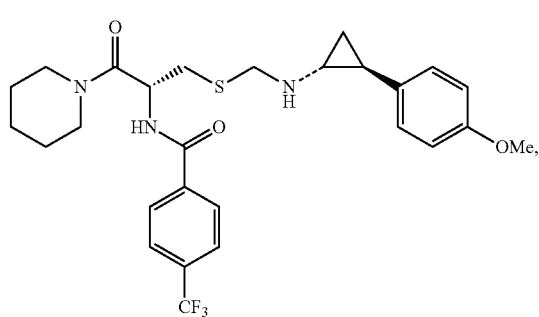
98
-continued
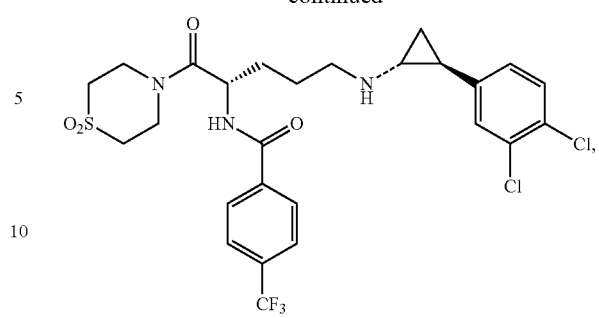
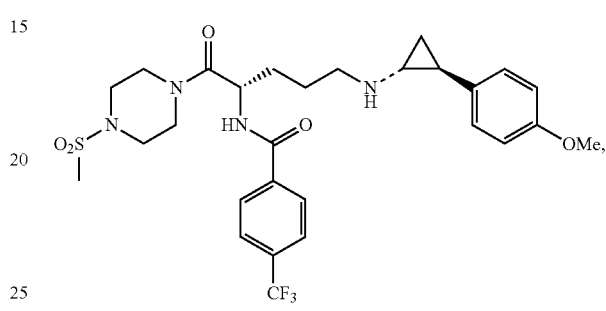
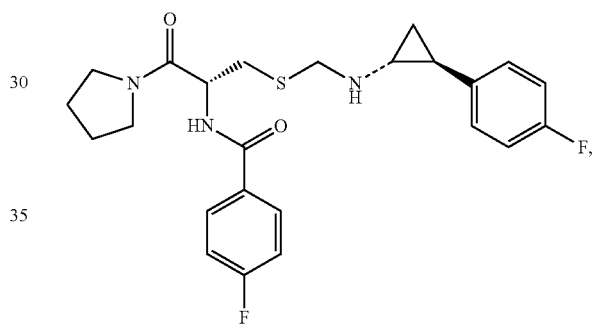
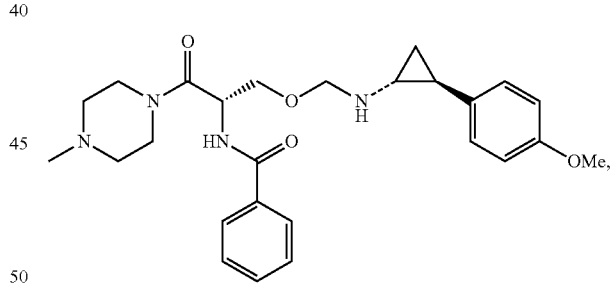
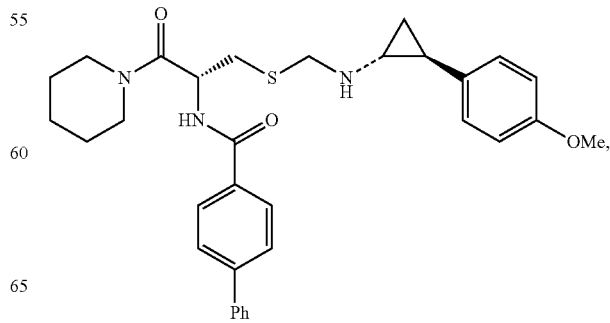

99
-continued
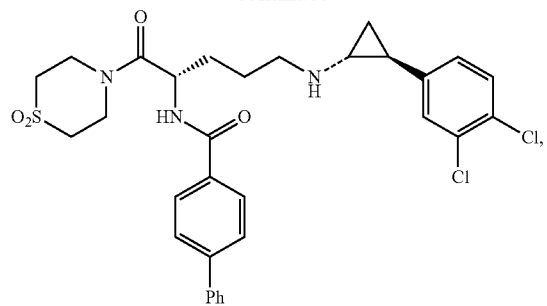
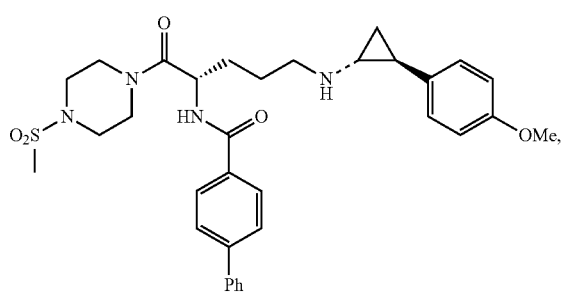
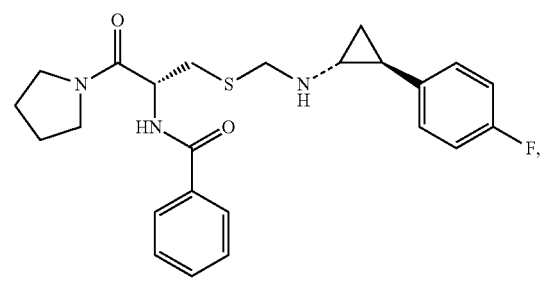
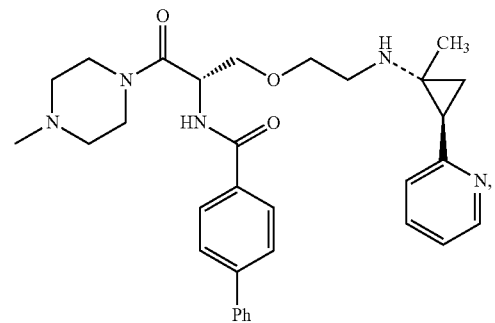
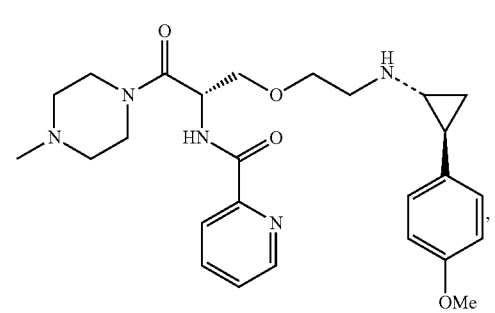
100
-continued
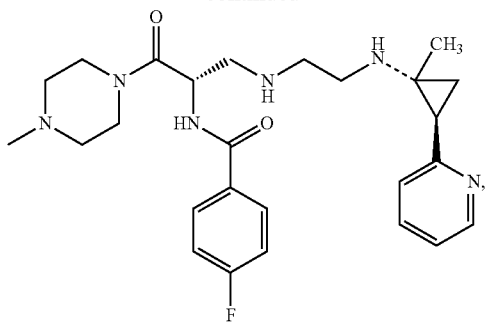
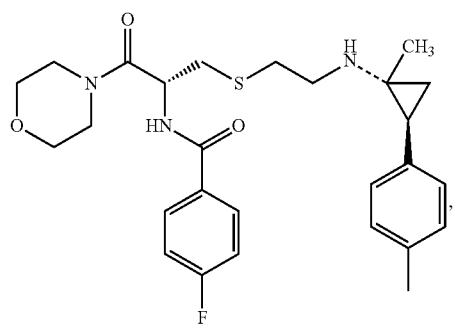
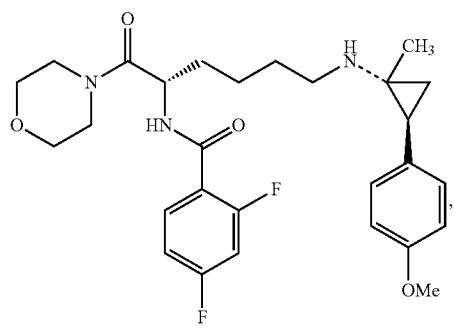
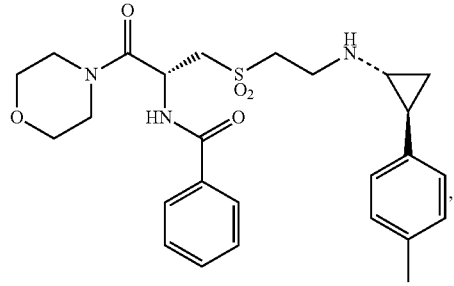
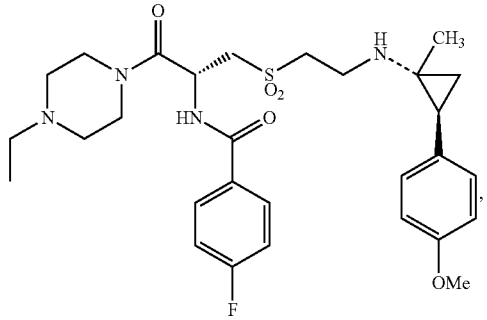

101
-continued
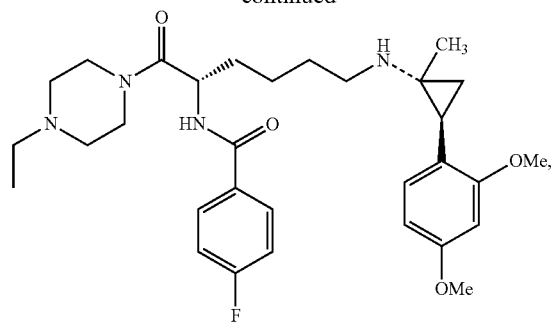
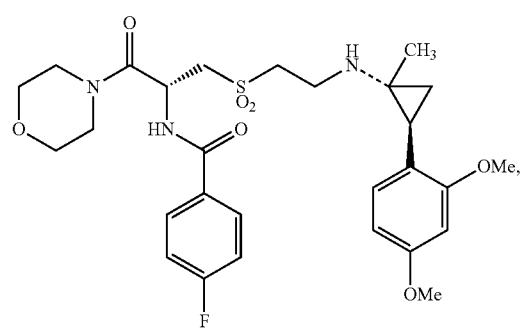
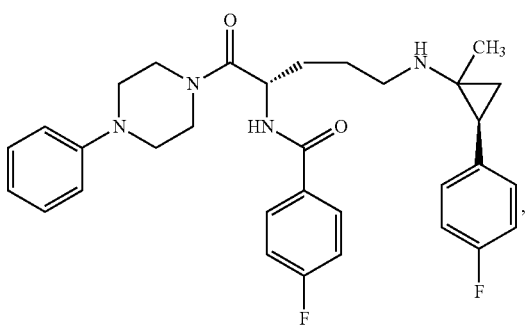
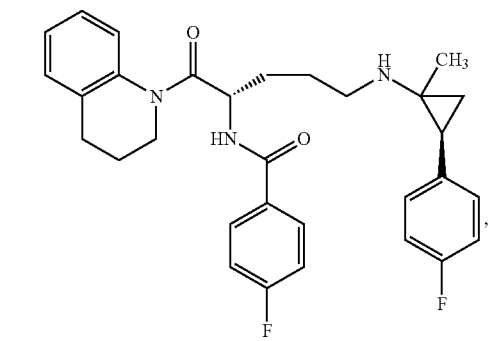
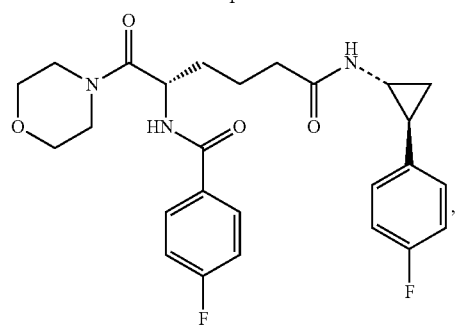
102
-continued
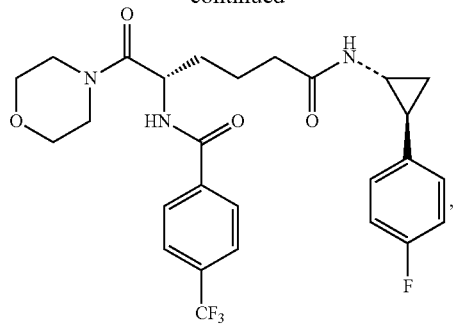
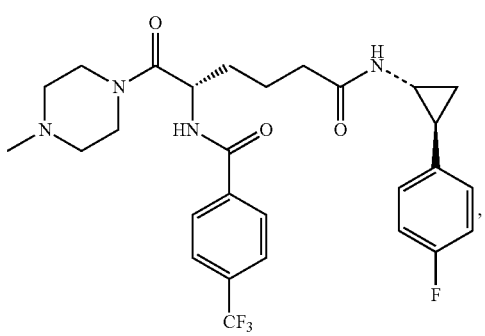
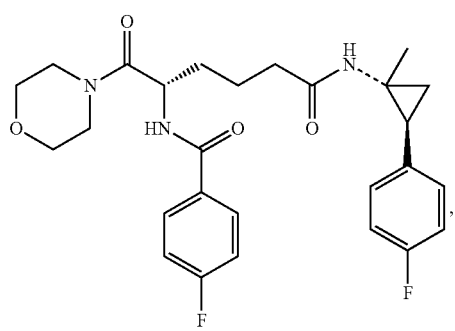
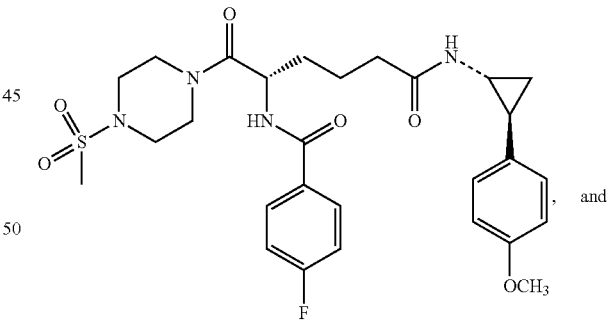, and
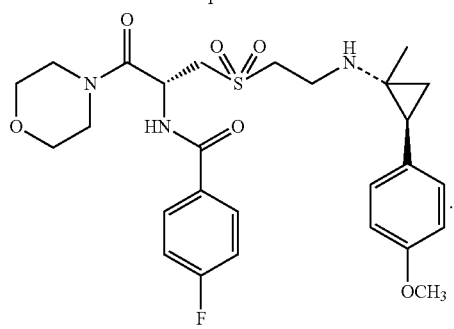

Biological Activity

The activity of the Examples above may be illustrated in the following assays. Compounds listed above, which may not yet have been made and/or tested, are predicted to have activity in these assays.

Assaying the inhibition of KDM1A can be determined in vitro, in cultured cells, and in animals. There are a variety of spectrophotometric methods to detect the results of demethylation of methylated lysines, viz., detecting the products of KDM1A demethylase oxidative activity on a peptide fragment of at least 18 amino acid representing the N-terminus of the histone H3 substrate that contains a monomethyl at the fourth lysine residue. Hydrogen peroxide, one product of the KDM1A demethylase reaction, reacts with horseradish peroxidase and dihydroxyphenoxazine (ADHP) to produce the fluorescent compound resorufin (excitation=530-560 nm:emission=590 nm). The KDM1A demethylase enzyme activity can obtained from mammalian cells or tissues expressing KDM1A from an endogenous or recombinant gene and purified or assayed from a whole cell extract. These methods can be used to determine the concentration of the disclosed compounds can inhibit fifty percent of the enzyme activity ($IC_{50}$). In one aspect, the disclosed compounds exhibit inhibition fifty percent of the KDM1A enzyme activity at a concentration of less than 500 nM, less than 100 nM, less than 50 nM or less than 10 nM.

The association of KDM1A with other proteins can be determined by a variety of both in vitro and in vivo methods known to one skilled in the art. For example, the disruption of KDM1A with associated proteins can be determined in an electromobility shift assay (EMSA). In various aspects, the disruption of the physical association of KDM1A with CoRest by the disclosed compounds can be observed using EMSA. In another example, the disruption of KDM1A with associated proteins can be determined by immunoprecipitation followed by separation of the co-precipitated proteins by mass spectroscopy or by get electrophoresis. In another example, the disruption of KDM1A association with CoRest can be determined by the ability of KDM1A to act on a nucleosomal substrate containing K4 or K9 methylated histone H3, a substrate that requires the presence of both KDM1A and CoRest. The disclosed compounds could be used to assay inhibition of CoRest association with KDM1A using nucleosomal substrate; such compounds may not inhibit KDM1A enzymatic activity as determined by the use of the histone H3 K4 methylated peptide substrate.

The inhibition of KDM1A can be determined in a cell-based assay. For example, KDM1A is an essential enzyme and prolonged inhibition of KDM1A will result in cell death, thus cell growth inhibition, arrest of cell growth or cell death can be assayed. In another aspect, genes induced by androgens and estrogens require KDM1A activity; inhibition by the disclosed compounds of KDM1A will abrogate the induction of gene expression in cells treated with androgens or estrogens. These effects can be measured, e.g., using quantitative PCR of mRNA to measure the magnitude of gene expression for androgen- and estrogen-dependent genes. KDM1A activity is required for the repression of transcription of specific genes. Inhibition of KDM1A by the disclosed compounds could de-repress the expression such genes in cell. These genes include Meis1, VEG-A, AIM1, HMOX1, VIM, SKAP1, BMP, EOMES, FOXA2, HNF4, SOX17, GH, PSA, pS2, GREB1, GR-1b, PRL, TSHB, SYN1, HBG, SCN1A, SCN2a, and SCN3A the expression of which can be assayed using quantitative PCR of mRNA before and at various time following the treatment of cells with the disclosed compounds. In another aspect, KDM1A is a regulator of leukemic stem cell potential and is required for oncogenic transformation of myeloid cells to acute myeloid leukemia (AML) by MLL-AF9. Inhibition of KDM1A in MLL-AF9-transformed cells grown in culture overcomes the arrest in differentiation to resulting in a more mature cell expressing the CD11b surface antigen, a monocytic cell antigen. Thus, inhibition of KDM1A can be assayed using an AML cell line such as THP-1 grown in culture quantifying the proportion of cells newly expressing the CD11b antigen using fluorescence activated cell sorting (FACS). A similar assay using FACS to count cells displaying the CD14 or CD86 can be also used, each of which are characteristic of more mature cells along the macrophage/monocytic lineage. Other cells lines derived from patients with acute myeloid leukemia such as MV4;11 or MOLM-13 cells can be used for this assay. Other markers of differentiation along the macrophage/monocyte lineage can be similarly assayed by FACS such as CD14 and CD86. Other AML cell lines such as MPLM-13 or MV4;11 can be assayed for the induction of either specific genes mentioned above or the differentiation markers as well as cell growth or apoptosis by Annexin V staining and FACS enumeration.

The selectivity of the disclosed compounds for KDM1A can be determined by assaying the $IC_{50}$ of the disclosed compounds for other FAD-dependent aminoxidases such as monoamine oxidase A (MAO-A), monoamine oxidase B (MAO-B), IL4I1, KDM1B, or SMOX. As such, a disclosed compound would inhibit KDM1A with an $IC_{50}$ that is 50-fold, or 100-fold or 250-fold or 500-fold less than for MAO-A or MAO-B.

Additional Demethylase Assays

The histone demethylase assay can be performed essentially as described in Shi, Y et al. Cell 199, 941-953 (2004). Briefly, bulk histones, histone peptides or nucleosomes are incubated with purified human recombinant KDM1A, in the histone demethylase activity (HDM) assay buffer 1 (50 mM Tris pH 8.5, 50 mM KCl, 5 mM MgCl, 0.5% BSA, and 5% glycerol) from 30 minutes to 4 hours at 37° C. A typical reaction is conducted in 100 microliters in which either 20 micrograms of purified bulk histones or 3 micrograms of modified histone peptides are used as substrates. Different amounts of KDM1A ranging from 1-20 micrograms are used in the reaction along with, as necessary, other co-factors such as FAD or CoREST, depending on the chosen substrate. The reaction mixture is analyzed by SDS-PAGE and Western blotting using histone methyl-specific antibodies or by formaldehyde formation assay to examine the removal and conversion of the methyl group to formaldehyde, or by mass spectrometry in the case of peptide substrates to identify the demethylated histone peptide.

Bulk histones (e.g., 4 mg) are incubated with the indicated amounts of recombinant proteins or complexes in histone demethylase (HDM) assay buffer A (50 mM Tris pH8.5, 50 mM KCl, 5 mM MgCl, 5% glycerol, 0.2 mM phenylmethylsulphonyl fluoride and 1 mM dithiothreitol) in a final volume of 10 ml for 12-16 h at 37 8 C. For nucleosomes (0.3 mg) or mononucleosome (0.3 mg), HDM buffer A containing 0.1% NP40 can be used. The reaction mixture can then be analyzed by SDS-PAGE followed by Western blotting. Antibodies against mono- or di-methyl K4 in histone H3 and acetyl-K9/K14 of histone H3 are used to detect the degree of methylation and acetylation, respectively. Western blots are then quantified by densitometry or by intensity of luminescence.

Alternatively, a standard flurogenic assay can be used in which the methylated histone substrate is tethered to the bottom of a 96 well plate (or to beads resting in the plate)

using biotin conjugated to the histone methylated substrate and strepavidin (SA) on beads or SA attached to the plate to secure the biotinylated substrate. After incubation of the KDM1A enzyme in histone demethylase buffer A, the demethylated histone substrate can be detected using antibodies specific for demethylated H3K4 substrate conjugated to a fluor or some other agent that can be detected. A variation on that assay method would employ an antibody directed against the methylated version of the histone in which the amount of substrate is quantified before and after incubation with the enzyme. Yet another version of a similar assay would employ a fluorescence resonance energy transfer (FRET) system of detection in which the antibody recognizing the methylated version is conjugated or otherwise linked to an entity, e.g., a bead or a large carrier molecule on which a fluorophore (donor) is attached and the fluorophore (acceptor) is bound to an entity linked to the substrate.

Alternatively, the production of $H_2O_2$ during the KDM1A reaction can be detected fluometrically. In this system, the production of $H_2O_2$ is detected in the HDM assay buffer after exposure to substrate, co-factor and enzyme using ADHP (10-Acetyl-3,7-dihydroxyphenoxazine) as a fluorogenic substrate for horse radish peroxidase (HRP). ADHP (also known as Amplex Red Reagent) is the most stable and sensitive fluorogenic substrate for HRP. The florescent product is resorufin. Sensitivity can be as low as $10^{-15}$ M of target protein. The signal is read using a fluorescence microplate reader at excitation and emission wavelengths of 530-560 nm and 590 nm, respectively.

Additionally, the KDM1A reaction can include other factors which may influence the activity of KDM1A. Such factors might include CoREST, NuRD complexes, DNMT1, HDAC1, HDAC2, and HDAC3, for example, as proteins known to associate with KDM1A or KDM1A-containing complexes. Interactions that influence any aspect of the KDM1A activity including specificity for template, substrate, $K_m$, $K_{cat}$, or sensitivity to FAD concentrations can be assayed. For example, an in vitro interaction assay between KDM1A and CoREST can be performed adding recombinant KDM1A (e.g., 10 mg) and CoREST (e.g., 5 mg) mixed and incubated for 1 h at 4-8° C., fractionated by Superdex 200 gel filtration column in a buffer containing 20 mM Tris-HCl pH 7.9, 500 mM KCl, 10% glycerol, 0.2 mM EDTA, 1 mM dithiothreitol, 0.1% Nonidet P40 and 0.2 mM phenylmethylsulphonyl fluoride, and then analyzed by silver staining.

For co-immunoprecipitation of mononucleosomes with KDM1A and CoREST, nucleosomes (1.5 mg) can be digested with micrococcal nuclease and incubated with recombinant KDM1A (e.g., 1 mg), CoREST (e.g., 500 ng) or both proteins in HDM buffer A containing 0.1% NP40 for 1 h at 4-8° C. Antibodies directed against KDM1A or CoREST attached to an affinity resin are added and after extensive washing with HDM buffer A containing 0.1% NP40, the bound proteins are eluted with a wash buffer. KDM1A activity can be assayed in the eluate or the concentration of KDM1A can be determined by quantitative Western blotting.

Compounds were tested in a 10-dose $IC_{50}$ mode fluorescence coupling enzyme assay with 3-fold serial dilution in duplicate starting at 100 μM. The production of FAD-dependent $H_2O_2$ as a result of demethylase activity of LSD1 on 10 μM histone H3(1-21)K4me2 peptide substrate was measured by coupling with HRP and Amplex Red to yield resorufin (fluorescence measured at Ex/Em=535/590 nm on EnVision, Perkin Elmer). Results are given below in Table 1.

TABLE 1

| Example No. | % at 30 min, MLM: + is ≥20% − is <20% | KDM1A $IC_{50}$ + is ≤1 uM − is >1 uM |
|---|---|---|
| 1 | ND | + |
| 2 | − | + |
| 3 | + | + |
| 4 | + | + |
| 5 | ND | + |
| 6 | + | + |
| 7 | − | + |
| 8 | + | − |
| 9 | + | + |
| 10 | − | + |
| 11 | + | + |
| 12 | + | + |
| 13 | − | + |
| 14 | − | + |
| 15 | − | ND |
| 16 | + | + |
| 17 | − | + |
| 18 | − | + |
| 19 | − | + |
| 20 | − | + |
| 21 | − | + |
| 22 | + | + |
| 23 | ND | + |
| 24 | + | + |
| 25 | + | − |
| 26 | + | + |
| 27 | + | + |
| 28 | − | + |
| 29 | − | ND |

Ex Vivo Differentiation of Purified Human CD34+ Cells into the Erythroid Lineage Human CD34+ cells isolated from the venous blood of healthy donors after mobilization by granulocyte colony stimulating factor (G-CSF) are grown and differentiated ex vivo for a 14 day incubation using a two-phase culture method described in Cui, S., et al. Mol Cell Biol 31, 3298-3311 (2011). Cells are counted using a hemocytometer and viability determined by trypan blue exclusion. Test article (candidate compounds) dissolved in an appropriate solvent compatible with physiologic conditions is added daily to fresh culture medium beginning on Day 4 through Day 14 at a range of test concentrations. Cell morphology and stage of differentiation is determined by Wright-Giemsa staining.

Flow Cytometry to Determine Differentiation Surface Markers and HbF Content

Cultured erythroid cells are stained with phycoerythrin (PE)-Cy7-conjugated anti-CD34, PE-conjugated anti-CD71, and PECy5-conjugated anti-glycophorin A antibodies. To determine the concentration of cytoplasmic HbF, cells are fixed in 0.05% glutaraldehyde for 10 minutes, permeabilized with 0.1% Triton X-100 for 5 minutes and stained with allophycocyanin-conjugated anti-HbF antibody. Stained cells are sorted and counted using a FACS analyzer.

Western Blots to Determine Presence and Concentration of KDM1A and Histone H3 and H3 Modifications.

Cells are lysed in Laemmli sample buffer and subjected to SDS-PAGE. Proteins are transferred from the gel to nitrocellulose and probed with antibodies against KDM1A, and/or histone H3, mono-methyl (H3K4me1) and/or dimethyl histone H3 K4 (H3K4me2) and then probed with fluorescence-conjugated secondary antibodies. Proteins concentrations are quantified with an imaging system.

Chromatin Immunoprecipitation (ChIP) Assays to Determine Protein Occupancy at Genome-Specific Sites.

ChIP assays are carried out in an immunoprecipitation (IP) buffer with or without SDS depending on the sensitivity of the KDM1A antibody to SDS. Briefly, typically 3×10⁷ cells are used per KMD1A ChIP and 3×10⁶ cells per H3K4me2 ChIP. After 10 minutes of 0.75% formaldehyde treatment, cells are harvested and sonicated in the ChIP lysis buffer (1% Triton X-100, 10 mM EDTA, 50 mM Tris-HCl and protease inhibitors) to produce soluble chromatin with average sizes between 300 and 1000 bp. The chromatin samples are then diluted 10-fold in the dilution buffer (5 mM EDTA, 25 mM Tris-HCl, 167 mM NaCl, and cocktails of protease inhibitors) and pre-cleaned for 1 hour using salmon sperm DNA/protein-A agarose beads. Ten micrograms of rabbit anti-KDM1A antibody, 3 microliters of anti-H3K4me2 or control antibodies are then added to each sample and incubated overnight at 4° C. To collect the immunocomplexes, 40 microliters of salmon sperm DNA/protein-A agarose beads are added to the samples for 1 hour at 4° C. The beads are washed three times in wash buffer (0.1% Triton X-100, 5 mM EDTA, 30 mM Tris-HCl, 150 mM NaCl and the washed once in wash buffer 2 (1% Triton X-100, 5 mM EDTA, 30 mM Tris-HCl, 150 mM NaCl). The bound protein-DNA complexes are eluted with 100 microliters of elution buffer (1% SDS, 0.1 M NaHCO3, 250 mM NaCl, and 0.2 micrograms protease K) and de-cross-linked at 65° C. for 4 hr. The de-crosslinked chromatin DNA is further purified by QIAquick polymerase chain reaction (PCR) Purification Kit (Qiagen) and eluted in 100 microliters of TE buffer. Four microliters of eluted DNA sample is used for each PCR reaction. Thirty-six PCR cycles can be used for KDM1A ChIP and 32 PCR cycles for H3K4mme2 ChIP. Appropriate primers for loci of interest, e.g., the gamma globin gene, are used.

For globin-specific ChIP analysis, the assays are performed as described in Cui, S., et al. Mol Cell Biol 31, 3298-3311 (2011). For example, ethylene glycol bis(succinimidyl succinate) or formaldehyde can be used as a cross-linker. Antibodies against target proteins such as KDM1A and histone H3 with or without methyl modifications can be used for immunoprecipitation. DNA contained in the immunoprecipitate can be quantified by real-time quantitative PCR (RT-qPCR) assay using primer for human embryonic, gamma, and adult beta-globin promoter sequences; primers for intergenic regions between the embryonic and gammaG-globin genes can be used as a negative control.

Hemoglobin Analysis by HPLC

Cells are lysed and can be analyzed for hemoglobin composition using the Bio-Rad Variant II Hemoglobin Testing System equipped with an ion-exchange HPLC column (Hercules).

Mouse Models for Testing Induction of Gamma Globin Gene Expression

Test article can be dissolved in a physiologically compatible solvent for injection into normal mice or mice transgenic for the yeast artificial chromosome (YAC) containing the entirety of the human beta-globin locus as described in Tanabe, O., et al. EMBO J 26, 2295-2306 (2007) or portions of the human beta-globin locus. Test article can be administered daily intraperitoneally or subcutaneously or by gavage at appropriate test doses for up to 26 weeks. At intervals, peripheral whole blood and bone marrow cells are harvested to determine gene expression by RT-qPCR of the mouse embryonic beta-like globin genes or the beta-like globin composition of red cell lysates or in the case transgenic mice carrying human beta-like globin genes both the human and mouse fetal γ- and adult β-globin genes.

Testing for Induction of Human Gamma Globin Gene Expression or HbF.

Patients with hemoglobinopathies including sickle cell disease and beta-thalassemia might benefit from treatment with an inhibitor of KDM1A. After appropriate dosing, the measure of HbF can be determined as described above. Gamma globin gene expression can be assayed in bone marrow cells using qPCR. Further, the clinical benefit of an agent inducing HbF can be measured as an increase in total hemoglobin, a reduction in sickle cell crises, a decrease in transfusion dependence, a decrease in ineffective hematopoiesis, and decrease in inflammatory biomarkers such as plasma levels of GDF15, etc.

Pharmacokinetics

The pharmacokinetic properties of the Examples above, including absorption, distribution, metabolism, and excretion, may be illustrated in the following assays. Compounds listed above, which may not yet have been made and/or tested, are predicted to have activity in these assays.

Metabolic Stability in Human and Murine Liver Microsomes

The metabolic stability of compounds disclosed herein in pooled human liver microsomes (HLM) and pooled male mouse liver microsomes (MMLM) was determined according to the following protocol, in which the concentrations of compounds in reaction systems were evaluated by LC/MS/MS for estimating the stability in liver microsomes.

Study Design

Pooled human liver microsomes (HMMCPL; PL050B) and pooled male mouse liver microsomes (MSMCPL; MS033) were purchased from CellzDirect (Invitrogen). Microsomes were stored at −80 C prior to use.

A master solution was prepared containing microsome (stock concentration 5 mg/mL, volume 50 μL, final concentration 0.5 mg/mL), $MgCl_2$ solution (stock concentration 50 mM, volume 50 μL, final concentration 5 mM), phosphate buffer (stock concentration 200 mM, volume 250 μL, final concentration 100 mM), and water (volume 95 μL. Five μL of 200 μM test compounds or control solution (control compound: verapamil) was then added. The final concentration of test compounds or verapamil in the reaction system was 2 μM. The mixture was pre-warmed at 37 C for 5 min.

The reaction was started with the addition of 50 μL of 10 mM NADPH solution at the final concentration of 1 mM and carried out at 37 C. 50 μL of ultra-pure $H_2O$ was used instead of NADPH solution in the negative control.

Aliquots of 50 μL were taken from the reaction solution at 0 and 30 min. The reaction was stopped by the addition of 3 volumes of cold methanol with IS (200 nM imipramine, 200 nM labetalol and 2 μM ketoprofen) at the designated time points. Samples were centrifuged at 16,000 g for 10 minutes to precipitate protein. Aliquot of 100 μL of the supernatant was diluted by 100 μL ultra-pure $H_2O$, and the mixture was used for LC/MS/MS analysis. All experiments were performed in duplicate.

Bioanalytical Method

Samples were analyzed using liquid chromatography-mass spectrometry. The LC system comprised a Shimadzu liquid chromatograph separation system equipped with degasser DGU-20A3, solvent delivery unit LC-20AD, system controller CBM-20A, column oven CTO-10ASVP and CTC Analytics HTC PAL System. Chromatographic conditions included a Phenomenex column, 5.0μ $C_{18}$ (2.0×50 mm); a mobile phase of 0.1% formic acid in acetonitrile and 0.1% formic acid in water; an elution rate of 500 μL/min; column temperature 25 C; injection volume 10 μL. Mass spectrometric analysis was performed using an API 4000 instrument from AB Inc. (Canada) with an ESI interface. The data acquisition and control system were created using Analyst 1.5.1 software from ABI Inc. A turbo spray ion source and electrospray ionization were employed in a multiple reaction monitoring (MRM) scan. Additional parameters included: collision gas, 6 L/min; curtain gas, 30 L/min; nebulize gas, 50 L/min; auxiliary gas, 50 L/min; temperature, 500 C; ionspray voltage, +5500 v (positive MRM). Quadripoles Q1 and Q3 were set to 456.2 and 200.2, respectively; declustering potential (DP), entrance potential (EP), and collision cell entrance potential (CE) were set to 120, 10, and 55 v, respectively; collision cell exit potential (CXP) was 12 v.

Analysis

All calculations were carried out using Microsoft Excel. Peak areas were determined from extracted ion chromatograms. The control compounds were included in the assay. Any value of the compounds that was not within the specified limits was rejected and the experiment was repeated. The reaction system without the cofactors was used to exclude the misleading factor that resulted from instability of chemical itself.

Results

Results are shown above in Table 1 and below in Table 2. Without wishing to be bound by theory, comparative data indicates that methylation of the cyclopropyl group results in an increase in metabolic stability while at least maintaining efficacy.

TABLE 2

| Example No. | Structure | % at 30 min, MLM: + is >20% − is <20% | KDM1A IC50 |
|---|---|---|---|
| 19 | 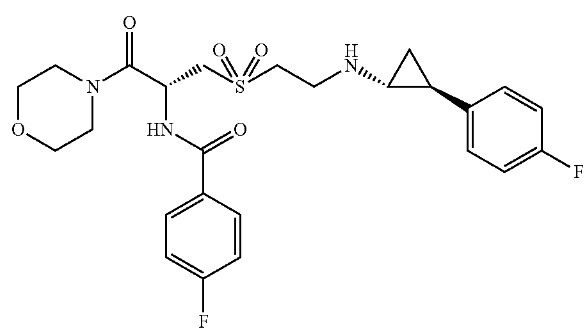 [SMILES: O=C(N[C@@H](CS(=O)(=O)CCN[C@@H]1C[C@H]1c1ccc(F)cc1)C(=O)N1CCOCC1)c1ccc(F)cc1] | 2.3% | 136 |
| 17 | 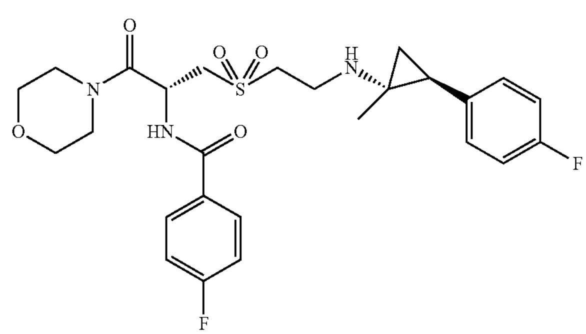 [SMILES: C[C@@]1(NCCS(=O)(=O)C[C@H](NC(=O)c2ccc(F)cc2)C(=O)N2CCOCC2)C[C@H]1c1ccc(F)cc1] | 2.7% | 114 |
| 9 | 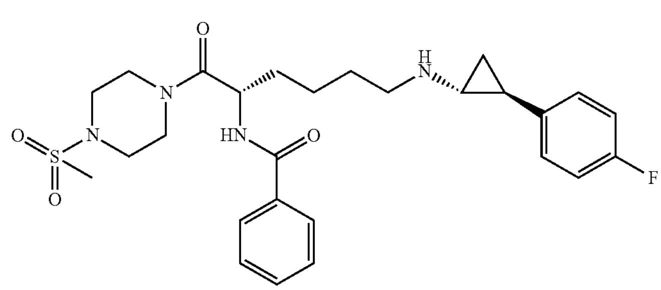 [SMILES: CS(=O)(=O)N1CCN(C(=O)[C@H](CCCCN[C@@H]2C[C@H]2c2ccc(F)cc2)NC(=O)c2ccccc2)CC1] | 54% | 5.1 |

Metabolic Stability in Murine Liver Microsomes

TABLE 2-continued

Metabolic Stability in Murine Liver Microsomes

| Example No. | Structure | % at 30 min, MLM: + is >20% − is <20% | KDM1A IC50 |
|---|---|---|---|
| 8 | 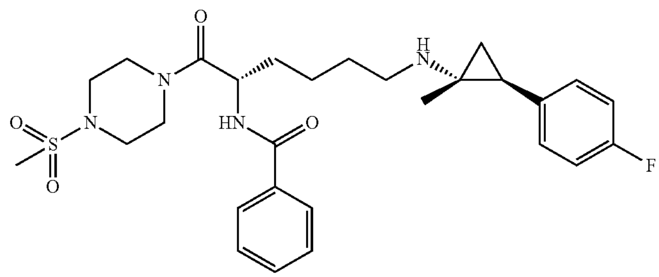 [SMILES: C[C@@]1(NCCCC[C@H](NC(=O)c2ccccc2)C(=O)N2CCN(S(C)(=O)=O)CC2)C[C@H]1c1ccc(F)cc1] | 65% | ND |

Compositions

The following are examples of compositions which may be used to deliver compounds disclosed herein. These may be encapsulated or wet granulated using methods known in the art.

COMPOSITION EXAMPLE 1

| Ingredients | Concentration (w/w %) |
|---|---|
| Compound of Formula I | 30% |
| Lactose | 68% |
| Magnesium Stearate | 2% |

COMPOSITION EXAMPLE 2

| Ingredients | Concentration (w/w %) |
|---|---|
| Compound of Formula I | 50% |
| Lactose | 38% |
| Magnesium Stearate | 2% |

From the foregoing description, one skilled in the art can easily ascertain the essential characteristics of this invention, and without departing from the spirit and scope thereof, can make various changes and modifications of the invention to adapt it to various usages and conditions.

OTHER EMBODIMENTS

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

All references cited in this specification are hereby incorporated by reference. The discussion of the references herein is intended merely to summarize the assertions made by their authors and no admission is made that any reference constitutes prior art relevant to patentability. Applicant reserves the right to challenge the accuracy and pertinence of the cited references.

What is claimed is:

1. A method of treatment of cancer comprising the administration of a therapeutically effective amount of a compound of Formula I:

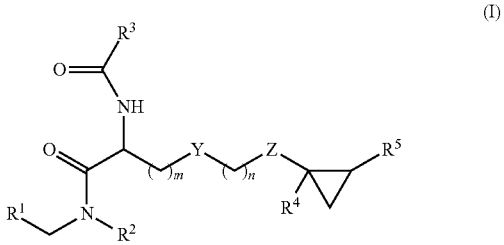

(I)

or a salt thereof, wherein:

Y is chosen from a bond, $NR^{4a}$, O, C(O)NH, NHC(O), S, $SO_2$, and $CH_2$;

Z is chosen from a bond, $NR^{4b}$, O, C(O)NH, NHC(O), S, $SO_2$, and $CH_2$;

m is an integer from 0 to 5;

n is an integer from 0 to 3;

$R^1$ and $R^2$ are each independently chosen from, alkyl, aminoalkyl, alkylsulfonylalkyl, alkoxyalkyl, aryl, arylalkyl, cycloalkyl, cycloalkylalkyl, phenyl, biphenyl, heteroaryl, heteroarylalkyl, heterocycloalkyl, and heterocycloalkylalkyl and $R^1$ and $R^2$, together with the nitrogen to which they attach, form a nitrogen-containing heterocycloalkyl or heteroaryl ring, which may be optionally substituted with between 0 and 3 $R^6$ groups; or $R^1$ and $R^2$, together with the nitrogen to which they attach, form

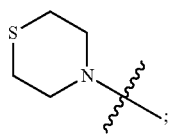 [SMILES: *N1CCSCC1]

R³ is chosen from alkylamino, cycloalkylamino, arylamino, heteroarylamino, heterocycloalkylamino, cycloalkyl, cycloalkylalkyl, aryl, arylalkyl, heteroaryl, heteroarylalkyl, heterocycloalkyl, and heterocycloalkylalkyl any of which may be optionally substituted with between 0 and 3 R⁶ groups;

R⁴, R⁴ᵃ, and R⁴ᵇ are independently chosen from hydrogen, alkyl, alkenyl, alkynyl, and cycloalkyl;

R⁵ is chosen from aryl and heteroaryl, any of which may be optionally substituted with between 0 and 3 R⁶ groups;

each R⁶ is independently chosen from hydrogen, halogen, alkyl, alkenyl, alkynyl, cycloalkyl, haloalkyl, haloalkoxy, aryl, aralkyl, heterocycloalkyl, heteroaryl, heteroarylalkyl, cyano, alkoxy, amino, alkylamino, dialkylamino, COR⁷, SO₂R⁷, NHSO₂R⁷, NHSO₂NHR⁷, NHCOR⁷, NHCONHR⁷, CONHR⁷, and CONR⁷R⁸; and R⁷ and R⁸ are independently chosen from hydrogen, and lower alkyl; or R⁷ and R⁸ may be taken together to form a nitrogen-containing heterocycloalkyl or heteroaryl ring, which may be optionally substituted with lower alkyl, to a patient in need thereof.

2. The method as recited in claim 1, wherein the cancer is a hematologic cancer.

3. The method as recited in claim 2, wherein the hematologic cancer is selected from multiple myeloma, Myelodysplastic Syndrome, Acute Myelogenous Leukemia (AML), Acute Lymphocytic Leukemia (ALL), Chronic Lymphocytic Leukemia (CLL), and Chronic Myelogenous Leukemia (CML), Hodgkin's lymphoma and non-Hodgkin's lymphoma.

4. The method as recited in claim 2, wherein the cancer is chosen from Myelodysplastic Syndrome (MDS), Acute Myelogenous Leukemia (AML), and Chronic Myelogenous Leukemia (CML).

5. The method as recited in claim 1, wherein the cancer is a non-hematologic cancer.

6. The method as recited in claim 5, wherein the non-hematologic cancer is a solid tumor.

7. The method as recited in claim 1, wherein Z is NR⁴ᵇ.

8. The method as recited in claim 7, wherein R⁴ᵇ is chosen from methyl and hydrogen.

9. The method as recited in claim 8, wherein the alkyl, whether by itself or as a named part of another non-cyclic substituent, is C₁-C₈ alkyl.

10. The method as recited in claim 9, wherein R³ is chosen from aryl, arylalkyl, heteroaryl, and heteroarylalkyl, any of which may be optionally substituted with between 0 and 3 R⁶ groups.

11. The method as recited in claim 10, wherein R³ is chosen from aryl and heteroaryl, any of which may be optionally substituted with between 0 and 3 R⁶ groups.

12. The method as recited in claim 11, wherein m is an integer from 0 to 1; Y is chosen from NR⁴ᵃ, O, S, SO₂, and CH₂; n is an integer from 1 to 3; and R⁴ᵃ is chosen from hydrogen and alkyl.

13. The method as recited in claim 12, wherein m is 0; Y is CH₂; and n is an integer from 1 to 2.

14. The method as recited in claim 13, wherein R³ is 5-6 membered monocyclic or 8-12 membered bicyclic heteroaryl, in which between one and five ring members may be heteroatoms chosen from N, O, and S, and which may be optionally substituted with between 0 and 3 R⁶ groups.

15. The method as recited in claim 14, wherein R³ is 5-6 membered monocyclic heteroaryl, in which between one and four ring members may be heteroatoms chosen from N, O, and S, and which may be optionally substituted with between 0 and 3 R⁶ groups.

16. The method as recited in claim 15, wherein each R⁶ is chosen from lower alkyl, halogen, lower alkoxy, OCF₃ and CF₃.

17. The method as recited in claim 16, wherein R³ is chosen from

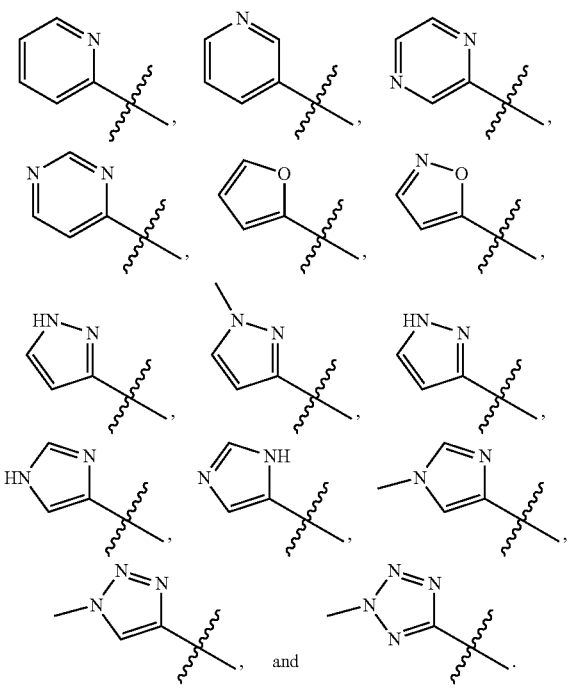

18. The method as recited in claim 17, wherein R⁴ is hydrogen.

19. The method as recited in claim 18, wherein the nitrogen-containing heterocycloalkyl or heteroaryl ring formed by R¹ and R² together with the nitrogen to which they are attached contains 3 to eight atoms.

20. The method as recited in claim 19, wherein R¹ and R² are taken together to form a nitrogen-containing heterocycloalkyl, which may be optionally substituted with between 0 and 3 R⁶ groups.

21. The method as recited in claim 20, wherein the nitrogen-containing heterocycloalkyl is chosen from:

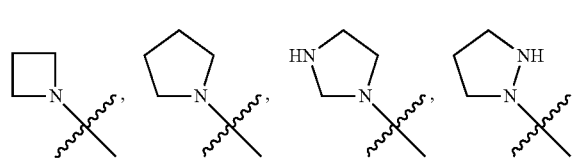

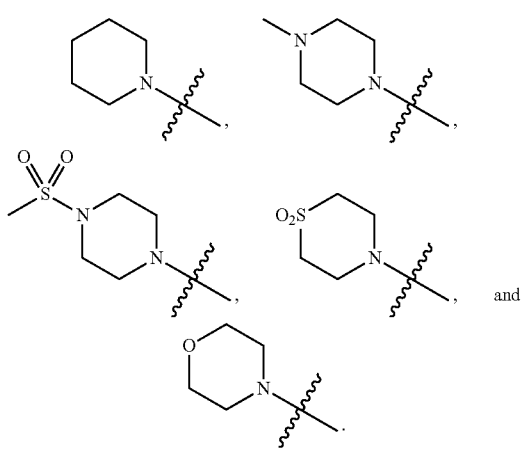

22. The method as recited in claim 21, wherein the nitrogen-containing heterocycloalkyl is chosen from:

23. The method as recited in claim 22, wherein n is 2.

24. The method as recited in claim 23, wherein $R^5$ is aryl, which may be optionally substituted with between 0 and 3 $R^6$ groups.

25. The method as recited in claim 24, wherein $R^5$ is phenyl, which may be optionally substituted with between 0 and 3 $R^6$ groups.

26. The method as recited in claim 12, wherein $R^3$ is aryl, optionally substituted with between 0 and 3 $R^6$ groups.

27. The method as recited in claim 26, wherein $R^3$ is chosen from phenyl and biphenyl, either of which may be optionally substituted with between 0 and 3 $R^6$ groups.

28. The method as recited in claim 27, wherein m is an integer from 0 to 1; Y is chosen from $NR^{4a}$, O, S, $SO_2$, and $CH_2$; n is an integer from 1 to 3; and $R^{4a}$ is chosen from hydrogen and alkyl.

29. The method as recited in claim 28, wherein m is 0; Y is $CH_2$; and n is an integer from 1 to 2.

30. The method as recited in claim 28, wherein each $R^6$ is chosen from lower alkyl, halogen, lower alkoxy, $OCF_3$ and $CF_3$.

31. The method as recited in claim 30, wherein $R^4$ is hydrogen.

32. The method as recited in claim 31, wherein n is 2.

33. The method as recited in claim 32, wherein the nitrogen-containing heterocycloalkyl or heteroaryl ring formed by $R^1$ and $R^2$ together with the nitrogen to which they are attached contains 3 to eight atoms.

34. The method as recited in claim 33, wherein $R^1$ and $R^2$ are taken together to form a nitrogen-containing heterocycloalkyl, which may be optionally substituted with between 0 and 3 $R^6$ groups.

35. The method as recited in claim 34, wherein the nitrogen-containing heterocycloalkyl is chosen from:

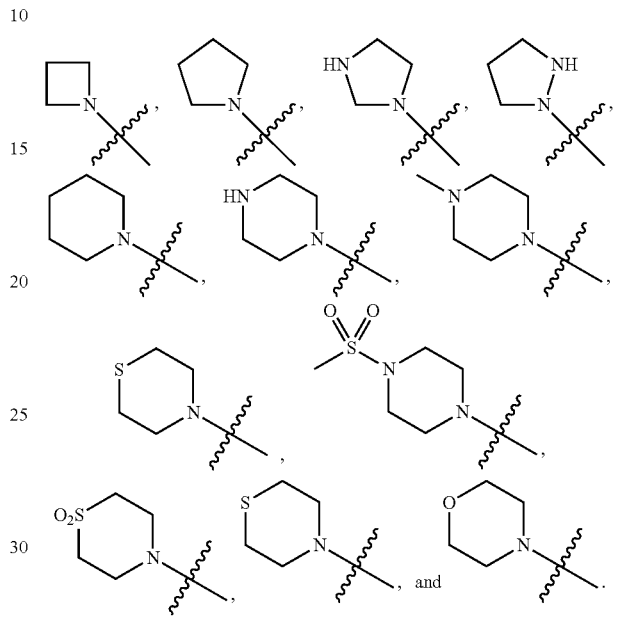

36. The method as recited in claim 35, wherein the nitrogen-containing heterocycloalkyl is chosen from:

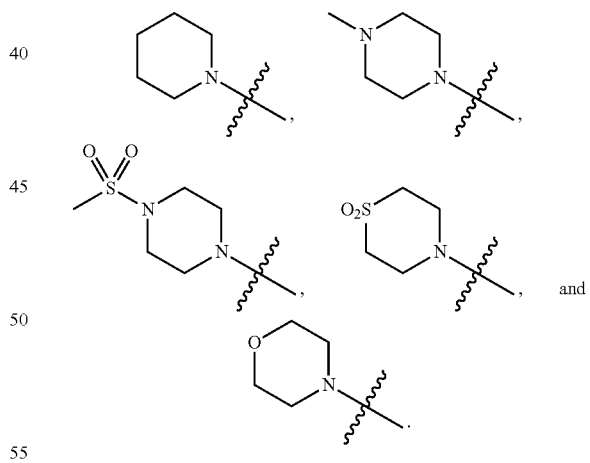

37. The method as recited in claim 36, wherein n is 2.

38. The method as recited in claim 37, wherein $R^5$ is aryl, which may be optionally substituted with between 0 and 3 $R^6$ groups, each of which is independently chosen from lower alkyl, halogen, lower alkoxy, $OCF_3$ and $CF_3$.

39. The method as recited in claim 38, wherein $R^5$ is phenyl, which may be optionally substituted with between 0 and 3 $R^6$ groups, each of which is independently chosen from lower alkyl, halogen, lower alkoxy, $OCF_3$ and $CF_3$.

40. The method as recited in claim 1, further comprising the administration of a second therapeutic agent.

41. The method as recited in claim 40, wherein the second therapeutic agent is selected from all-trans retinoic acid (ATRA), arsenic trioxide, an inhibitor of DNA methytransferases, an inhibitor of NFκB signaling, a conventional anti-neoplastic agent, a nucleoside analogue, and a checkpoint inhibitor.

42. The method as recited in claim 41, wherein the checkpoint inhibitor is a PD-1 inhibitor.

43. The method as recited in claim 42, wherein the PD-1 inhibitor is selected from pembrolizumab (KEYTRUDA®), nivolumab (OPDIVO®), pidilizumab, and BMS-936559.

44. The method as recited in claim 41, wherein the checkpoint inhibitor is a PD-L1 inhibitor.

45. The method as recited in claim 44, wherein the PD-L1 inhibitor is selected from atezolizumab (TECENTRIQ®), avelumab (BAVENCIO®), durvalumab (IMFINZI®), atezolizumab, and avelumab.

46. The method as recited in claim 41, wherein the second therapeutic agent is all-trans retinoic acid (ATRA).

47. A method of treatment of cancer comprising the administration of a therapeutically effective amount of a compound of Formula I:

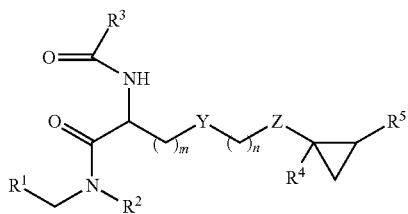

or a salt thereof, wherein:
Y is $CH_2$;
Z is $NR^{4b}$;
m is 0;
n is 2;
$R^1$ and $R^2$, together with the nitrogen to which they attach, form

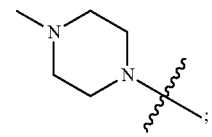 [SMILES: *N1CCN(C)CC1]

$R^3$ is chosen from phenyl and biphenyl, either of which may be optionally substituted with between 0 and 3 $R^6$ groups;
$R^4$, $R^{4a}$, and $R^{4b}$ are hydrogen;
$R^5$ is phenyl, which may be optionally substituted with between 0 and 3 groups each chosen from lower alkyl, halogen, lower alkoxy, $OCF_3$ and $CF_3$;
each $R^6$ is independently chosen from hydrogen, halogen, alkyl, alkenyl, alkynyl, cycloalkyl, haloalkyl, haloalkoxy, aryl, aralkyl, heterocycloalkyl, heteroaryl, heteroarylalkyl, cyano, alkoxy, amino, alkylamino, dialkylamino, $COR^7$, $SO_2R^7$, $NHSO_2R^7$, $NHSO_2NHR^7$, $NHCOR^7$, $NHCONHR^7$, $CONHR^7$, and $CONR^7R^8$; and
$R^7$ and $R^8$ are independently chosen from hydrogen, and lower alkyl; or $R^7$ and $R^8$ may be taken together to form a nitrogen-containing heterocycloalkyl or heteroaryl ring, which may be optionally substituted with lower alkyl.

48. The method as recited in claim 47 further comprising the administration of all trans-retinoic acid (ATRA).

* * * * *